United States Patent
Kostrzewski et al.

(10) Patent No.: US 11,529,195 B2
(45) Date of Patent: *Dec. 20, 2022

(54) ROBOTIC NAVIGATION OF ROBOTIC SURGICAL SYSTEMS

(71) Applicant: KB MEDICAL SA, Audubon, PA (US)

(72) Inventors: Szymon Kostrzewski, Lausanne (CH);
Jean-Marc Wismer, Lausanne (CH);
Daniel Gehriger, Lausanne (CH);
Roderik Berthelin, Lausanne (CH)

(73) Assignee: Globus Medical Inc., Audubon, PA (US)

(*) Notice: Subject to any disclaimer, the term of this patent is extended or adjusted under 35 U.S.C. 154(b) by 160 days.

This patent is subject to a terminal disclaimer.

(21) Appl. No.: 16/535,166

(22) Filed: Aug. 8, 2019

(65) Prior Publication Data

US 2020/0030040 A1  Jan. 30, 2020

Related U.S. Application Data

(63) Continuation of application No. 15/874,695, filed on Jan. 18, 2018, now Pat. No. 10,420,616.
(Continued)

(51) Int. Cl.
*G06T 7/33* (2017.01)
*A61B 34/20* (2016.01)
(Continued)

(52) U.S. Cl.
CPC .............. *A61B 34/20* (2016.02); *A61B 34/25* (2016.02); *A61B 34/30* (2016.02); *A61B 34/76* (2016.02);
(Continued)

(58) Field of Classification Search
CPC ......... A61B 34/20; A61B 34/25; A61B 34/30; A61B 34/76; A61B 46/10; A61B 90/37;
(Continued)

(56) References Cited

U.S. PATENT DOCUMENTS

| | | |
|---|---|---|
| 4,150,293 A | 4/1979 | Franke |
| 5,246,010 A | 9/1993 | Gazzara et al. |
| | (Continued) | |

FOREIGN PATENT DOCUMENTS

| | | |
|---|---|---|
| EP | 3360502 A2 | 8/2018 |
| JP | 2005537583 A | 12/2005 |
| | (Continued) | |

OTHER PUBLICATIONS

US 8,231,638 B2, 07/2012, Swarup et al. (withdrawn)
(Continued)

*Primary Examiner* — Shaghayegh Azima

(57) ABSTRACT

In certain embodiments, the systems, apparatus, and methods disclosed herein relate to robotic surgical systems with built-in navigation capability for patient position tracking and surgical instrument guidance during a surgical procedure, without the need for a separate navigation system. Robotic based navigation of surgical instruments during surgical procedures allows for easy registration and operative volume identification and tracking. The systems, apparatus, and methods herein allow re-registration, model updates, and operative volumes to be performed intraoperatively with minimal disruption to the surgical workflow. In certain embodiments, navigational assistance can be provided to a surgeon by displaying a surgical instrument's position relative to a patient's anatomy. Additionally, by revising pre-operatively defined data such as operative volumes, patient-robot orientation relationships, and anatomical models of the patient, a higher degree of precision and lower risk of complications and serious medical error can be achieved.

5 Claims, 37 Drawing Sheets

Related U.S. Application Data

(60) Provisional application No. 62/447,884, filed on Jan. 18, 2017.

(51) Int. Cl.
  *A61B 34/30* (2016.01)
  *A61B 34/00* (2016.01)
  *A61B 90/00* (2016.01)
  *G06T 7/73* (2017.01)
  *A61B 46/10* (2016.01)
  *G02C 7/04* (2006.01)
  *A61B 34/10* (2016.01)
  *A61B 17/16* (2006.01)
  *A61B 17/00* (2006.01)
  *G02B 1/04* (2006.01)

(52) U.S. Cl.
  CPC .............. *A61B 46/10* (2016.02); *A61B 90/37* (2016.02); *G02C 7/049* (2013.01); *G06T 7/33* (2017.01); *G06T 7/344* (2017.01); *G06T 7/75* (2017.01); *A61B 17/1615* (2013.01); *A61B 17/1671* (2013.01); *A61B 2017/00694* (2013.01); *A61B 2017/00902* (2013.01); *A61B 2034/104* (2016.02); *A61B 2034/105* (2016.02); *A61B 2034/107* (2016.02); *A61B 2034/207* (2016.02); *A61B 2034/2046* (2016.02); *A61B 2034/2051* (2016.02); *A61B 2034/2055* (2016.02); *A61B 2034/2059* (2016.02); *A61B 2034/2065* (2016.02); *A61B 2034/2068* (2016.02); *A61B 2034/252* (2016.02); *A61B 2090/064* (2016.02); *A61B 2090/065* (2016.02); *A61B 2090/363* (2016.02); *A61B 2090/364* (2016.02); *A61B 2090/374* (2016.02); *A61B 2090/376* (2016.02); *A61B 2090/378* (2016.02); *A61B 2090/3762* (2016.02); *A61B 2090/3983* (2016.02); *G02B 1/043* (2013.01); *G02C 2202/16* (2013.01); *G06T 2207/10016* (2013.01); *G06T 2207/30012* (2013.01); *G06T 2207/30196* (2013.01); *G06T 2207/30204* (2013.01); *G06T 2210/41* (2013.01)

(58) Field of Classification Search
  CPC ........... A61B 2017/00902; A61B 2017/00694; A61B 17/1671; A61B 17/1615; A61B 2090/3983; A61B 2090/3762; A61B 2090/376; A61B 2090/374; A61B 2090/364; A61B 2090/363; A61B 2090/065; A61B 2090/064; A61B 2034/252; A61B 2034/2068; A61B 2034/265; A61B 2034/2046; A61B 2034/107; A61B 2034/105; A61B 2034/104; A61B 2034/2051; A61B 2034/2055; A61B 2034/2065; A61B 2034/207; G06T 7/344; G06T 7/75; G06T 7/33; G06T 2210/41; G06T 2207/30204; G06T 2207/30196; G06T 2207/30012; G06T 2207/10016; G02C 7/049; G02C 2202/16; G02B 1/043
  See application file for complete search history.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |

(56) References Cited

U.S. PATENT DOCUMENTS

| | | |
|---|---|---|
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 3,004,121 A1 | 8/2011 | Sartor |
| 7,988,215 B2 | 8/2011 | Seibold |
| 7,996,110 B2 | 8/2011 | Lipow et al. |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 3,046,057 A1 | 10/2011 | Clarke |
| 8,035,685 B2 | 10/2011 | Jensen |
| 8,046,054 B2 | 10/2011 | Kim et al. |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |

(56) References Cited

U.S. PATENT DOCUMENTS

| | | |
|---|---|---|
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |

(56) References Cited

U.S. PATENT DOCUMENTS

| | | |
|---|---|---|
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0025183 A1 | 9/2001 | Shadidi |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2004/0106916 A1* | 6/2004 | Quaid ............. A61B 34/71 606/1 |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0142657 A1* | 6/2006 | Quaid ............. A61B 17/1703 600/424 |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1* | 1/2008 | Jensen ............. A61B 90/11 600/424 |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0077158 A1 | 3/2008 | Haider et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Mired et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0218770 A1* | 9/2008 | Moll ............. A61G 7/0503 356/614 |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0063387 A1 | 3/2010 | Timinger |
| 2010/0076455 A1 | 3/2010 | Birkenbach et al. |
| 2010/0125286 A1 | 5/2010 | Wang et al. |
| 2010/0130986 A1 | 5/2010 | Mailloux et al. |
| 2010/0168723 A1* | 7/2010 | Suarez ............. A61B 90/50 606/1 |
| 2010/0228117 A1 | 9/2010 | Hartmann |
| 2010/0228265 A1 | 9/2010 | Prisco |
| 2010/0234724 A1* | 9/2010 | Jacobsen ............. A61B 34/20 600/424 |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0160569 A1* | 6/2011 | Cohen ............. G06T 19/00 600/424 |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |

(56) References Cited

U.S. PATENT DOCUMENTS

| | | |
|---|---|---|
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0109152 A1 | 5/2012 | Quaid |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0185099 A1* | 7/2012 | Bosscher ............... B25J 9/1689 700/264 |
| 2012/0190981 A1* | 7/2012 | Harris ............... A61B 5/150503 604/95.01 |
| 2012/0197182 A1 | 8/2012 | Millman et al. |
| 2012/0209117 A1 | 8/2012 | Mozes et al. |
| 2012/0226145 A1* | 9/2012 | Chang ................... A61B 34/30 600/424 |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0010081 A1* | 1/2013 | Tenney ................. H04N 13/20 348/47 |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096573 A1* | 4/2013 | Kang ..................... A61B 34/30 606/130 |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0228860 A1* | 8/2014 | Steines ................. A61B 34/30 606/130 |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0100066 A1* | 4/2015 | Kostrzewski .......... A61B 90/06 606/130 |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1* | 11/2015 | Alvarez ............... A61B 5/0059 606/130 |
| 2015/0342647 A1 | 12/2015 | Frankel et al. |
| 2015/0347682 A1* | 12/2015 | Chen ..................... G16H 80/00 705/2 |
| 2016/0005194 A1 | 1/2016 | Schretter et al. |
| 2016/0151120 A1 | 6/2016 | Kostrzewski et al. |
| 2016/0166329 A1 | 6/2016 | Langan et al. |
| 2016/0213415 A1* | 7/2016 | Carter ................. A61B 18/1487 |
| 2016/0235480 A1 | 8/2016 | Scholl et al. |

(56) References Cited

U.S. PATENT DOCUMENTS

| | | |
|---|---|---|
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0340389 A1* | 11/2017 | Otto ................... A61B 5/1077 |
| 2017/0360493 A1 | 12/2017 | Zucher et al. |
| 2018/0199995 A1* | 7/2018 | Odermatt ............... A61B 6/505 |
| 2018/0199996 A1* | 7/2018 | Hogan ................... A61B 34/10 |
| 2019/0015167 A1* | 1/2019 | Draelos ................. A61B 34/76 |
| 2019/0015168 A1* | 1/2019 | Verner .................. A61B 34/30 |
| 2020/0030040 A1* | 1/2020 | Kostrzewski ............. G06T 7/75 |
| 2021/0244485 A1* | 8/2021 | Coiseur ................ A61B 90/361 |

FOREIGN PATENT DOCUMENTS

| | | |
|---|---|---|
| JP | 2008237784 A | 10/2008 |
| JP | 2008538184 A | 10/2008 |
| JP | 2010519635 A | 6/2010 |
| WO | 2016087539 A2 | 6/2016 |

OTHER PUBLICATIONS

Jon T. Lea, Dane Watkins, Aaron Mills, Michael A. Peshkin, Thomas C. Kienzle, and S. David Stulberg, "Registration and Immobilization in Robot-Assisted Surgery", Journal of Image Guided Surgery, 1995, 80-87.*

* cited by examiner

System recognized contact with tissue and uses this information to fine tune the registration on-the-fly

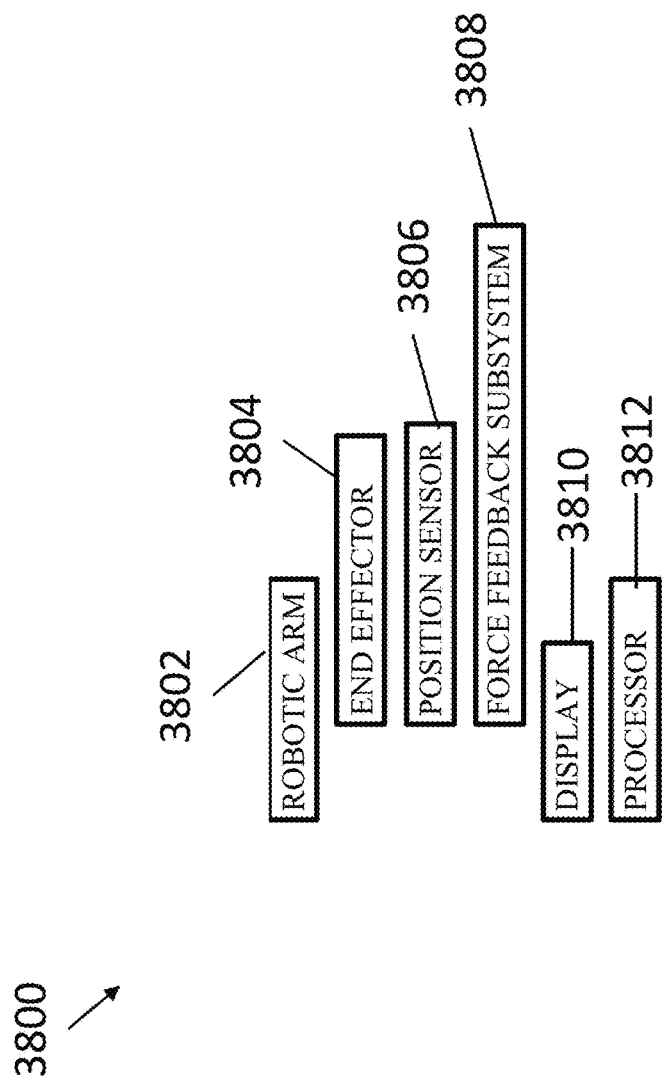

ROBOTIC NAVIGATION OF ROBOTIC SURGICAL SYSTEMS

CROSS-REFERENCE TO RELATED APPLICATIONS

This application is a non-provisional application, which is a continuation of U.S. patent application Ser. No. 15/874,695 filed on Jan. 18, 2018, which claims priority to provisional application Ser. No. 62/447,884 filed on Jan. 17, 2017, which is incorporated in its entirety herein.

FIELD OF INVENTION

This invention relates generally to robotic surgical systems. For example, in certain embodiments, the invention relates to robotic surgical systems with built-in navigation capability for position tracking during a surgical procedure.

BACKGROUND

Many surgeries (e.g., spinal and orthopedic surgeries) currently require the use of medical images displayed to the surgeon in real time, to provide visual navigation to support surgical action, gestures, and decision making. Using medical images, a surgeon can be provided with real-time feedback of the position of surgical instruments in reference to patient anatomy (as pictured by medical images).

Current surgical navigation systems are based on the principle of tracking. For example, a navigation system generally contains a tracking device which measures position of the surgical instruments and patient in real time. Different tracking devices operate on different principles. The most popular are optical tracking and electro-magnetic tracking. Optical tracking uses camera systems that measure fiducials (e.g., reflective spheres, LEDs) configured on markers having defined and known anatomy. In this way, the position and orientation of a marker can be determined and, thus, the position and orientation of the element to which they are affixed (e.g., surgical instruments, patient anatomy) can be tracked as well. In electro-magnetic tracking, the camera of an optical tracking system is replaced by a field generator. Markers are sensor units (e.g., coils) which measure spatial changes in the generated field. In this way, the position and orientation of the EM marker can be determined in reference to field generator.

There are commercial navigation systems available on the market, for example, Stealthstation S7 from Medtronic, Curve from Brain lab, electro-magnetic Kick EM from Brainlab and others. A typical workflow for use of these navigation systems follows the steps of: obtaining patient images, fixing a reference on the patient, registering the patient, and tracking instrument and patients to show real-time feedback to the surgeon. Patient images may be generated by CT, MRI, or flat-panel fluoroscopy (e.g., 0-Arm), for example. References fixed to the patient include optical markers with a fiducial mark or electro-magnetic markers. Markers are fixed using, for example, bone screws or bone fixations. Registering the patient requires defining a relationship between the patient images and the fixed marker. Registration may be performed using a point-to-point method, surface matching, or automatic registration based on images taken with fixed markers (e.g., on the patient's anatomy).

Current navigation systems have numerous limitations. These navigation systems are generally difficult to use and require additional surgeon and/or staff training for their operation. The navigation systems take up a lot of space in the operating room. For example, precious real estate in the operating room space may be occupied by a stand-alone navigation station/console with tracking camera, screens used for visual feedback, cords and plugs, power systems, controllers, and the like, creating additional clutter. Also, current optical navigation systems have a line of sight requirement, in that all tracked instruments must remain visible to the camera in order to be tracked. If there are not enough fiducials (e.g., spheres, LEDs) visible marker positions may not be able to be determined. An additional risk is that fiducial position can be misread by the navigation system due to obfuscation (e.g., by a drop of blood or transparent drape). Electro-magnetic navigation systems have problems with metal and ferromagnetic materials placed in field which can influence the field and thus add error to marker position measurement. Moreover, navigation systems are expensive, costing approximately $200k or more. The precision of the measurement is relatively low in commercial stations, for example, on the level of O.3 mm RMS error for position measurement. Additionally, the measurements are noisy. The frequency of measurement is low (i.e., approximately 20 Hz).

The most severe limitation of known navigation systems is that the navigation desynchronizes over time. The surgeon registers the patient initially at the beginning of the surgical procedure, using one or more markers attached to the patient's anatomy. Throughout the surgical procedure, the patient's anatomy shifts due to movement of the patient or as a result of the surgical procedure itself. For example, in surgeries involving elongation steps or realignment steps, the patient's anatomy will have a different position and orientation relative to the fiducial marker(s) after the elongation or realignment. Only the area local to the fiducial marker(s) remains accurate to the physical reality of the patient's anatomy. The error between the reality of the patient's anatomy and the assumed reality based on the initial registration increases with distance from the fiducial marker(s). Thus, in many surgical procedures being performed today using robotic surgical systems with known navigation systems, as the procedure progresses, the navigation system becomes more desynchronized and thus less useful to the surgeon, as it is less reflective of real life. Likewise, the likelihood of complications and serious medical error increases.

There are robotic surgical systems which are combined with a navigation system, for example, Excelsius GPS from Globus, ROSA SPINE from Medtech (currently Zimmer/Biomet), MAKO from Stryker and others. However, these systems use the same navigation system approach as the aforementioned known systems. The use of a robotic arm aids a surgeon in making precise gestures, but the systems inherit the disadvantages of navigation systems especially: training requirements, required space, line of sight, price and low precision of optical navigation over the course of a surgical procedure. The likelihood of complications and serious medical errors due to desynchronization are not reduced in these robotic surgical systems.

Thus, there is a need for robotic surgical systems for instrument guidance and navigation wherein the patient registration can be updated overtime to accurately reflect the instant patient situation.

SUMMARY

In certain embodiments, the systems, apparatus, and methods disclosed herein relate to robotic surgical systems with built-in navigation capability for patient position tracking and surgical instrument guidance during a surgical procedure, without the need for a separate navigation system. Robotic based navigation of surgical instruments during surgical procedures allows for easy registration and operative volume identification and tracking. The systems, apparatus, and methods herein allow re-registration, model updates, and operative volumes to be performed intra-operatively with minimal disruption to the surgical workflow. In certain embodiments, navigational assistance can be provided to a surgeon by displaying a surgical instrument's position relative to a patient's anatomy. Additionally, by revising pre-operatively defined data such as operative volumes, patient-robot orientation relationships, and anatomical models of the patient, a higher degree of precision and lower risk of complications and serious medical error can be achieved.

In certain embodiments, described herein is a robotic surgical system comprising a robotic arm that has a directly or indirectly attached force sensor that is used to collect spatial coordinates of a patient's anatomy. A surgeon can maneuver the robotic arm between different points in space and contact the patient at different points on the patient's anatomy with an instrument attached to the robotic arm. In certain embodiments, the instrument comprises the force sensor. Contact is determined based on haptic feedback registered by the force sensor. In certain embodiments, a threshold (e.g., a magnitude of haptic feedback) must be exceeded in order to register the contact as belonging to the patient's anatomy. Furthermore, in this way, the magnitude of haptic feedback can be used to determine the type of tissue being contacted (e.g., because bone is harder than soft tissue). In some embodiments, the instrwnent contacts a specially engineered fiducial marker attached to the patient's anatomy at one or more of a set of orienting contact points (e.g., indents), wherein the fiducial marker has an established spatial relationship with the patient's anatomy (e.g., given its known size and intended attachment at a specific known location on the patient's anatomy). A plurality of spatial coordinates can be recorded and stored electronically using a plurality of contacts of the instrwnent to the patient's anatomy.

A set of spatial coordinates recorded from contact of the instrwnent with the patient's anatomy can be used to perform many navigational and surgical guidance functions such as registration, modeling volume removal, re-registration, defining operational volumes, revising operational volumes after re-registration, converting stored volume models to physical locations, and displaying surgical relative to a patient's anatomy on navigation screens.

By mapping surfaces defined by sets of coordinates obtained by contacting a patient's anatomy to a model of their anatomy (e.g., from medical image data), a coordinate mapping can be recorded that translates between the coordinate systems of the model and physical reality. For example, the model can be represented in a medical image data coordinate system and physical reality in a robot coordinate system. Thus, a robotic surgical system can know the physical location of the patient's anatomy relative to a surgical instrument attached hereto. Using the combination of haptic-feedback-generated sets of spatial coordinates and sets of medical image data coordinates that model the surface of a patient's anatomy, the aforementioned navigational and surgical guidance functions can be performed quickly and with high precision pre- and/or intra-operatively.

A set of spatial coordinates can be used to register the patient's anatomy with a model of the patient's anatomy derived from medical image data. Medical image data may be used from any relevant technique. Examples include, but are not limited to, x-ray data, tomographic data (e.g., CT data), magnetic resonance imaging (MM) data, and flat-panel fluoroscopy (e.g., 0-Arm) data. In some embodiments, such medical image data is taken intra-operatively. In this way, the physical position and orientation of a patient's anatomy can be mapped to the model of the patient's anatomy and the robotic surgical system can know where it is in relation to the anatomy at all times.

A set of spatial coordinates can be used to update a model of a patient's anatomy after volume removal by determining the volume removed using additional contacts between the instrument and the patient's anatomy. Contacts determined to be made on the new surface of the anatomy that correspond to coordinates inside the volume of the model can be used to update the surface of the model to reflect the patient's new anatomy.

A set of spatial coordinates collected intra-operatively can be used to re-register the patient's anatomy. In this way, changes that have occurred in the anatomy, such as re-orientation or re-positioning of all of or a part of the anatomy, can be used to update the mapping between the robot coordinate system and the medical image data coordinate system as well as the model of the patient's anatomy.

A set of spatial coordinates can be used to define an operational volume, wherein the movement of a surgical instrument is constrained to be within the operational volume during a part of a procedure. For example, this can be used to limit the volume of bone removed by a surgeon. The operational volume may be defined by contacting points on the patient's anatomy and using those as vertices of a surface or by mapping a model of the anatomical volume to the set of spatial coordinates and then defining the operational volume as the mapped anatomical model expressed in the robotic surgical system's coordinate system. The operational volume can be updated after a re-registration to accurately reflect the patient's current anatomy and/or anatomical position and orientation. Likewise, a stored model (e.g., a model generated from medical image data) can be used to define a physical location of a portion (or entirety) of that model by using a coordinate mapping.

A rendering of the patient's anatomy and a surgical instrument's position relative to the anatomy can be displayed on a navigation screen for use and/or reference by a surgeon using the methods and systems described herein. By using a coordinate mapping, the location of a terminal point of a surgical instrument can be displayed along with a rendering of the patient's anatomy such that a surgeon can observe an accurate representation of the space or distances between the terminal point and the patient's anatomy. This can be used to visualize trajectories, positions, and orientations of the surgical instrument relative to the patient's anatomy. A surgeon may use this to monitor the progress of a surgical procedure, avoid a serious medical error, and/or improve patient outcome by revising the planned surgical procedure. For example, the surgeon can use the navigational display in deciding to alter the volume planned for removal or the planned orientation or trajectory of the surgical tool when removing the volume. This can be done intra-operatively.

In another aspect, the disclosed technology includes a robot-based navigation system for real-time, dynamic re-registration of a patient position (e.g., position of vertebrae of a patient) during a procedure (e.g., surgical procedure, e.g., a spinal surgery) (e.g., a combined navigation/robotic system), the system including: (a) a robotic arm (e.g., having 3, 4, 5, 6, or 7 degrees of freedom) including: an end effector [e.g., said end effector including a surgical instrument holder for insertion or attachment of a surgical instrument therein/ thereto, e.g., said robotic arm designed to allow direct manipulation of said surgical instrument by an operator (e.g., by a surgeon) when the surgical instrument is inserted in/attached to the surgical instrument holder of the end effector, said manipulation subject to haptic constraints based on the position of the end effector (and/or the surgical instrument) in relation to the patient, e.g., said surgical instrument having known geometry and fixed position in relation to the surgical instrument holder]; (ii) a position sensor for dynamically tracking a position of the end effector [e.g., during a surgical procedure) (and/or for dynamically tracking one or more points of the surgical instrument, e.g., in 30 space, e.g., during a surgical procedure) (e.g., at a rate of at least 100 Hz, e.g., 250 Hz or greater, e.g., 500 Hz or greater, e.g., 1000 Hz or greater (position determinations per second)]; and (iii) a force feedback subsystem (e.g., including sensor(s), actuator(s), controller(s), servo(s), and/or other mechanisms) for delivering a haptic force to a user manipulating the end effector (e.g., manipulating a surgical instrument inserted in the instrument holder of the end effector) (e.g., wherein the force feedback subsystem includes one or more sensors for performing one or more of (I) to (IV) as follows: (I) detecting a resistive force caused by the surgical instrument contacting, moving against, penetrating, and/or moving within a tissue of the patient, (II) distinguishing between contacted tissue types (e.g., determining when contacted tissue meets or exceeds a threshold resistance, e.g., when the tissue is bone), (III) detecting a force delivered by the operator (e.g., the surgeon, e.g., delivered by direct manipulation of the surgical instrument inserted in the surgical instrument holder of the end effector) (e.g., to cause movement of the surgical instrument and, therefore, the end effector), and (IV) distinguishing between the force delivered by the operator and the resistive force caused by movement of the surgical instrument in relation to the tissue of the patient; (b) a display [e.g., attached to, embedded within, or otherwise positioned in relation to the robotic arm being directly manipulated by the operator (e.g., surgeon) to allow for unimpeded visual feedback to the operator during the procedure, e.g., wherein the display is positioned beneath a transparent or semitransparent sterile drape, e.g., wherein the display has touch sensors for control of the display during use]; and (c) a processor of a computing device programmed to execute a set of instructions to: (i) access (e.g., and graphically render on the display) an initial registration of the patient position (e.g., position of the vertebrae of the patient) (e.g., via medical images of the patient, e.g., MRI, CT, X-rays, SPECT, ultrasound, or the like, e.g., said medical images obtained pre-operatively) (e.g., for storing and/or rendering a 3D representation, e.g., a 3D graphical representation and/or a 3D haptic representation, of an initial patient situation, e.g., wherein the 3D graphical representation is the same as or different from the 3D haptic representation, e.g., for use in displaying a real-time graphical representation of the patient situation (e.g., a target anatomy) on the display and/or for use in dynamically determining a force feedback delivered to the operator, e.g., during a surgical procedure, via the force feedback subsystem); (ii) dynamically determine a position of the end effector (e.g., dynamically determine a 3D position of one or more points of a surgical instrument positioned in relation to the end effector, e.g., within an instrument holder of the end effector); (iii) dynamically determine a force received by the end effector and/or a force to be delivered to the end effector [e.g., a force received by and/or a force to be delivered to the end effector via the surgical instrument, e.g., dynamically perform one or more of (I) to (IV) as follows: (I) determine a resistive force caused by the surgical instrwnent contacting, moving against, penetrating, and/or moving within a tissue of the patient, (II) distinguish between contacted tissue types (e.g., determining when contacted tissue meets or exceeds a threshold resistance, e.g., when the tissue is bone), (III) detect a force delivered by the operator (e.g., the surgeon, e.g., delivered by direct manipulation of the surgical instrument inserted in the surgical instrument holder of the end effector) (e.g., to cause movement of the surgical instrwnent and, therefore, the end effector), and (IV) distinguish between the force delivered by the operator and the resistive force caused by movement of the surgical instrument in relation to the tissue of the patient, (e.g., using the force feedback subsystem, e.g., the force to be dynamically determined at a rate of at least 100 Hz, e.g., 250 Hz or greater, e.g., 500 Hz or greater, e.g., 1000 Hz or greater)]; (iv) dynamically determine a position of the position sensor of the robotic arm for dynamically tracking the end effector (e.g., determine a position of the position sensor of the robotic arm upon contact of the surgical instrument with bone tissue of the patient, or other target tissue of the patient) (e.g., dynamically update the recorded position of the position sensor at a rate of at least 100 Hz, e.g., 250 Hz or greater, e.g., 500 Hz or greater, e.g., 1000 Hz or greater); (v) dynamically re-register the patient position based at least in part on an updated position of the end effector determined by the position sensor [(e.g., during a surgical procedure) (e.g., update the 30 representation of the patient situation, e.g., the 30 graphical representation and/or the 30 haptic representation, based at least in part on the updated position of the end effector when it is determined (e.g., via the force feedback subsystem) that the surgical instrument is in contact with a target anatomy, e.g., in contact with bone of the patient) (e.g., using a surface matching algorithm keyed to the initial (or previous) registration) (e.g., dynamically re-register the patient position upon detected contact of the end effector, or the surgical instrument, or a portion or component of the surgical instrument or end effector, with a pre-planned fiducial (e.g., a mechanical marker, e.g., a marker fixed to the patient, e.g., attached to target anatomy, e.g., attached to a vertebra)) (e.g., dynamically re-register the patient position upon detected proximity of the end effector, or the surgical instrument, or a portion or component of the surgical instrument or end effector, with a pre-planned fiducial (e.g., a mechanical marker, e.g., a marker fixed to the patient, e.g., attached to target anatomy, e.g., attached to a vertebra)) (e.g., dynamically re-register the patient position based upon the updated position of the end effector determined upon operator command, e.g., surgeon pressing a button or otherwise activating a graphical or tactile user interface when a re-registered representation is desired)]; (vi) graphically render the re-registered patient position for viewing on the display (e.g., graphically render the updated 3D graphical representation); and (vii) dynamically determine a force feedback to deliver via the force feedback subsystem (e.g., to an operator of the robotic arm during the surgical procedure) based at least in part on the re-registered patient position [(e.g., based at least on the updated 3D representation of the patient situation and a current position of the end effector (and/or the surgical instrument) (e.g., subject to predetermined go/no-go zones) (e.g., thereby permitting, facilitating, directing (e.g., imposing a haptic detent or well), inhibiting (e.g., imposing a speed constraint), and/or disallowing movement of the surgical instrument in go/no-go zones, e.g., by direct manipulation of the surgical instrument by the operator, e.g., surgeon)].

In another aspect, the disclosed technology includes a method of registering a patient's anatomy with an instrument attached to an end-effector of a robotic arm of a robotic surgical system, the method including the steps of: receiving, by a processor of a computing device, haptic feedback, from a force sensor attached directly or indirectly to the robotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determining, by the processor, a set of spatial coordinates, wherein the set of spatial coordinates includes a spatial coordinate for each contact of the instrument with the material, expressed using a robot coordinate system, (e.g., relative to the position of the end-effector), wherein each spatial coordinate corresponds to a point on the surface of an anatomical volume (e.g., a point on a surface of a bone); receiving, by the processor, a set of medical image data coordinates expressed using a medical image data coordinate system that correspond to a patient anatomy surface (e.g., determined from tomographic patient data (e.g., CT data, Mill data)); mapping, by the processor, (e.g., using surface matching) the surface corresponding to the set of spatial coordinates to the patient anatomy surface corresponding to the set of medical image data coordinates (e.g., by generating a transformation array or transformation matrix); generating, by the processor, a coordinate mapping between the robot coordinate system and the medical image data coordinate system based on the mapping between the surface corresponding to the set of spatial coordinates and the surface corresponding to the set of medical image data coordinates; and storing, by the processor, the coordinate mapping, thereby registering the patient's anatomy (e.g., for navigational use by a surgeon during a surgical procedure).

In certain embodiments, the method includes the step of: outputting, by the processor rendering data for display (e.g., on a display of the robotic surgical system; e.g., on a display on the robotic arm), wherein the rendering data corresponds to a representation of a position of a member and at least a portion of the medical image data based on the coordinate mapping, wherein the member is selected from the group consisting of: the end-effector, the instrument, and a surgical instrument.

In certain embodiments, the method includes the steps of: generating, by the processor, new rendering data by modifying the rendering data based on a change in the end-effector's position; and outputting, by the processor, the new rendering data for display.

In certain embodiments, a fiducial marker includes the material (e.g., the end-effector contacts a fiducial marker with known size and shape such that the spatial coordinate is determined using a spatial relationship between the fiducial marker and the patient's anatomy).

In certain embodiments, the robotic arm is active and non-back drivable.

In certain embodiments, the robotic surgical system includes the processor.

In certain embodiments, the method includes storing, by the processor, a patient anatomy model wherein the patient anatomy model is defined by the patient anatomy surface expressed in the robot coordinate system.

In one aspect, the disclosed technology includes a robotic surgical system for registering a patient's anatomy with an instrument attached to an end-effector of a robotic arm of the robotic surgical system, the system including: a robotic arm with amend-effector having an instrument attached thereto; a force sensor attached directly or indirectly to the robotic arm (e.g., the force sensor located between the instrument and the robotic arm); and a processor and a memory having instructions stored thereon, wherein the instructions, when executed by the processor, cause the processor to: receive haptic feedback, from the force sensor, prompted by movement of the end-effector (e.g., towards a patient); determine that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determine a set of spatial coordinates, wherein the set of spatial coordinates includes a spatial coordinate for each contact of the instrument with the material, expressed using a robot coordinate system, (e.g., relative to the position of the end-effector), wherein each spatial coordinate corresponds to a point on the surface of an anatomical volume (e.g., a point on a surface of a bone); determine a set of medical image data coordinates expressed using a medical image data coordinate system that correspond to a patient anatomy surface (e.g., determined from tomographic patient data (e.g., CT data, Mill data)); map (e.g., using surface matching) the surface corresponding to the set of spatial coordinates to the patient anatomy surface corresponding to the set of medical image data coordinates (e.g., by generating a transformation array or transformation matrix); generate a coordinate mapping between the robot coordinate system and the medical image data coordinate system based on the mapping between the surface corresponding to the set of spatial coordinates and the surface corresponding to the set of medical image data coordinates; and store the coordinate mapping, thereby registering the patient's anatomy (e.g., for navigational use by a surgeon during a surgical procedure).

In certain embodiments, the instructions, when executed by the processor, cause the processor to: output rendering data for display (e.g., on a display of the robotic surgical system; e.g., on a display on the robotic arm), wherein the rendering data corresponds to a representation of a position of a member and at least a portion of the medical image data based on the coordinate mapping, wherein the member is selected from the group consisting of: the end-effector, the instrument, and a surgical instrument.

In certain embodiments, the instructions, when executed by the processor, cause the processor to: generate new rendering data by modifying the rendering data based on a change in the end-effector's position; and output the new rendering data for display.

In certain embodiments, a fiducial marker includes the material (e.g., the end-effector contacts a fiducial marker with known size and shape such that the spatial coordinate is determined using a spatial relationship between the fiducial marker and the patient's anatomy).

In certain embodiments, the robotic arm is active and non-back drivable.

In certain embodiments, the robotic surgical system includes the processor.

In certain embodiments, the instructions, when executed by the processor, cause the processor to: store a patient anatomy model wherein the patient anatomy model is defined by the patient anatomy surface expressed in the robot coordinate system.

In one aspect, the disclosed technology includes a method of updating a model of a patient's anatomy after volume removal with an instrument attached to an end-effector of a robotic arm of a robotic surgical system, the method including the steps of: receiving, by a processor of a computing device, haptic feedback, from a force sensor attached directly or indirectly to therobotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determining, by the processor, a set of spatial coordinates, wherein the set of spatial coordinates includes a spatial coordinate for each contact of the instrument with the material, expressed using a robot coordinate system (e.g., relative to the position of the end-effector), wherein each spatial coordinate corresponds to a point on the surface of an anatomical volume (e.g., a point on a surface of a bone); receiving, by the processor, a set of medical image data coordinates that correspond to the surface of a volume of the patient's anatomy, wherein each medical image data coordinate in the set of medical image data coordinates is expressed using a medical image data coordinate system; receiving, by the processor, a coordinate mapping between the robot coordinate system and the medical image data coordinate system (e.g., a transformation array or transformation matrix); determining, by the processor, one or more interior spatial coordinates in the set of spatial coordinates that correspond to points inside the surface of the volume of the patient's anatomy based on the set of medical image data coordinates and the coordinate mapping; generating, by the processor, a set of interior medical image data coordinates, wherein the set of interior medical image data coordinates includes an interior medical image data coordinate for each of the one or more interior spatial coordinates using the coordinate mapping; modifying, by the processor, the set of medical image data coordinates that define the surface of the volume of the patient's anatomy with the set of interior medical image data coordinates such that a first volume defined by the set of medical image data coordinates is larger than a second volume defined by the modified set of medical image data coordinates; and storing, by the processor, the modified set of medical image data coordinates (e.g., for displaying to a surgeon), thereby updating the model of the patient's anatomy.

In one aspect, the disclosed technology includes a system for updating a model of a patient's anatomy after volume removal with an instrument attached to an end-effector of a robotic arm of a robotic surgical system, the system including: a robotic arm with an end-effector having an instrument attached thereto; a force sensor attached directly or indirectly to the robotic arm (e.g., the force sensor located between the instrument and the robotic arm); and a processor and a memory having instructions stored thereon, wherein the instructions, when executed by the processor, cause the processor to: receive haptic feedback, from the force sensor, prompted by movement of the end-effector (e.g., towards a patient); determine that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determine a set of spatial coordinates, wherein the set of spatial coordinates includes a spatial coordinate for each contact of the instrument with the material, expressed using a robot coordinate system (e.g., relative to the position of the end-effector), wherein each spatial coordinate corresponds to a point on the surface of an anatomical volume (e.g., a point on a surface of a bone); receive a set of medical image data coordinates that correspond to the surface of a volume of the patient's anatomy, wherein each medical image data coordinate in the set of medical image data coordinates is expressed using a medical image data coordinate system; receive a coordinate mapping between the robot coordinate system and the medical image data coordinate system (e.g., a transformation array or transformation matrix);determine one or more interior spatial coordinates in the set of spatial coordinates that correspond to points inside the surface of the volume of the patient's anatomy based on the set of medical image data coordinates and the coordinate mapping; determine a portion of the volume of the patient's anatomy that has been removed using the one or more interior spatial coordinates; generate a set of interior medical image data coordinates, wherein the set of interior medical image data coordinates includes an interior medical image data coordinate for each of the one or more interior spatial coordinates using the coordinate mapping; modify the set of medical image data coordinates that define the surface of the volante of the patient's anatomy with the set of interior medical image data coordinates such that a first volume defined by the set of medical image data coordinates is larger than a second volume defined by the modified set of medical image data coordinates; and store the modified set of medical image data coordinates (e.g., for displaying to a surgeon), thereby updating the model of the patient's anatomy.

In one aspect, the disclosed technology includes a method of re-registration patient's anatomy during a surgical procedure with an instrument attached to an end-effector of a robotic arm of a robotic surgical system, the method including the steps of: receiving, by a processor of a computing device, haptic feedback, from a force sensor attached directly or indirectly to the robotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determining, by the processor, a set of spatial coordinates, wherein the set of spatial coordinates includes a spatial coordinate for each contact of the instrument with the material, expressed using the robot coordinate system (e.g., relative to the position of the end-effector), wherein each spatial coordinate corresponds to a point on the surface of an anatomical volume (e.g., a point on a surface of a bone); receiving, by the processor, a coordinate mapping between a robot coordinate system and a medical image data coordinate system (e.g., a transformation array or transformation matrix), wherein the robot coordinate system corresponds to a physical coordinate system of the end-effector; updating, by the processor, the coordinate mapping based on a mapping of the surface corresponding to the set of spatial coordinates; and storing, by the processor, the updated coordinate mapping (e.g., to provide an accurate navigational model for use by a surgeon during a surgical procedure), thereby re-registering the patient's anatomy, the mapping is generated using surface matching.

In certain embodiments, the updating step includes: determining, by the processor, a set of modeling coordinates, by converting, using the coordinate mapping, a set of medical image modeling coordinates defining the surface of a volume of a patient anatomy, wherein the set of modeling coordinates are expressed in the robot coordinate system and define an anticipated location of the surface of the volume, and the set of medical image modeling coordinates have been generated from medical imaging data; and mapping, by the processor, (e.g., using surface matching,) the surface corresponding to the set of spatial coordinates to the patient anatomy surface corresponding to the set of modeling coordinates (e.g., by generating a transformation array or transformation matrix); and updating, by the processor, the coordinate mapping based on the mapping of the surface corresponding to the set of spatial coordinates to the set of modeling coordinates.

In certain embodiments, the updating step includes: receiving, by the processor, a set of modeling coordinates, wherein the set of modeling coordinates are expressed in the robot coordinate system and define the surface of a volume of a patient anatomy; mapping, by the processor, (e.g., using surface matching,) the surface corresponding to the set of spatial coordinates to the patient anatomy surface corresponding to the set of modeling coordinates (e.g., by generating a transformation array or transformation matrix); and updating, by the processor, the coordinate mapping based on the mapping of the surface corresponding to the set of spatial coordinates to the set of modeling coordinates.

In one aspect, the disclosed technology includes a system for re-registering a patient's anatomy during a surgical procedure with an instrument attached to an end-effector of a robotic arm of a robotic surgical system, the system including: a robotic arm with an end-effector having an instrument attached thereto; a force sensor attached directly or indirectly to the robotic arm (e.g., the force sensor located between the instrument and the robotic arm); and a processor and a memory having instructions stored thereon, wherein the instructions, when executed by the processor, cause the processor to: receive haptic feedback, from the force sensor, prompted by movement of the end-effector (e.g., towards a patient); determine that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determine a set of spatial coordinates, wherein the set of spatial coordinates includes a spatial coordinate for each contact of the instrument with the material, expressed using the robot coordinate system (e.g., relative to the position of the end-effector), wherein each spatial coordinate corresponds to a point on the surface of an anatomical volume (e.g., a point on a surface of a bone); receive a coordinate mapping between a robot coordinate system and a medical image data coordinate system (e.g., a transformation array or transformation matrix), wherein the robot coordinate system corresponds to a physical coordinate system of the end-effector; update the coordinate mapping based on a mapping of the surface corresponding to the set of spatial coordinates; and store the updated coordinate mapping (e.g., to provide an accurate navigational model for use by a surgeon during a surgical procedure), thereby re-registering the patient's anatomy.

In certain embodiments, the mapping is generated using surface matching.

In certain embodiments, the updating step includes instructions that, when executed by the processor, cause the processor to: determine a set of modeling coordinates, by converting, using the coordinate mapping, a set of medical image modeling coordinates defining the surface of a volume of a patient anatomy, wherein: the set of modeling coordinates are expressed in the robot coordinate system and define an anticipated location of the surface of the volume, and the set of medical image modeling coordinates have been generated from medical imaging data; and map (e.g., using surface matching,) the surface corresponding to the set of spatial coordinates to the patient anatomy surface corresponding to the set of modeling coordinates (e.g., by generating a transformation array or transformation matrix); and update the coordinate mapping based on the mapping of the surface corresponding to the set of spatial coordinates to the set of modeling coordinates.

In certain embodiments, the updating step includes instructions that, when executed by the processor, cause the processor to: receive a set of modeling coordinates, wherein the set of modeling coordinates are expressed in the robot coordinate system and define the surface of a volume of a patient anatomy; map (e.g., using surface matching,) the surface corresponding to the set of spatial coordinates to the patient anatomy surface corresponding to the set of modeling coordinates (e.g., by generating a transformation array or transformation matrix); and update the coordinate mapping based on the mapping of the surface corresponding to the set of spatial coordinates to the set of modeling coordinates.

In one aspect, the disclosed technology includes a method of defining an operational volume in which a surgical instrument attached to an end-effector of a robotic arm of a robotic surgical system can be maneuvered, the method including the steps of: receiving, by a processor of a computing device, haptic feedback, from a force sensor attached directly or indirectly to the robotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determining, by the processor, a set of spatial coordinates, wherein the set of spatial coordinates includes a spatial coordinate for each contact of the instrument with the material, expressed using a robot coordinate system (e.g., relative to the position of the end-effector), wherein each spatial coordinate corresponds to a point on the surface of a volume (e.g., a point on a surface of a bone); receiving, by the processor, a model volume selected by a user (e.g., a model of a portion of bone to be removed), wherein the model volume is expressed in a robot coordinate system; mapping, by the processor, the surface of the model volume to the set of spatial coordinates; generating, by the processor, an updated model volume, wherein coordinates of the updated model volume are generated by converting coordinates of the model volume using the mapping of the surface of the model volume to the set of spatial coordinates; and storing, by the processor, the updated model volume.

In certain embodiments, the updated model volume is a constrained operational volume, wherein a terminal point of the surgical instrument is temporarily constrained to within the constrained operational volume.

In certain embodiments, the model volume is generated from medical image data using a coordinate mapping.

In certain embodiments, the method includes receiving, by the processor, the updated model volume (e.g., a model of a portion of bone to be removed), wherein the stored model volume is expressed in a first robot coordinate system; receiving, by the processor, an updated coordinate mapping expressed in a second robot coordinate system; mapping, by the processor, the first robot coordinate system to the second robot coordinate system; generating, by the processor, a second updated model volume by converting coordinates of the updated model volume to updated coordinates expressed in the second robot coordinate system using the mapping between the first robot coordinate system and the second robot coordinate system; and storing, by the processor, the second updated model volume.

In one aspect, the disclosed technology includes a system for defining an operational volume in which a surgical instrument attached to an end-effector of a robotic arm of a robotic surgical system can be maneuvered, the system including: a robotic arm with an end-effector having an instrument attached thereto; a force sensor attached directly or indirectly to the robotic arm (e.g., the force sensor located between the instrument and the robotic arm); and a processor and a memory having instructions stored thereon, wherein the instructions, when executed by the processor, cause the processor to: receive haptic feedback, from the force sensor, prompted by movement of the end-effector (e.g., towards a patient); determine that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determine a set of spatial coordinates, wherein the set of spatial coordinates includes a spatial coordinate for each contact of the instrument with the material, expressed using a robot coordinate system (e.g., relative to the position of the end-effector), wherein each spatial coordinate corresponds to a point on the surface of a volume (e.g., a point on a surface of a bone); receive a model volume selected by a user (e.g., a model of a portion of bone to be removed), wherein the model volume is expressed in a robot coordinate system; map the surface of the model volume to the set of spatial coordinates; generate an updated model volume, wherein coordinates of the updated model volume are generated by converting coordinates of the model volume using the mapping of the surface of the model volume to the set of spatial coordinates; and store the updated model volume.

In certain embodiments, the updated model volume is a constrained operational volume, wherein a terminal point of the surgical instrument is temporarily constrained to within the constrained operational volume.

In certain embodiments, the model volume is generated from medical image data using a coordinate mapping.

In certain embodiments, the instructions, when executed by the processor, cause the processor to: receive the updated model volume (e.g., a model of a portion of bone to be removed), wherein the stored model volume is expressed in a first robot coordinate system; receive an updated coordinate mapping expressed in a second robot coordinate system; map the first robot coordinate system to the second robot coordinate system; generate a second updated model volume by converting coordinates of the updated model volume to updated coordinates expressed in the second robot coordinate system using the mapping between the first robot coordinate system and the second robot coordinate system; and store the second updated model volume.

In one aspect, the disclosed technology includes a method of displaying a position of a surgical instrument attached to a robotic arm relative to a patient anatomy for navigation during a robotically-assisted surgical procedure, the method including: receiving, by a processor of a computing device, a location of a terminal point of the surgical tool (e.g., wherein the location of the terminal point is determined, by the processor, using a known (e.g., stored) distance between a location of the robotic arm and the terminal point), wherein the location is expressed in a robot coordinate system; receiving, by the processor, a coordinate mapping between the robot coordinate system and a medical image data coordinate system (e.g., a transformation array or transformation matrix); converting, by the processor, using the coordinate mapping, the location of the terminal point, such that the converted location of the terminal point is expressed in a medical image data coordinate system; generating, by the processor, rendering data including the converted location of the terminal point; and outputting, by the processor, the rendering data, wherein a display of the rendering data includes a representation of the patient anatomy and a representation of the location of the terminal point, wherein a simulated distance between a point on the representation of the patient anatomy and the representation of the terminal point is proportional to a spatial distance between the terminal point and the corresponding point on the patient's anatomy.

In certain embodiments, the rendering data corresponding to the representation of the patient anatomy is generated from medical image data coordinates generated from medical imaging data, wherein the medical image data coordinates are expressed in the medical image data coordinate system.

In one aspect, the disclosed technology includes a system of displaying a position of a surgical instrument attached to a robotic arm relative to a patient anatomy for navigation during a robotically-assisted surgical procedure, the system including: a robotic arm with an end-effector having an instrument attached thereto; a force sensor attached directly or indirectly to the robotic arm (e.g., the force sensor located between the instrument and the robotic arm); and a processor and a memory having instructions stored thereon, wherein the instructions, when executed by the processor, cause the processor to: receive a location of a terminal point of the surgical tool (e.g., wherein the location of the terminal point is determined, by the processor, using a known (e.g., stored) distance between a location of the robotic arm and the terminal point), wherein the location is expressed in a robot coordinate system; receive a coordinate mapping between the robot coordinate system and a medical image data coordinate system (e.g., a transformation array or transformation matrix); convert, using the coordinate mapping, the location of the terminal point, such that the converted location of the terminal point is expressed in a medical image data coordinate system; generate rendering data including the converted location of the terminal point; output the rendering data, wherein a display of the rendering data includes a representation of the patient anatomy and a representation of the location of the terminal point, wherein a simulated distance between a point on the representation of the patient anatomy and the representation of the terminal point is proportional to a spatial distance between the terminal point and the corresponding point on the patient's anatomy.

In certain embodiments, the rendering data corresponding to the representation of the patient anatomy is generated from medical image data coordinates generated from medical imaging data, wherein the medical image data coordinates are expressed in the medical image data coordinate system.

In one aspect, the disclosed technology includes a method of performing volume removal surgery with one or more instruments, wherein the one or more instruments used by attaching to an end-effector of a robotic arm of a robotic surgical system, the method including the steps of: registering a patient's anatomy to express a model of the patient's anatomy in a robot coordinate system; contacting, following removal of a first volume of the patient's anatomy, an instrument attached to the end-effector to the patient's anatomy in a plurality of locations, wherein contact is determined by haptic feedback from a force sensor attached directly or indirectly to the robotic arm, wherein the haptic feedback is prompted by movement of the end-effector (e.g., towards a patient); updating the model of the patient's anatomy by determining a portion of the model that corresponds to the first volume of the patient's anatomy that has been removed using spatial coordinates corresponding to the plurality of locations contacted; optionally, re-registering the patient's anatomy by contacting a plurality of re-registration locations with the instrument, wherein contact is determined by haptic feedback from a force sensor attached directly or indirectly to the robotic arm, wherein the haptic feedback is prompted by movement of the end-effector (e.g., towards a patient), and coordinates in the model of the patient's anatomy are converted such that they are expressed in a new robot coordinate system based on the re-registration; defining an operational volume, wherein the operational volume is expressed in either the robot coordinate system or the new robot coordinate system (e.g., if the re-registration step is performed); and maneuvering the robotic arm such that a pre-defined terminal point on a surgical instrument is constrained to within the operational volume for a period of time during a second volume removal.

In certain embodiments, the registering step includes: receiving, by a processor of a computing device, haptic feedback, from a force sensor attached directly or indirectly to the robotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determining, by the processor, a set of spatial coordinates, wherein the set of spatial coordinates includes a spatial coordinate for each contact of the instrument with the material, expressed using the robot coordinate system, (e.g., relative to the position of the end-effector), wherein each spatial coordinate corresponds to a point on the surface of an anatomical volume (e.g., a point on a surface of a bone); receiving, by the processor, a set of medical image data coordinates expressed using a medical image data coordinate system that correspond to a patient anatomy surface (e.g., determined from tomographic patient data (e.g., CT data, MM data)); mapping, by the processor, (e.g., using surface matching,) the surface corresponding to the set of spatial coordinates to the patient anatomy surface corresponding to the set of medical image data coordinates (e.g., by generating a transformation array or transformation matrix); generating, by the processor, a coordinate mapping between the robot coordinate system and the medical image data coordinate system based on the mapping between the surface corresponding to the set of spatial coordinates and the surface corresponding to the set of medical image data coordinates; and storing, by the processor, the coordinate mapping (e.g., for navigational use by a surgeon during a surgical procedure).

In certain embodiments, the method including the step of: outputting, b y the processor, rendering data for display, wherein the rendering data corresponds to a representation of a member's position and at least a portion of the medical image data based on the coordinate mapping, wherein the member is selected from the group consisting of: the end-effector, the instrument, and a surgical instrument. In certain embodiments, the method including the steps of: generating, by the processor, new rendering data by modifying the rendering data based on a change in the end-effector's position; and outputting, by the processor, the new rendering data for display.

In certain embodiments, a fiducial marker includes the material (e.g., the end-effector contacts a fiducial marker with known size and shape such that the spatial coordinate is determined using a spatial relationship between the fiducial marker and the patient's anatomy).

In certain embodiments, the robotic arm is active and non-back drivable.

In certain embodiments, therobotic surgical system includes the processor.

In certain embodiments, the method includes storing, by the processor, a patient anatomy model wherein the patient anatomy model is defined by the patient anatomy surface expressed in the robot coordinate system.

In certain embodiments, the updating step includes: determining, by the processor, a set of spatial coordinates, wherein the set of spatial coordinates includes a spatial coordinate for each contact of the instrument with the material, expressed using a robot coordinate system (e.g., relative to the position of the end-effector), wherein each spatial coordinate corresponds to a point on the surface of an anatomical volume (e.g., a point on a surface of a bone); receiving, by the processor, a set of medical image data coordinates that correspond to the surface of a volume of the patient's anatomy, wherein each medical image data coordinate in the set of medical image data coordinates is expressed using a medical image data coordinate system; receiving, by the processor, a coordinate mapping between the robot coordinate system and the medical image data coordinate system (e.g., a transformation array or transformation matrix); determining, by the processor, one or more interior spatial coordinates in the set of spatial coordinates that correspond to points inside the surface of the volume of the patient's anatomy based on the set of medical image data coordinates and the coordinate mapping; determining, by the processor, a portion of the volume of the patient's anatomy that has been removed using the one or more interior spatial coordinates; generating, by the processor, a set of interior medical image data coordinates, wherein the set of interior medical image data coordinates includes an interior medical image data coordinate for each of the one or more interior spatial coordinates using the coordinate mapping; modifying, by the processor, the set of medical image data coordinates that define the surface of the volume of the patient's anatomy with the set of interior medical image data coordinates such that first volume defined by the set of medical image data coordinates is larger than second volume defined by the modified set of medical image data coordinates; and storing, by the processor, the modified set of medical image data coordinates (e.g., for displaying to a surgeon).

In certain embodiments, the defining step includes: receiving, by a processor of a computing device, haptic feedback, from a force sensor attached directly or indirectly to the robotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrwnent) (e.g., wherein the material is bone); determining, by the processor, a set of spatial coordinates, wherein the set of spatial coordinates includes a spatial coordinate for each contact of the instrwnent with the material, expressed using a robot coordinate system (e.g., relative to the position of the end-effector), wherein each spatial coordinate corresponds to a point on the surface of a volume (e.g., a point on a surface of a bone); receiving, by the processor, a model volume selected by a user (e.g., a model of a portion of bone to be removed), wherein the model volume is expressed in a robot coordinate system; mapping, by the processor, the surface of the model volume to the set of spatial coordinates; generating, by the processor, an updated model volume, wherein coordinates of the updated model volume are generated by converting coordinates of the model volume using the mapping of the surface of the model volume to the set of spatial coordinates; and storing, by the processor, the updated model volume.

In certain embodiments, the updated model volume is a constrained operational volume, wherein a terminal point of the surgical instrument is temporarily constrained to within the constrained operational volume.

In certain embodiments, the model volume is generated from medical image data using a coordinate mapping.

In certain embodiments, the method includes receiving, by the processor, the updated model volume (e.g., a model of a portion of bone to be removed), wherein the stored model volume is expressed in a first robot coordinate system; receiving, by the processor, an updated coordinate mapping expressed in a second robot coordinate system; mapping, by the processor, the first robot coordinate system to the second robot coordinate system; generating, by the processor, a second updated model volume by converting coordinates of the updated model volume to updated coordinates expressed in the second robot coordinate system using the mapping between the first robot coordinate system and the second robot coordinate system; and storing, by the processor, the second updated model volume.

In certain embodiments, the re-registering step includes: receiving, by a processor of a computing device, haptic feedback, from a force sensor attached directly or indirectly to the robotic arm, prompted by movement of the end-effector (e.g., towards a patient); determining, by the processor, that the haptic feedback corresponds to contact of the instrument with a material (e.g., having a certain density or certain mechanical properties) (e.g., based at least on a magnitude of the haptic feedback exceeding a threshold) (e.g., additionally based on the location of at least one point on the instrument) (e.g., wherein the material is bone); determining, by the processor, a set of spatial coordinates, wherein the set of spatial coordinates includes a spatial coordinate for each contact of the instrument with the material, expressed using the robot coordinate system (e.g., relative to the position of the end-effector), wherein each spatial coordinate corresponds to a point on the surface of an anatomical volume (e.g., a point on a surface of a bone); receiving, by the processor, a coordinate mapping between a robot coordinate system and a medical image data coordinate system (e.g., a transformation array or transformation matrix), wherein the robot coordinate system corresponds to a physical coordinate system of the end-effector; updating, by the processor, the coordinate mapping based on a mapping of the surface corresponding to the set of spatial coordinates; and storing, by the processor, the updated coordinate mapping (e.g., to provide an accurate navigational model for use by a surgeon during a surgical procedure).

In certain embodiments, the mapping is generated using surface matching.

In certain embodiments, the updating step includes: determining, by the processor, a set of modeling coordinates, by converting, using the coordinate mapping, a set of medical image modeling coordinates defining the surface of a volume of a patient anatomy, wherein the set of modeling coordinates are expressed in the robot coordinate system and define an anticipated location of the surface of the volume, and the set of medical image modeling coordinates have been generated from medical imaging data; and mapping, by the processor, (e.g., using surface matching,) the surface corresponding to the set of spatial coordinates to the patient anatomy surface corresponding to the set of modeling coordinates (e.g., by generating a transformation array or transformation matrix); and updating, by the processor, the coordinate mapping based on the mapping of the surface corresponding to the set of spatial coordinates to the set of modeling coordinates.

In certain embodiments, the updating step includes: receiving, by the processor, a set of modeling coordinates, wherein the set of modeling coordinates are expressed in the robot coordinate system and define the surface of a volume of a patient anatomy; mapping, by the processor, (e.g., using surface matching,) the surface corresponding to the set of spatial coordinates to the patient anatomy surface corresponding to the set of modeling coordinates (e.g., by generating a transformation array or transformation matrix); and updating, by the processor, the coordinate mapping based on the mapping of the surface corresponding to the set of spatial coordinates to the set of modeling coordinates.

In another aspect, the disclosed technology includes a method of updating an operational volume in which a surgical instrument attached to an end-effector of a robotic arm of a robotic surgical system can be maneuvered, the method including the steps of: receiving, by the processor, a stored model volume including coordinates (e.g., a model of a portion of bone to be removed), wherein the stored model volume is expressed in a first robot coordinate system; receiving, by the processor, an updated coordinate mapping expressed in a second robot coordinate system; converting, by the processor, each coordinate of the stored model volume to be expressed in the second robot coordinate system using the updated coordinate mapping; and storing, by the processor, an updated model volume including the converted coordinates.

In order for the present disclosure to be more readily understood, certain terms used herein are defined below. Additional definitions for the following terms and other terms may be set forth throughout the specification.

In this application, the use of "or" means "and/or" unless stated otherwise. As used in this application, the term "comprise" and variations of the term, such as "comprising"

and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, I3o/o, 12%, 11%, 10%, 9%,8%, 7%,6%,5%,4%, 3%, 2%, 1%, or less in either direction (greater than or less than) of the stated reference value unless otherwise stated or otherwise evident from the context (except where such number would exceed 100% of a possible value).

Mapping: As used herein, "mapping" refers to establishing a function between two sets of coordinates or data corresponding to two sets of coordinates. The function between the two sets may be discrete or continuous. A mapping allows coordinates recorded and/or stored in one coordinate system to be converted to coordinates in another coordinate system and vice versa. Two sets of coordinates expressed in the same coordinate system may be mapped with each other as well. A map or mapping may be stored on a computer readable medium as an array or matrix of data. In certain embodiments, a map or mapping is a linear transform stored as an array on a computer readable medium. In certain embodiments, the map or mapping is used to convert between coordinate systems. In certain embodiments, the coordinate systems are Cartesian. In some embodiments, at least one of the coordinate systems is non-Cartesian. A mapping may be an optimized function, wherein the mapping represents the function of minimal error or error below a threshold according to the mapping method (e.g., surface matching). In certain embodiments, mapping comprises surface matching. Herein, "a map" and "a mapping" are used interchangeably.

BRIEF DESCRIPTIONS OF THE DRAWINGS

Drawings are presented herein for illustration purposes, not for limitation. The foregoing and other objects, aspects, features, and advantages of the invention will become more apparent and may be better understood by referring to the following description taken in conjunction with the accompanying drawings, in which.

Figure 5C:
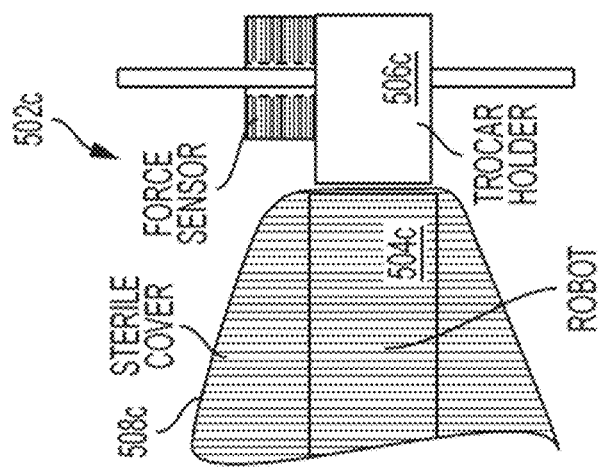
Figure 5B:
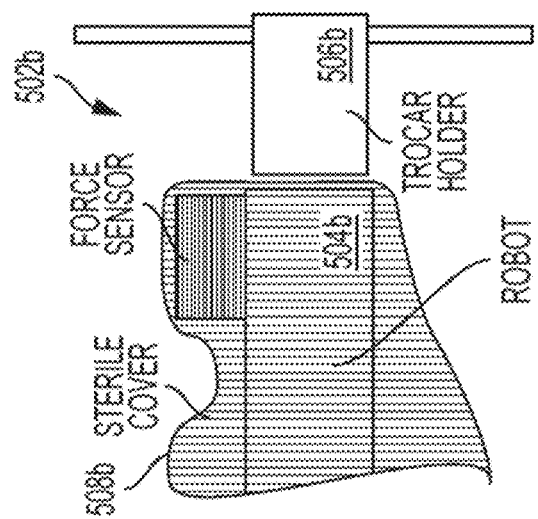
Figure 5A:
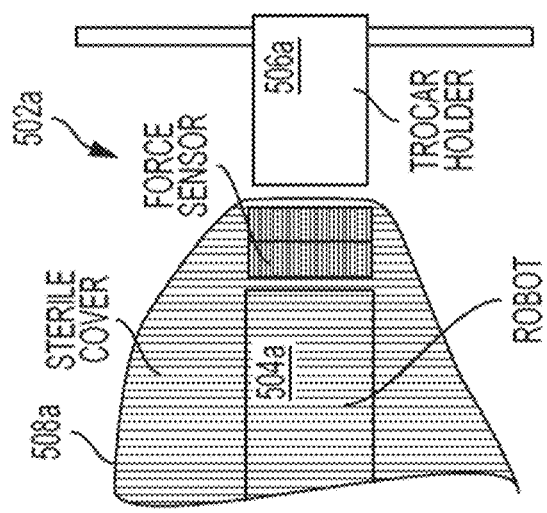
Figure 6:
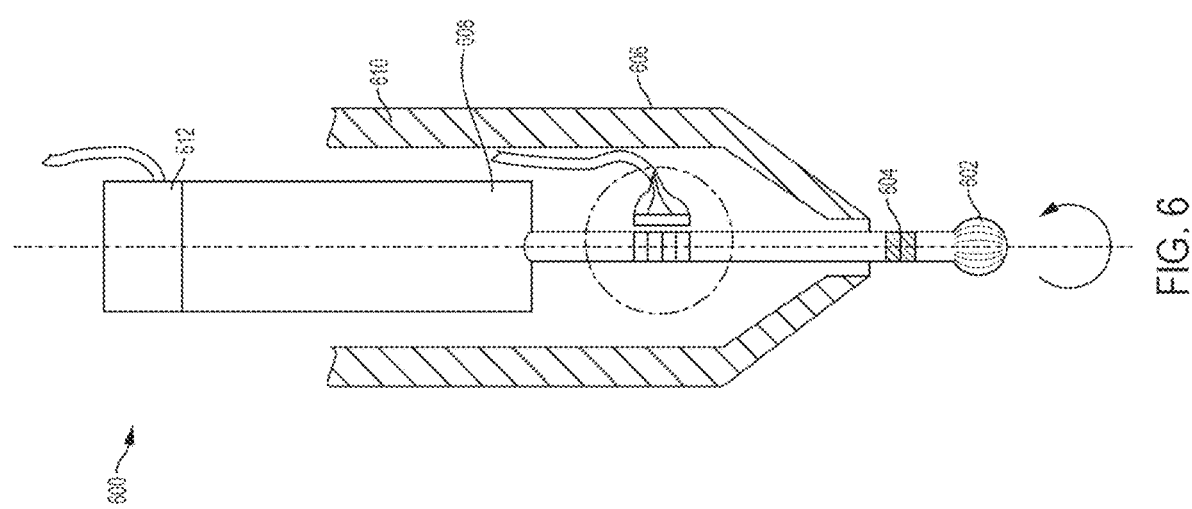
Figure 8:
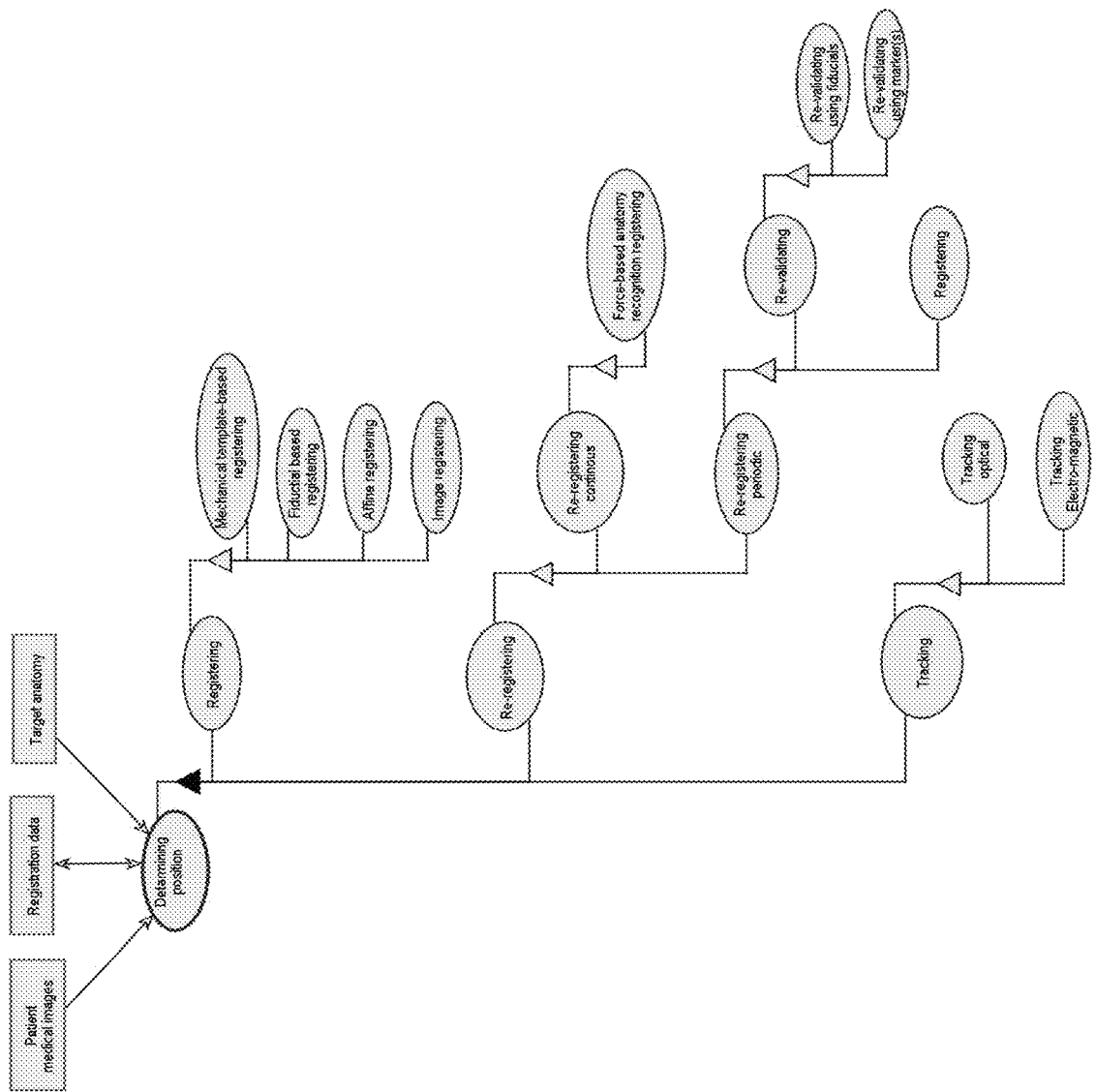
Figure 9:
Figure 10:
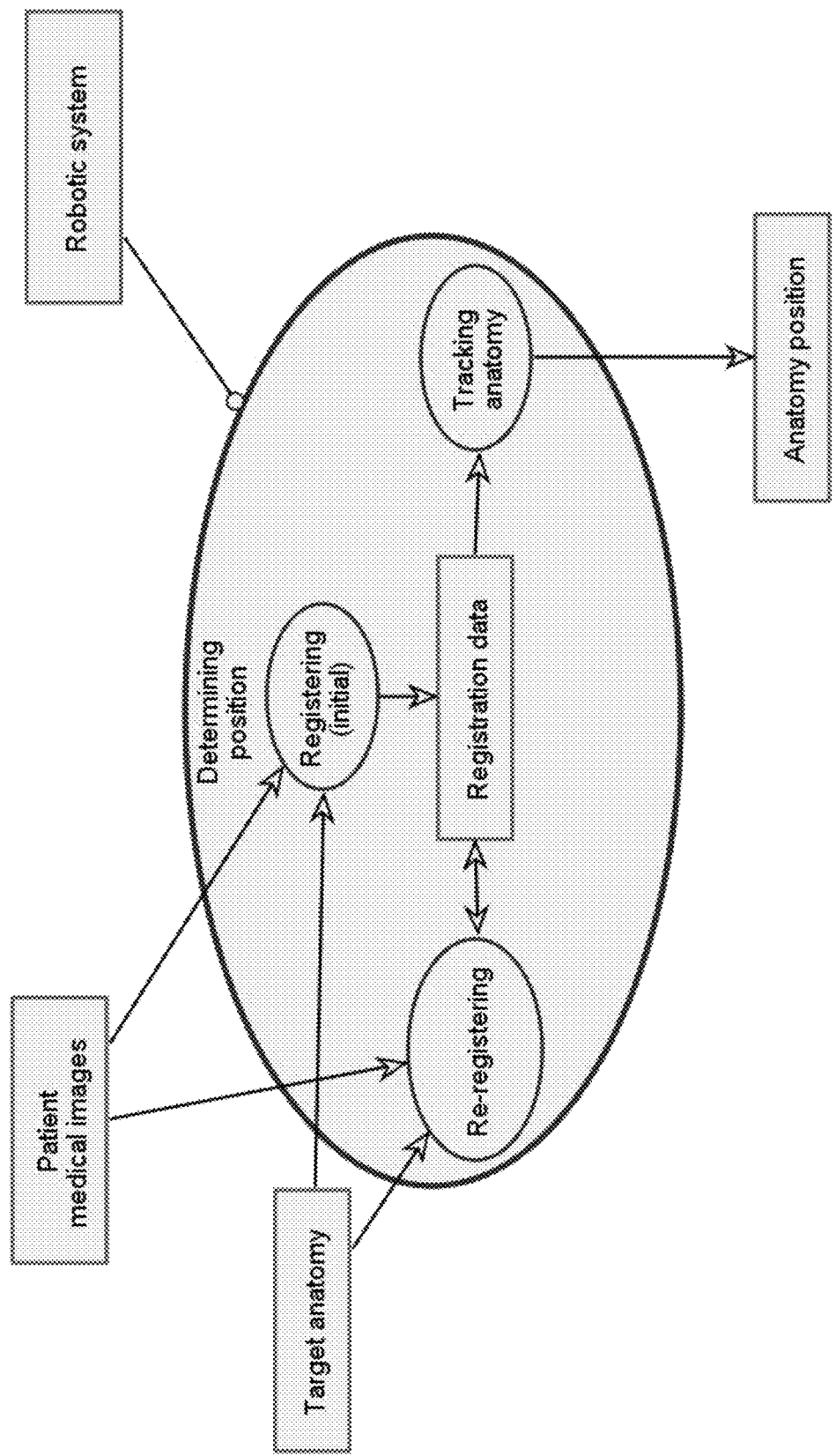
Figure 11:
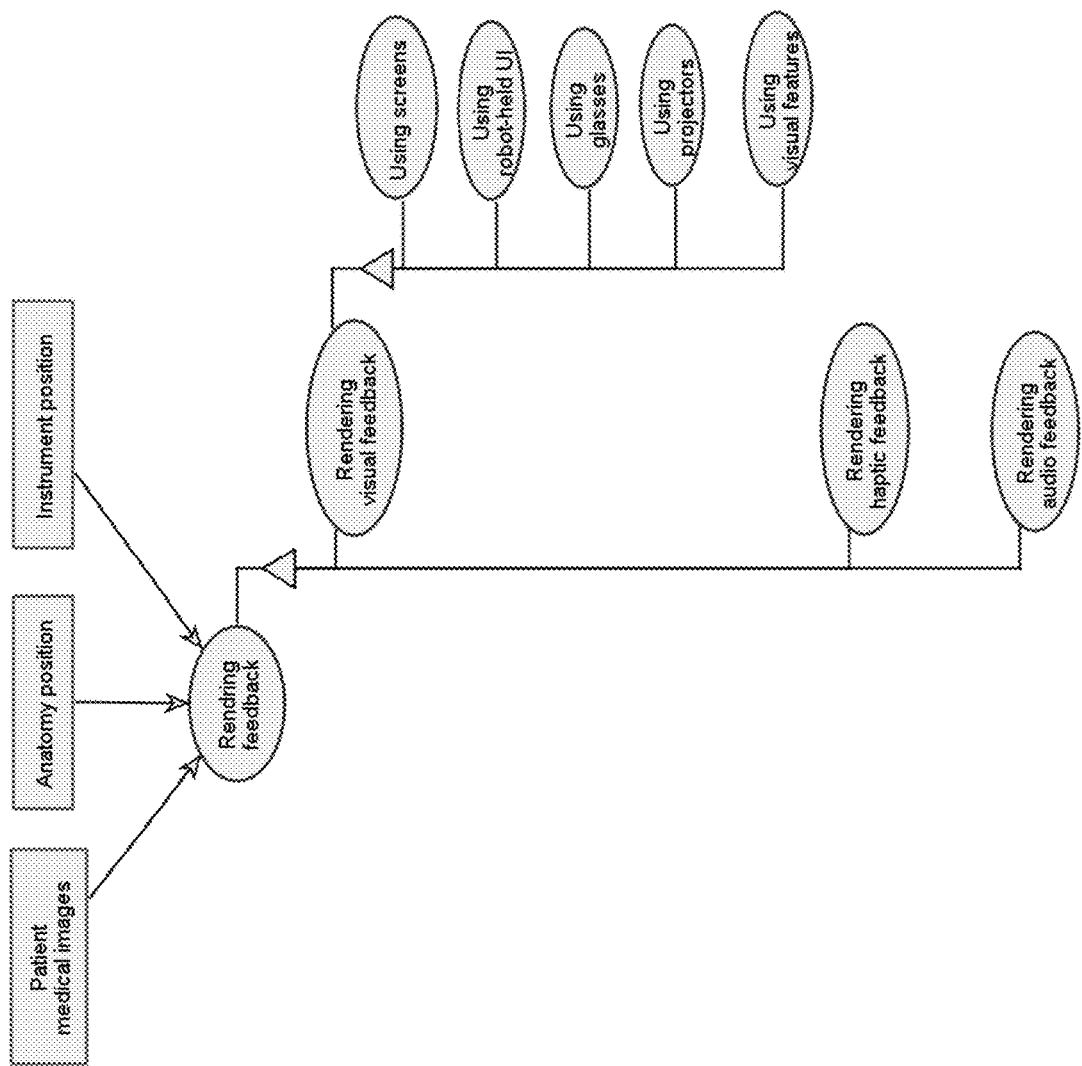
Figure 12:
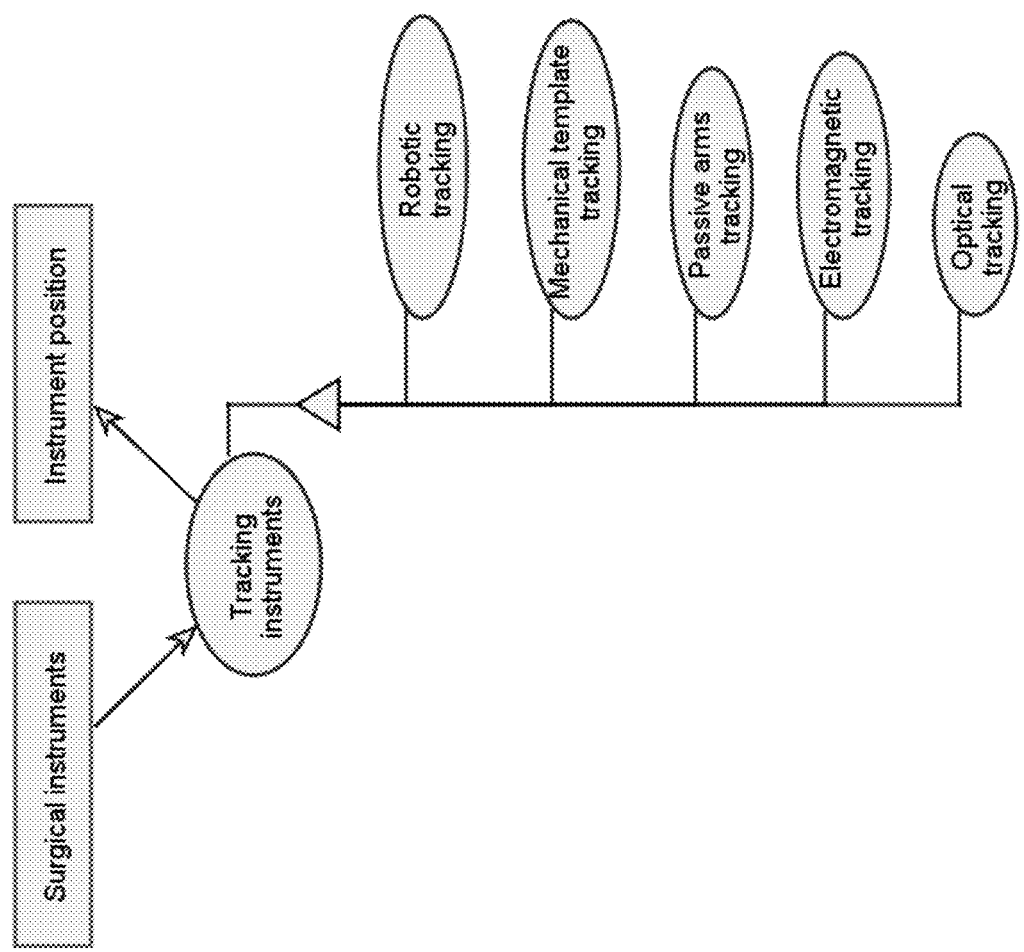
Figure 13:
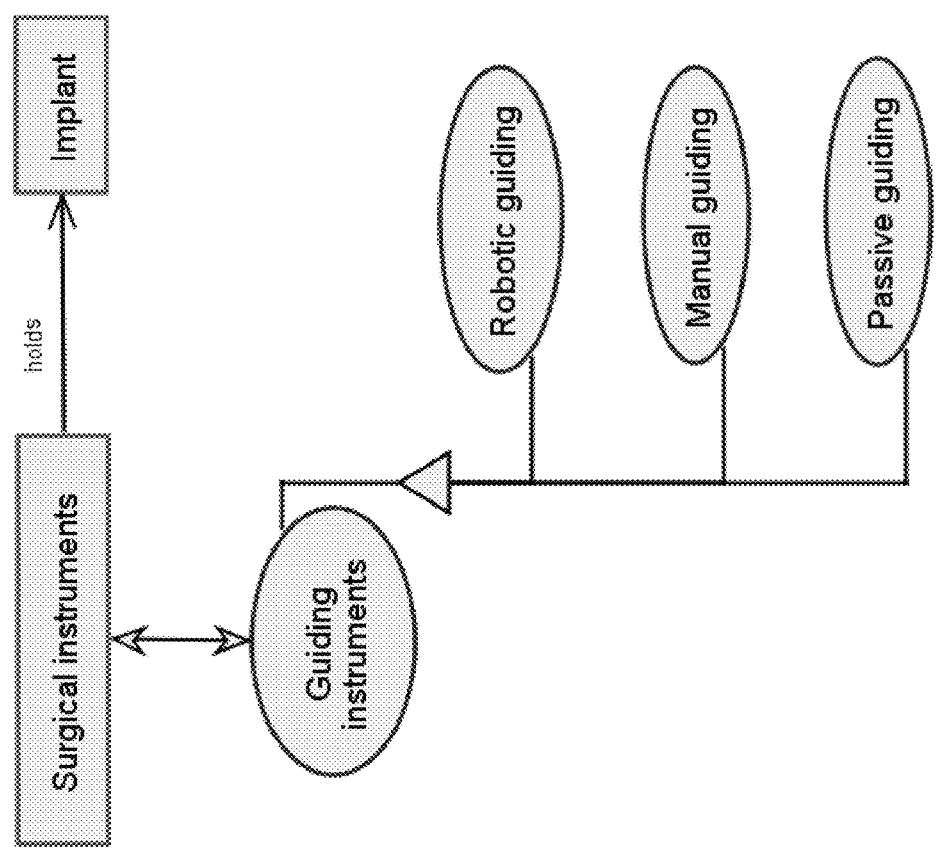

FIGS. 5A, 5B, and 5C are illustrations of force sensor implementations, according to illustrative embodiments of the invention;

FIG. 6 is an illustration of a surgical instrument, according to an illustrative embodiment of the invention;

FIGS. 7A through 7D are illustrations of implementations of a force sensor integrated in a surgical drill, according to an illustrative embodiment of the invention;

FIG. 8 is an illustration of a process for determining a position of a target anatomy, according to an illustrative embodiment of the invention;

FIG. 9 is an illustration of an example mechanical marker, according to an illustrative embodiment of the invention;

FIG. 10 is an illustration of a process for determining a position of a target anatomy based on automatic reregistration, according to an illustrative embodiment of the invention;

FIG. 11 is an illustration of a process for rendering feedback to an operator, according to an illustrative embodiment of the invention;

FIG. 12 is an illustration of a process for tracking an instrument, according to an illustrative embodiment of the invention;

FIG. 13 is an illustration of a process for guiding an instrument, according to an illustrative embodiment of the invention;

FIGS. 14 to 35 are illustrations of a patient's anatomy and a surgical robotic system during a method of performing a surgical procedure on the patient's spine using the robotic surgical system and robot navigation, according to an illustrative embodiment of the invention.

Figure 36:
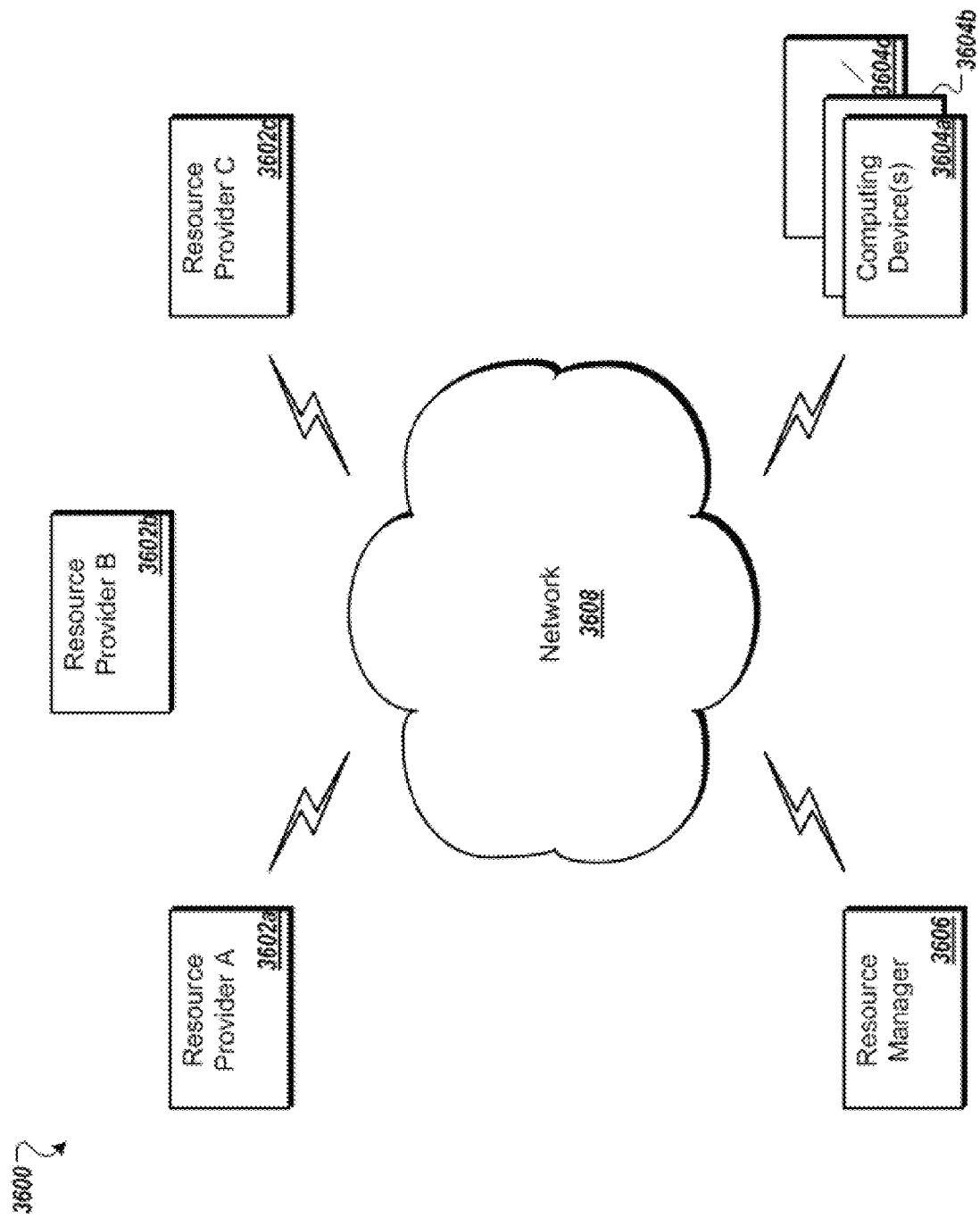
Figure 37:
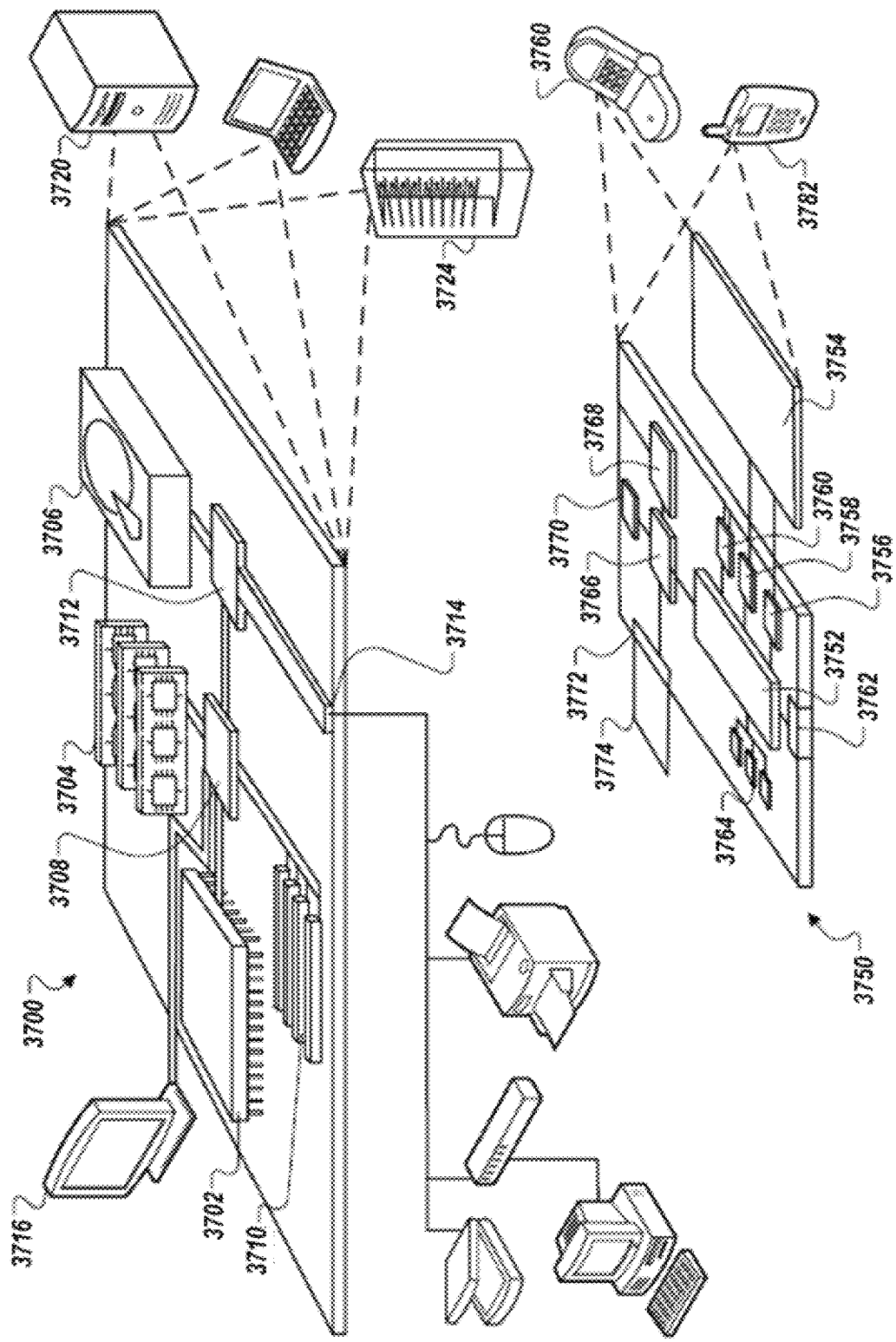

FIG. 36 illustrates a block diagram of an exemplary cloud computing environment, according to an illustrative embodiment of the invention;

FIG. 37 is a block diagram of a computing device and a mobile computing device, according to an illustrative embodiment of the invention; and FIG. 38 is an illustration of an example robotic surgical system, according to an illustrative embodiment of the invention.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Figure 1:
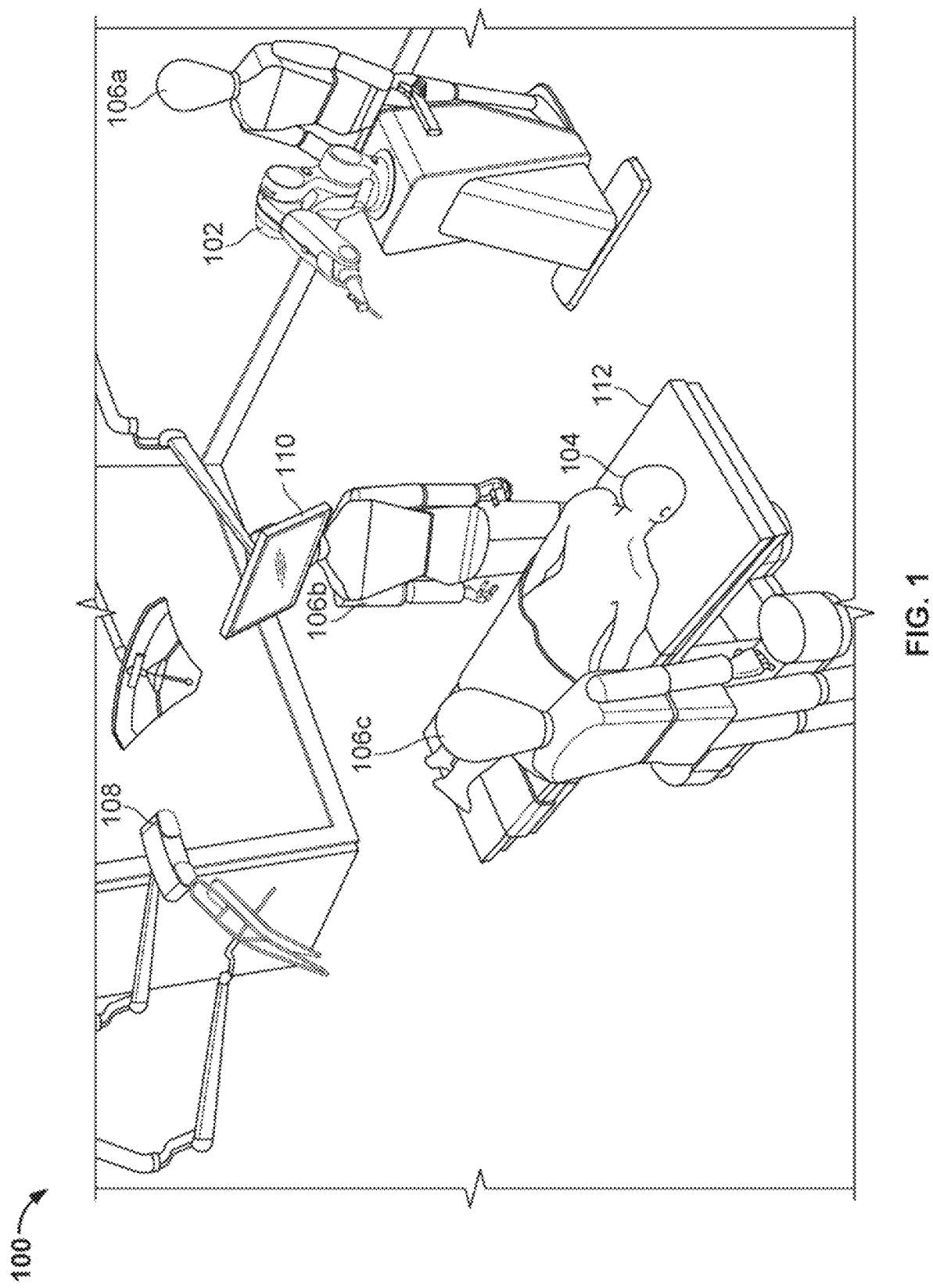
FIG. 1 is an illustration of a robotic surgical system in an operating room, according to an illustrative embodiment of the invention.

FIG. 1 illustrates an example robotic surgical system in an operating room 100. In some implementations, one or more surgeons, surgical assistants, surgical technologists and/or other technicians, (106a-c) perform an operation on a patient 104 using a robotic-assisted surgical system. In the operating room the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient. Once the robotic an is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a for aminotomy, a laminectomy, or a spinal fusion. In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

The mobile cart may permit a user (operator) 106a, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

For safety reasons, the mobile cart may be provided with a stabilization system that may be used during a surgical procedure performed with a surgical robot. The stabilization system increases the global stiffness of the mobile cart relative to the floor in order to ensure the accuracy of the surgical procedure. In some implementations, the wheels include a locking system that prevents the cart from moving. The stabilizing, braking, and/or locking system may be activated when the machine is turned on. In some implementations, the mobile cart includes multiple stabilizing, braking, and/or locking systems. In some implementations, the stabilizing system is electro-mechanical with electronic activation. The stabilizing, braking, and/or locking system(s) may be entirely mechanical. The stabilizing, braking, and/or locking system(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot I 02, and a display screen 110 that displays, for example, real time patient data and/or real time surgical robot trajectories.

In some implementations, a tracking detector 108 monitors the location of patient 104 and the surgical robot 102. The tracking detector may be a camera, a video camera, an infrared detector, field generator and sensors for electro-magnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector I08, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure. The disclosed technology includes a robot-based navigation system for real-time, dynamic re-registration of a patient position (e.g., position of vertebrae of a patient) during a procedure (e.g., surgical procedure, e.g., a spinal surgery). An example robotic surgical system is shown in FIG. 38. The robotic surgical system 3800 includes a robotic arm 3802. The robotic arm can have 3, 4, 5, 6, or 7 degrees of freedom. The robotic arm 3802 has an end effector 3804.

In certain embodiments, the robotic arm 3802 includes a position sensor 3806 for dynamically tracking a position of the end effector 3804 and/or surgical instrument during a surgical procedure. Additionally, one or more points of the surgical instrument can be dynamically tracked, for example, at a rate of at least 100 Hz, 250 Hz or greater, 500 Hz or greater, or 1000 Hz or greater (e.g., position determination per second).

In certain embodiments, the system 3800 includes a force feedback subsystem 3808. The force feedback subsystem 3808 can include sensor(s), actuator(s), controller(s), servo(s), and/or other mechanisms for delivering a haptic force to a user manipulating the end effector or a surgical instrument inserted in the instrument holder of the end effector. The force feedback subsystem 3808 can detect the resistive force caused by the surgical instrument contacting, moving against, penetrating, and/or moving within a tissue of the patient. Furthermore, the force feedback subsystem 3808 can distinguish between contacted tissue types (e.g., determining when contacted tissue meets or exceeds a threshold resistance, e.g., when the tissue is bone).

The force feedback subsystem 3808 can also detect a force delivered by the operator. For example, it can detect forces delivered by direct manipulation of the surgical instrument inserted in the surgical instrument holder of the end effector to cause movement of the surgical instrument and, therefore, the end effector. The force feedback subsystem 3808 can further distinguish between the force delivered by the operator and the resistive force caused by movement of the surgical instrument in relation to the tissue of the patient. This allows the operator to both apply forces to the system as well as feel resistance (e.g., via haptic feedback) as a surgical instrument contacts tissue in the patient. [0108] In certain embodiments, the robotic surgical system 3800 includes a display 3810 that is attached to, embedded within, or otherwise positioned in relation to the robotic arm being directly manipulated by the operator (e.g., surgeon) to allow for unimpeded visual feedback to the operator during the procedure.

When an operator uses the system, the system initially accesses (e.g., and graphically renders on the display) an initial registration of a target volume, such as a vertebra of the patient. This can be accomplished using medical images of the patient, including MRI, CT, X-rays, SPECT, ultrasound, or the like. These images can be obtained preoperatively or intraoperatively.

As the operative moves the position of the end effector, the position of the end effector is dynamically determined (e.g., by processor 3812). Specifically, in some implementations, the system dynamically determines a 3D position of one or more points of a surgical instrument.

Forces received by the surgical instrument are dynamically determined when the surgical instrument contacts, moves against, penetrates, and/or moves within the patient. The system can measure these forces and distinguish between contacted tissue types. This can be accomplished, for example, by determining when contacted tissue meets or exceeds a threshold resistance, such as when the tissue is bone). The system can further detect forces applied to the surgical instrument by the operator and distinguish between forces delivered by the operator and the resistive force caused by movement of the surgical instrument in relation to the tissue of the patient.

In certain embodiments, the system can dynamically re-register the patient position based at least in part on an updated position of the end effector determined by the position sensor. This can be used to update the 3D representation of the patient situation based at least in part on the updated position of the end effector when it is determined (e.g., via the force feedback subsystem) that the surgical instrument is in contact with a target anatomy. This can be accomplished using a surface matching algorithm keyed to the initial (or previous) registration.

For example, the system can dynamically re-register the patient position upon detected contact or proximity of the end effector, or the surgical instrument, or a portion or component of the surgical instrument or end effector, with a pre-planned fiducial, such as a mechanical marker, a marker fixed to the patient. Alternatively, the system can dynamically re-register the patient position based upon the updated position of the end effector determined upon operator command, such as the operator pressing a button or otherwise activating a graphical or tactile user interface when a re-registered representation is desired.

A surgical instrument holder can be connected to the end effector for insertion or attachment of a surgical instrument therein/thereto. The instrument holder can be removable. In such instances, attachment of the instrument holder to the end effector is precise and predictable such that it is always connected in the same position.

The robotic arm is designed to allow direct manipulation of a surgical instrument by an operator (e.g., by a surgeon) when the surgical instrument is inserted in/attached to the surgical instrument holder of the end effector. The manipulation of the instrument can be subject to haptic constraints based on the position of the end effector (and/or the surgical instrument) in relation to the patient. The surgical instrument has a known geometry and position in relation to the surgical instrument holder such that the location of the instrument (e.g., the tip of the instrument) is known by the robotic surgical system. For example, when a surgical instrument is fully inserted into the instrument holder, the position of the instrument is known to the robotic surgical system because the position of the end effector is known as well as information about the surgical instrument and the instrument holder.

In certain embodiments, a tool center point (TCP) facilitates precise positioning and trajectory planning for surgical instrument guides and surgical instruments inserted through or attached to the surgical instrument holder. Surgical instruments can be engineered such that when inserted into the surgical instrument holder, there is a defined tool center point with known coordinates relative to robotic arm. The origin of a coordinate system used to define the tool center point may be located at a flange of a robotic arm. It may additionally be located at any convenient to define point such as an interface, joint, or terminal aspect of a component of a robotic surgical system.

In certain embodiments, because the TCP is in a constant position relative to the robotic arm, regardless of whether a surgical guide or surgical instrument is being used with the surgical instrument holder, a surgeon can be provided visualization of the orientation, trajectory, and position of an instrument or instrument guide used with the surgical instrument holder. The use of engineered surgical instrument systems eliminates the need for navigation markers to be attached to the end of surgical guides or tools in order to precisely determine the position, orientation, and trajectory of a surgical instrument guide relative to a patient's anatomy.

Additionally, a navigation marker attached to surgical instrument holder can be used to track the position and orientation of the universal surgical instrument guide to update the position, orientation, and current trajectory based on manipulation of robotic arm by a surgeon. Additional information provided by patient imaging (e.g., CT data, radio imaging data, or similar) taken pre- or intra-operatively as well as navigation markers attached to a patient's body may be combined with data from a navigation marker attached to a universal surgical instrument guide and displayed on a screen viewable by the surgeon such that the surgeon can see the location of necessary features of the patient's anatomy and the position, trajectory, and orientation of a surgical instrument or surgical instrument guide relative to said anatomy.

FIGS. 5A-C illustrate example locations for mounting a force sensor (e.g., force/torque sensor 430). In some implementations, as shown in FIG. 5A, the force sensor 502 a is located between the tool holder 506 an and robot 504 a. Using this configuration, the sterile cover 508 a may be wrapped around the robot arm and between the force sensor and the tool holder to ensure sterilization. The force sensor 502 a may provide for direct measurement of forces (e.g., forces and/or torques) on the tool. The force sensor 502 a may be designed to resist flexing. The force sensor 502 a may be designed to flex under the stress of certain external forces. The displacement caused when an external force is applied may be calculated based on the force and/or torque applied to the tool, radial force stiffness, axial torque stiffness, and the diameter of the holder to which the tool is attached.

As shown in FIGS. 5B and 5C, respectively, the force sensor (e.g., 502 bin FIG. 5B or 502 c in FIG. 5C) may be located on the robot or the tool holder, respectively. These configurations may exclusively measure the forces and/or torques applied by the user. The force sensor 508 may be connected to the robot with an intermediary analog box which measures forces and torques and transmits them via a network (e.g., Ethernet, CAN, wireless, internet, private LAN, public LAN, etc.). Combinations of the above mentioned force sensor positions are possible to achieve predefined behavior (e.g. the first sensor in the base FIG. 5A and the second one in the handle FIG. 5B may be positioned to allow the feedback control system to decouple forces applied to the surgical tool from forces and/ortorque applied by a user).

Additionally, in some implementations the force sensor is integrated directly in the surgical instrument. For example, the force sensor may be integrated directly in the surgical drill bit as illustrated in FIG. 6. While the implementation of the force sensor 604 is described in relation to a drill bit 602 as shown in FIG. 6, the force sensor 604 may be similarly integrated in other surgical instruments. Integrating the force sensor 604 in a surgical instrument, such as a drill bit 602, may be more robust as it minimizes the impact of external disturbances for measuring forces applied to the drill bit.

In the example configuration shown in FIG. 6, the force sensor 604 is integrated in the shaft of the drill bit 602. The force sensor 604, in some implementations, is located on the drill bit 602 outside of the body 610 of the drill as shown in FIG. 6. In other implementations, the force sensor 604 is located inside the body 610 of the drill, thereby better protecting the force sensor 604 from external influences. Force sensor can have multiple degrees of freedom and measure, for example, 1 to 3 forces and/or l to 3 torques. Forces are transmitted from the rotating shaft through a connector 606. The connector, in some implementations, is one or more brushes that provide an electrical connection to the force sensor 604. If the force sensor is an optical sensor, the connector may be an optical transmitter (e.g. LED) and/or optical receiver (e.g., photodiode). In this example, the brushes contact the drill bit thereby forming an electrical connection with the force sensor 604. In some implementations, the brushes touch one or more contacts on the drill bit to form the electrical connection.

An electric or pneumatic motor 608 rotates the drill bit 602 shaft. In some implementations, a sensor 612 (e.g., an encoder) measures position of the shaft. The sensor 612 measures the position of the shaft in order to correlate forces measured by the force sensor to the relative position of the shaft. For example, if the force sensor is located in a drill bit, the measurement of the direction of the force will vary as the drill bit rotates. Specifically, the force sensor measures force and the direction of the force periodically (e.g., every millisecond, every microsecond, or somewhere therebetween). The drill bit rotates as the surgeon pushes it into bone. When the drill contacts the bone, the force sensor will indicate some force (F1) in a direction (D1). One period later (e.g., one millisecond), the drill bit will rotate slightly so the force sensor will indicate force of the same value (F1) (assuming a constant force is applied) in a different direction (D2). The direction of the force will continue to change relative to a single perspective as the drill bit rotates even if surgeon pushes into the bone with a constant force. A constantly changing force direction is not acceptable. In order to correlate the directions (e.g., D1, D2) with the global direction of the force (D) coming from the bone (seen by the surgeon, robotic system etc.) the position of the drill in the global space must be calculated as the drill bit rotates. The sensor 612 is used to measure the position of the shaft and thus determine the global direction of the force (D). The sensor 612 may be located on the back of the motor 608 as shown in FIG. 6. The sensor 612 may be located in other locations relative to the motor 608 as well. The force sensor 604 may be provided in various configurations as shown in FIGS. 7A-D. In each configuration, the goal is to measure forces on the tip of the tool (e.g., drill bit ultrasound bit, etc.). In the example shown in FIG. 7A the force sensor 604 is integrated in the shaft of the drill bit 602 as described in relation to FIG. 6. The force sensor 604 may communicate with a connector 606 (shown in FIG. 6) via a sensor cable 702. The sensor cable 702, in some implementations, is routed inside the drill bit 602. In some implementations, the connector 606 (shown in FIG. 6) is electrically connected to the sensor cable 702 via one or more connection pads.

Figure 7B:
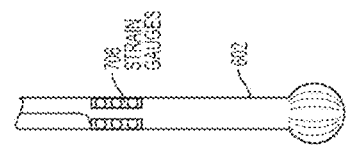

The force sensor 604 in this example may be a miniaturized industrial sensor (e.g., the multi-axis force/torque sensor from ATI Industrial Automation, Inc. of Apex, N.C.) that measures, for example, all six components of force and torque using a transducer. Alternatively, the force sensor 604 may be an optical sensor. Alternatively, the force sensor 604 may comprise a strain gauge 706 integrated directly into the shaft of the drill bit 602 as shown in FIG. 7B.

Figure 7D:
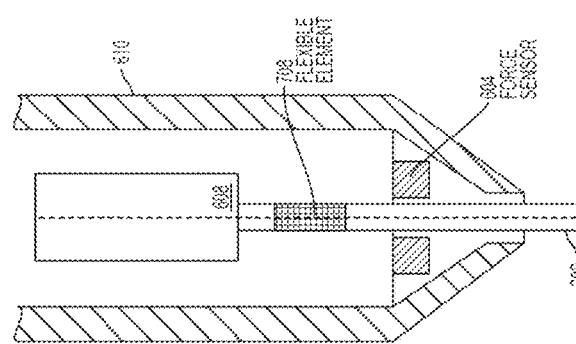
Figure 7A:
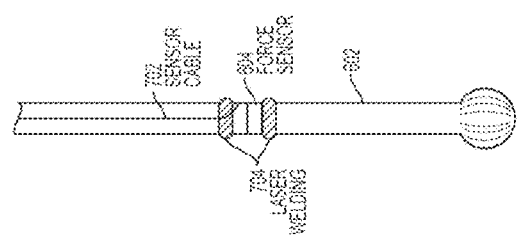
Figure 7C:
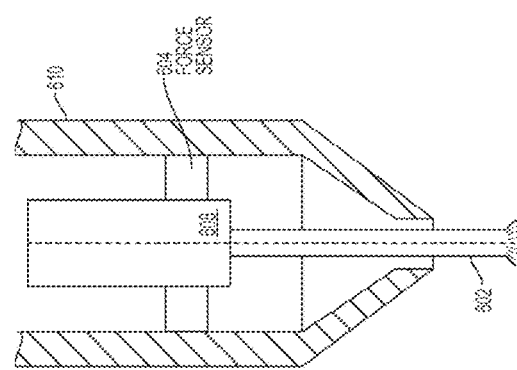

As shown in FIG. 7C, the force sensor 604, in some implementations, measures forces on the motor instead of measuring forces on the drill bit 602 itself. As shown in FIG. 7D, the shaft of the drill bit 602, in some implementations, includes a flexible element 708 that allows the drill bit 602 to bend (e.g., only slightly) such that after deflection of the shaft of the drill bit 602, forces can be measured by the force sensor 604. In some implementations, for the configuration shown in FIGS. 7C and 7D, the measurement of shaft positions (e.g., by sensor 612 as shown in FIG. 6) may be omitted as the forces are measured directly in the instrument coordinate frame.

Figure 2:
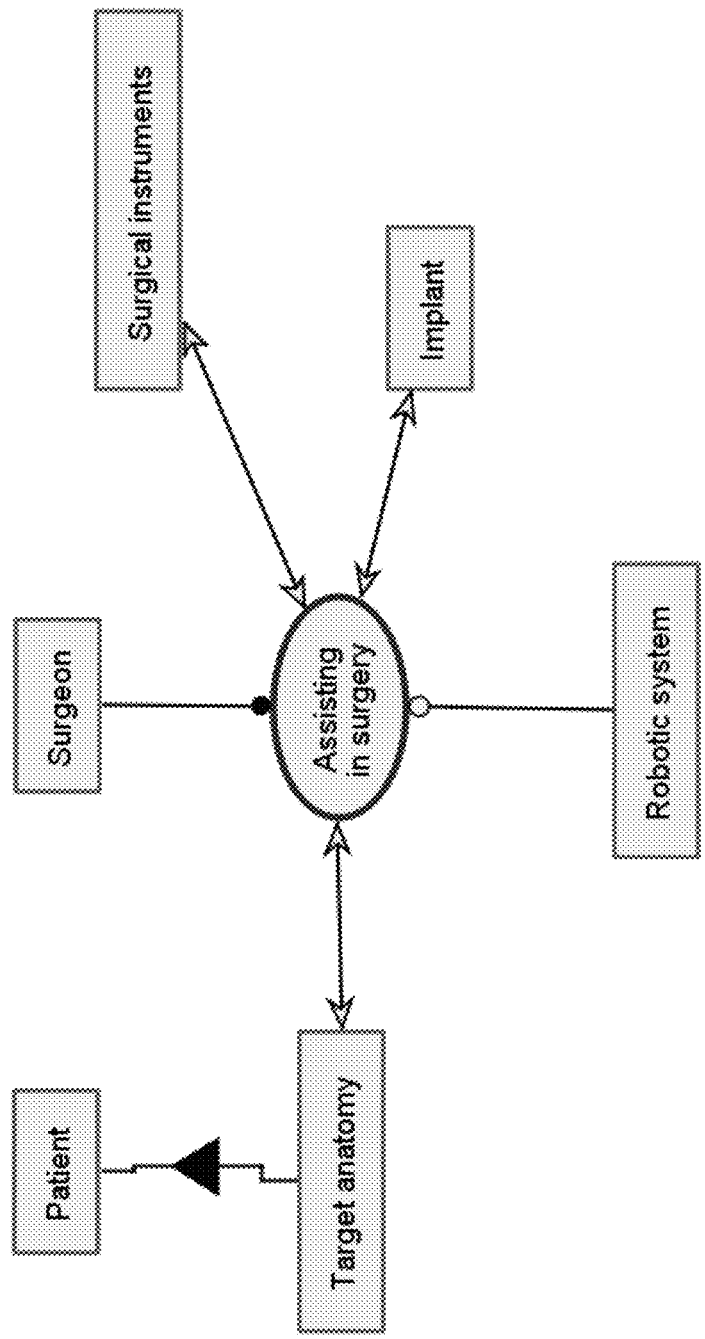
FIG. 2 is an illustration of the use of a robotic surgical system with robot-based navigation in a surgical procedure, according to an illustrative embodiment of the invention.

A goal of the robot-based navigation is to assist a surgeon during a surgical procedure that results in a change to patient's target anatomy. The implants and surgical instruments are used for this purpose and the robotic system assists the surgeon to improve the accuracy with which these instruments are used during the surgical procedure. FIG. 2 shows a schematic of all the system that assist in surgery, in some embodiments.

Figure 3:
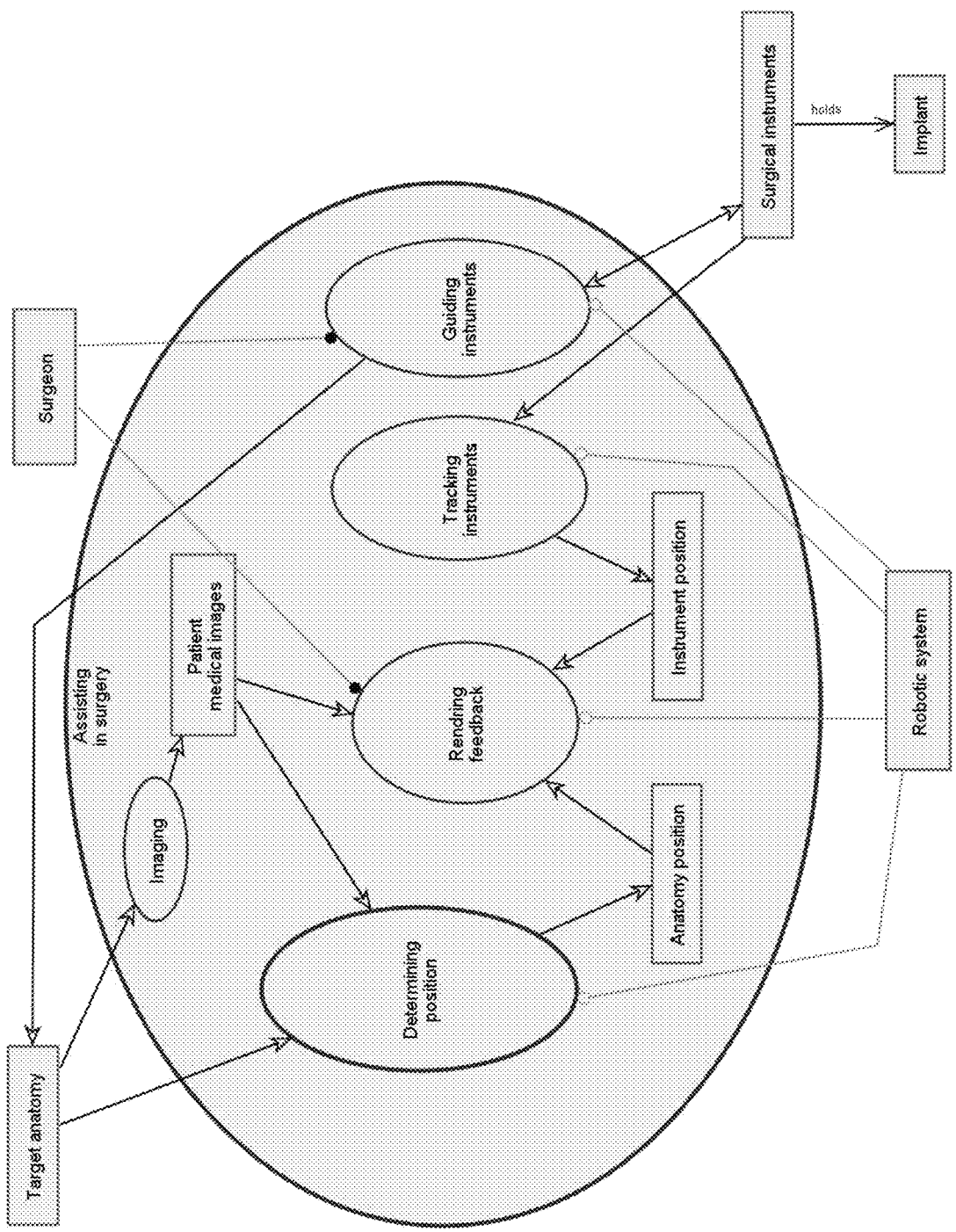
FIG. 3 is an illustration of a process of using a robotic surgical system to assist with a surgical procedure, according to an illustrative embodiment of the invention.

The interaction of a surgeon and components of a surgical system is further outlined in FIG. 3. In reference to FIG. 3, before the surgical procedure begins, the patient's target anatomy medical images are obtained using an appropriate imaging technique (e.g., which can be used to generate a model of the patient's anatomy) and used in the following processes.

The process of determining target anatomy position takes as an input target anatomy. The target anatomy may be modeled using medical images, wherein medical images are taken using a medical imaging technique or scanning-based technique. As a result, determining the target anatomy position provides the exact anatomy position of the target anatomy at any moment in time. The process of rendering feedback provides information to the surgeon based on medical images, anatomy position and instrument(s) position. The rendering is visually displayed to the surgeon. The tracking instruments process takes surgical instruments and as a result calculates their position. At the same time the instrument is guided which means that their spatial position is constrained in some way by the robotic system (i.e., using an operational volume). The robotic system implements all these four processes and the surgeon participates in the two of them: guidance and rendering feedback.

Figure 4:
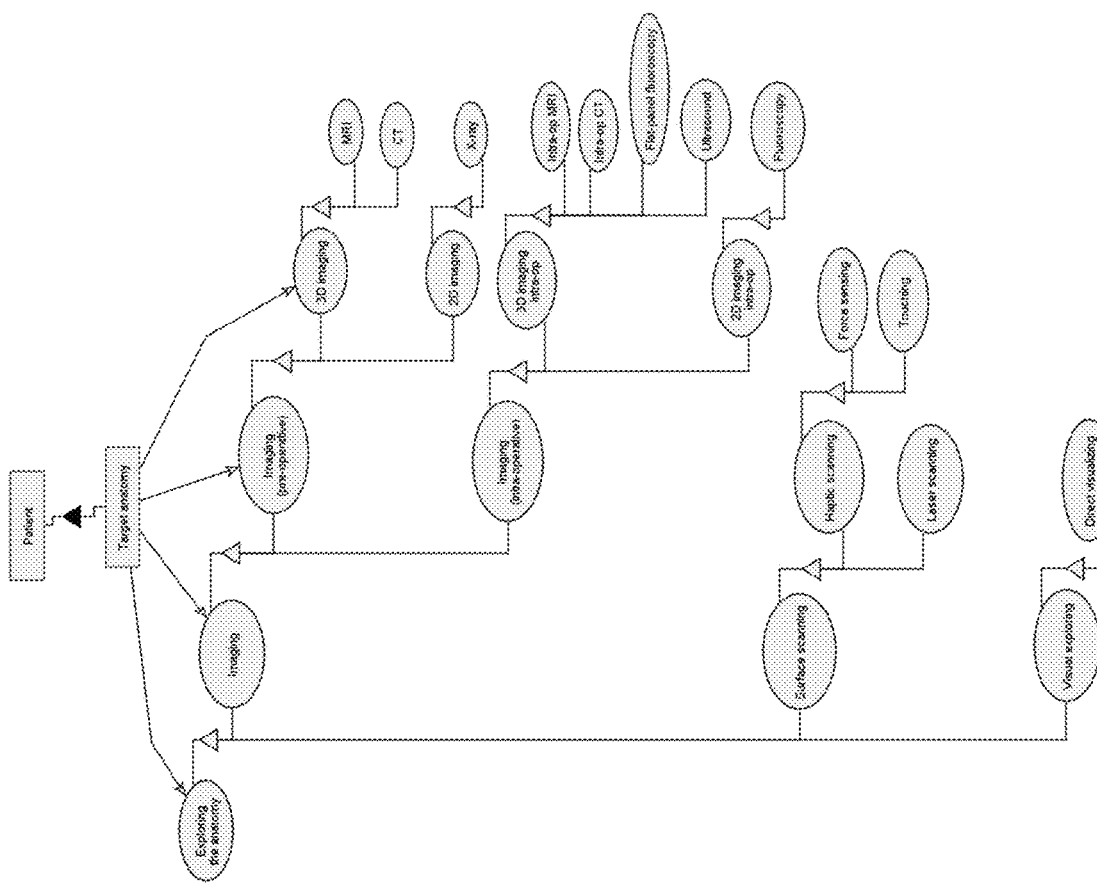
FIG. 4 is an illustration of various options for an imaging process, according to an illustrative embodiment of the invention.

Different options for the imaging process are shown in FIG. 4. The goal of the imaging process is to obtain representation of the patient's target anatomy. In some implementations, imaging is used to obtain the representation of the patient's target anatomy. The images can be obtained pre-operatively using various modalities, such as MRI, CT, or X-Rays. Alternatively, the images can be obtained intra-operatively using intra-operative imaging techniques, such as using flat-panel fluoroscopy technology (e.g. the 0-Arm by Medtronic of Minneapolis, Minnesota), intra-operative CTs, MRI and ultrasound. For example, intra-operative images can be captured using an intra-operative fluoroscopy device (e.g., a C-Arm).

There are other ways of obtaining information about the target anatomy. For example, information about the target anatomy can be collected by surface scanning using a haptic device and force feedback. Using such a device mounted on the robot allows user to measure forces that can provide spatial information about surface and rigidity of tissues.

Alternatively known techniques of surface scanning, such as a laser scanner, can be used. Additionally, visual, direct exploration can be used to explore the patient's anatomy. The outcome of these techniques, if used, is stored as medical image data, which is used to model the patient's anatomy.

FIG. 8 illustrates a range of processes that can be used for defining the position of the target anatomy (i.e., registration). Typically, the position of the target anatomy is managed using a registration procedure to identify the position of the anatomy in reference to an anatomy-fixed marker and later by the tracking (e.g., optical, or electro-magnetic) the marker and assuming that the marker moves appropriately with the anatomy to determine the position of the target anatomy. As discussed above in the Background, there are disadvantages to this approach. In certain embodiments, the disclosed technology utilizes force-based anatomy registration and re-registration to address these shortcomings. In-between re-registrations robot encoders can be used to immediately obtain instrument position at a high frequency (e.g., from 200 to 500 Hz, 500 to 800 HZ, or 800 Hz to 1200 Hz).

The initial registration data can be used along with a stability module to manage the location of the end-effector relative to the target anatomy. The stability module can run all the time in the background (e.g., automatically), in certain embodiments, without surgeon taking any special actions.

Examples of such a stability module, includes surface matching methods which take a set of points (e.g. measured points) and finds the best match between the set of points and another set of points (e.g., from the surface of the vertebra on medical images). Example algorithm for surface matching is Iterative Closet Point method described in Section 4.5.3 of "A Robotic System for Cervical Spine Surgery", Szymon Kostrzewski, Warsaw University of Technology (2011).

In certain embodiments, other algorithms are used for a stability module. Re-registration can be accomplished using other methods as well. For example, in certain embodiments, re-registration can be accomplished by periodically re-validating using fiducials. In certain embodiments, when necessary, the surgeon can touch pre-placed fiducials and re-register with an instrument attached to a robotic arm.

In certain embodiments, a specially designed marker can be fixed to the patient as shown in FIG. 9. This marker has a set of conic holes which can be easily found by a robot having a force sensor. For example, a surgeon can push a button for the robot to re-register. Then the robot automatically or the surgeon manually would bring the robot to the holes in the marker. After identifying at least 3 holes the re-registration can be found and the surgeon can continue with the surgery.

FIG. 10 is a schematic view of a process of determining a position based on automatic re-registration. The re-registration method of FIG. 10 utilizes initial registration data, patient medical images and information about the target anatomy coming from the robotic system (e.g., measured points on the surface of the bone) and, based on this information, updates the registration data which is used by the anatomy tracking process to provide the position of the target anatomy.

Various ways of rendering feedback are shown in FIG. 11. For example, feedback can be rendered using screens accessible in the operating room. In one example, feedback can be rendered using a robot-held user interface, such as the user interface described in U.S. patent application Ser. No. 14/858,325, filed Sep. 18, 2015, entitled "Robot-Mounted User Interface for Interacting with Operation Room Equipment", the content of which is hereby incorporated by reference in its entirety.

FIG. 12 is an illustration of exemplary processes for tracking instruments. In some embodiments, tracking can be accomplished using markers attached to the instrument and optical/electro-magnetic trackers. In certain embodiments, the instruments are tracked using the robotic system which provides their position in space. The robot "knows" the instrument position because it has a measurement system that is used to determine the position of the position of the end effector. Coupled with a known geometry of a given instrument, the position of the instrument attached to the end effector (e.g., in a predicable manner) is known by the robotic surgical system. Mechanical template tracking refers to mechanical, custom-made templates, which fit in one position only on the top of the target anatomy and contain guide for guiding instruments. Passive arms are standard surgical arms, which can be fixed in pre-defined position in the operating room.

FIG. 13 shows exemplary systems for guiding instruments during surgical procedures. In certain embodiments, surgical instruments are guided with robotic guidance. In certain embodiments, robotic guidance occurs automatically (i.e., without input from a surgeon) after registration of the patient's anatomy with the robotic surgical system. In certain embodiments, manual guidance and passive guidance are used during some stages of surgical procedures. Uncertain embodiments, manual guidance and passive guidance are used in all stages of surgical procedure.

A robotic surgical system with instrument attached can be used to contact a patient's anatomy at a plurality of contact points determined using haptic feedback from a force sensor attached directly or indirectly to the robotic an of the robotic surgical system. The coordinates of the plurality of contacts define a set of spatial coordinates. The value of a spatial coordinate is determined by storing the position of a portion of the robotic surgical system (e.g., a terminal point of an instrument or surgical instrument or the robotic arm) in the robot's coordinate system when contact is determined.

A set of spatial coordinates recorded from contact of the instrument with the patient's anatomy can be used to perform many navigational and surgical guidance functions such as registration, modeling volume removal, re-registration, defining operational volumes, revising operational volumes after re-registration, converting stored volume models to physical locations, and displaying surgical instruments relative to a patient's anatomy on navigation screens. A processor that is either a part of the robotic surgical system or part of a remote computing device (e.g., on a server) can be used to correlate the coordinates of surgical instruments, instruments, and/or a patient's anatomy by generating and using appropriate coordinate mappings in combination with sets of spatial coordinates. In some embodiments, a set of spatial coordinates may be provided for further use, wherein the set of spatial coordinates are generated using a technique other than haptic-feedback-based contacting of the patient's anatomy with an instrument attached to a robotic arm. For example, the set of spatial coordinates may be provided as a result of a known registration technique.

A patient's anatomy can be registered with a robotic surgical system without the use of a separate navigation system by contacting an instrument to the patient's anatomy to generate a set of spatial coordinates that can be correlated with a model of the patient generated using medical imaging data. In certain embodiments, a surgeon uses a surgical instrument to contact the patient, including during registration. In some embodiments, one or more navigation markers are used for reference during registration. Once the processor has determined a set of spatial coordinates, wherein each spatial coordinate corresponds to a point on the surface of an anatomical volume (e.g., a patient's vertebrae), the set of spatial coordinates can be mapped with a model of the patient's anatomy. The patient's anatomy may be modeled using medical imaging data. In certain embodiments, CT, MRI, or x-ray data is used to pre-operatively generate a 3D model of the patient's anatomy. In some embodiments, medical images used to generate patient anatomy models are taken intra-operatively.

A set of spatial coordinates is mapped to a model of a patient's anatomy by determining a function for converting points in the model to coordinates in the robot coordinate system (i.e., physical reality) and vice versa. In certain embodiments, mappings are made using surface matching of a surface defined by a set of spatial coordinates and the surface of the anatomical model. Points on the surface of the patient's anatomy or the anatomical model of the patient's anatomy may be extrapolated from known points (i.e., points measured by contacting the patient's anatomy with an instrwnent or data points collected during medical imaging). The extrapolated points may be used to generate the mapping. An example of a surface matching method is Iterative Closest Point (ICP) described in Section 4.5.3 of "A Robotic System for Cervical Spine Surgery," Szymon Kostrzewski, Warsaw University of Technology (2011). The contents of Section 4.5.3 are hereby incorporated by reference herein in their entirety. In general, any algorithm or method that generates a function that can be used to transform points from one coordinate system to another (i.e., bilinear transform) is appropriate for use. A threshold may be specified that defines an error measure that the mapping must stay under in order to be used. This threshold can be set to a value that is sufficient for high precision mapping (e.g., registration), but such that mappings can be generated with high frequency (i.e., the speed of the generation of the mapping does not rate limit a surgical procedure).

Prior to registration, there is no defined relationship between the coordinate system that defines the anatomical model of the patient in the medical imaging data and the coordinate system that defines the location of a surgical instrument attached to the robotic arm of the robotic surgical system. By generating a coordinate mapping from the robot coordinate system to the medical image data coordinate system and storing the coordinate mapping, a processor can determine a physical location for each point of the patient's anatomy represented in the anatomical model. In this way, the patient is registered with the robotic surgical system.

Once a patient is registered, for each point in space, the robotic surgical system knows whether that point is on the surface of the patient's anatomy, in the patient's anatomy, or outside of the patient's anatomy. This information can be used for further processing to assist in surgical guidance and navigation. For example, this information can be used to define "no go" zones for a surgical instrument if the patient's anatomy is to be avoided entirely or only a portion of the patient's anatomy is to be accessible to the surgical instrument. Additionally, a surgical instrument could trace a line, plane, or curve that falls on the surface of the patient's anatomy.

In order to accurately register a patient using haptic-feedback-based contacting, as described above, only a small set of points need to be contacted. For example, in certain embodiments, no more than 30 points are needed to register a patient's anatomy to a robotic surgical system with sufficient precision to proceed with surgery. In certain embodiments, only 5-10 contacts are needed. The number of contacts necessary varies with the particular surgical procedure being performed. In general, surgeries requiring more precise surgical instrument positioning require more contacts to be made in order to generate a larger set of spatial coordinates. Given the simplicity of using a robotic surgical system to contact the patient's anatomy, a sufficient number of contacts for registration may be made in a short period of time, thus expediting the overall surgical procedure.

In certain embodiments, the coordinate mapping is used to generate navigational renderings on a display, for example, where a terminal point of a surgical instrument is shown in correct relation to the patient's anatomy. This rendering can be live updated as the position of the surgical tool shifts. This is done without the need for navigational markers because the location of the surgical tool is known from registration. In certain embodiments, the set of spatial coordinates is collected by contacting a fiducial marker with a plurality of orienting points (e.g., indents) on the marker (e.g., distributed on faces of the marker}, wherein the orienting points are in a known location relative to the patient's anatomy due to the marker being engineered to attach in a specific location on the patient's anatomy (see FIG. 9). In certain embodiments, the specific location is the spinous process of a vertebra.

In some embodiments of methods and systems described herein, registration is performed using a technique known in the art.

During certain surgical procedures, a portion of a patient's anatomy (i.e., a first volume) originally included in a model of the patient's anatomy is removed during an operation prior to the removal of an additional volume, for example, to gain access to the additional volume. The removal of the first volume may not require high precision during removal. The removal of the first volume may be done manually. The model of the patient's anatomy can be updated to reflect this removal. The model update may be necessary to maintain accurate patient records (i.e., medical history). The model update may be necessary for intra-operative planning of additional volume removal.

A set of spatial coordinates can be used to update the model of a patient's anatomy after volume removal. In certain embodiments, the set of spatial coordinates are generated using haptic-feedback-hazed contacting of the patient's anatomy with an instrument attached to a robotic arm.

Using a set of spatial coordinates and a model of the patient's anatomy, points on the patient's anatomy that were formerly inside the surface of the anatomy can be determined, if a coordinate mapping between the model's coordinate system and the coordinate system of the spatial coordinates (i.e., a robot's coordinate system) has been generated. The coordinate mapping may be generated, for example, during registration. The set of spatial coordinates can be converted to be expressed in the coordinate system of the model using the coordinate mapping. Then, coordinates determined to be located on the interior of the model's surface can be used to define a new surface for the model. For example, if half of a rectangular solid is removed, an instrument attached to a robotic surgical system can contact points that were previously on the inside of the rectangular solid, thus, the coordinates of the points when converted to the model's coordinate system will be located inside the model. These points can be used to determine a new surface for the model. Thus, the volume of the model will shrink by excluding all points in the removed volume from the model. The updated model will have a smaller volume than the original model that accurately reflects the change in size that occurred due to volume removal. A coordinate may be included in a set of coordinates that is not determined to be an internal coordinate in the model (i.e., the model before updating). This coordinate would not be used to define a new surface as it would be part of an existing surface. This coordinate is thus not used to update the model.

Figure 16:
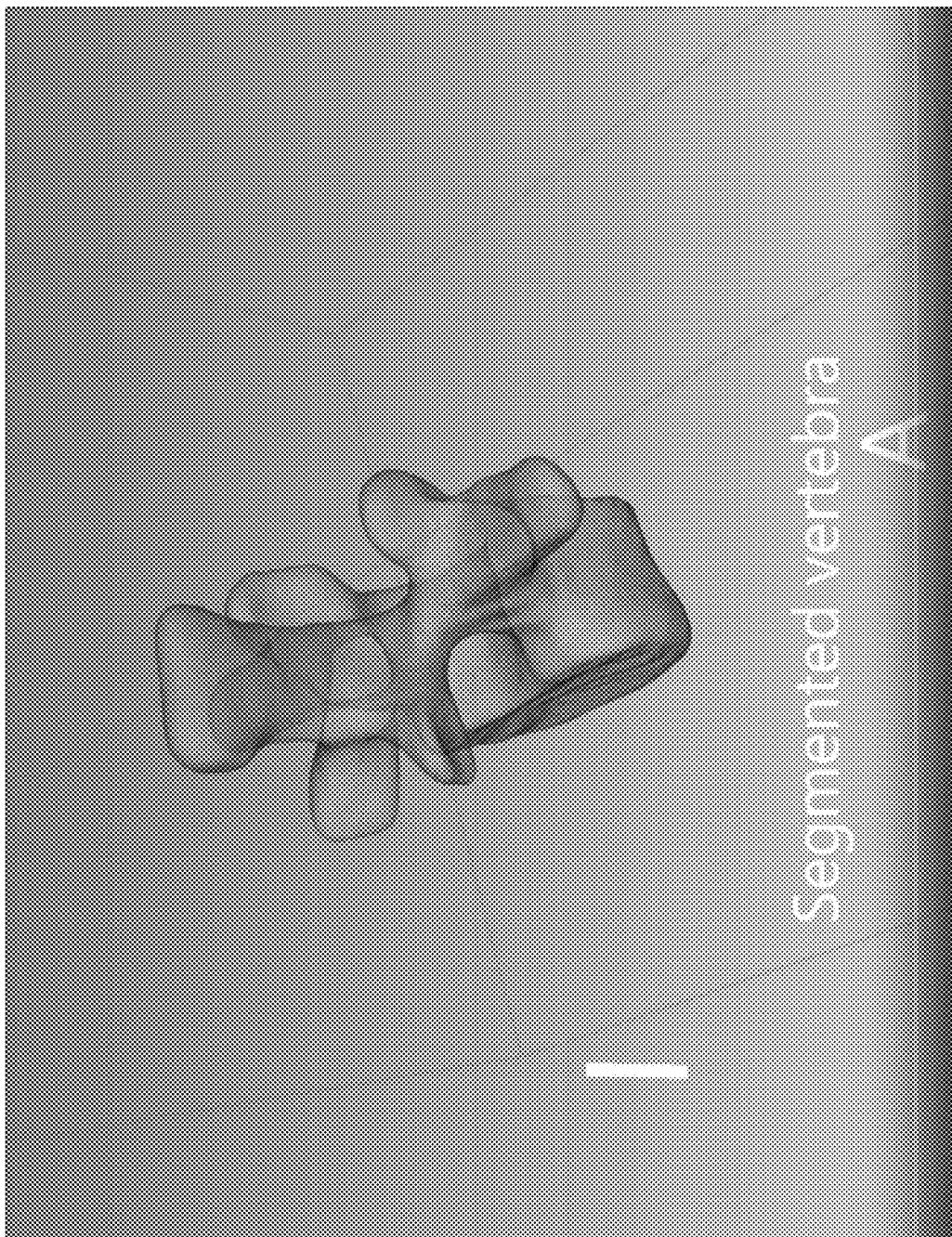
Figure 17:
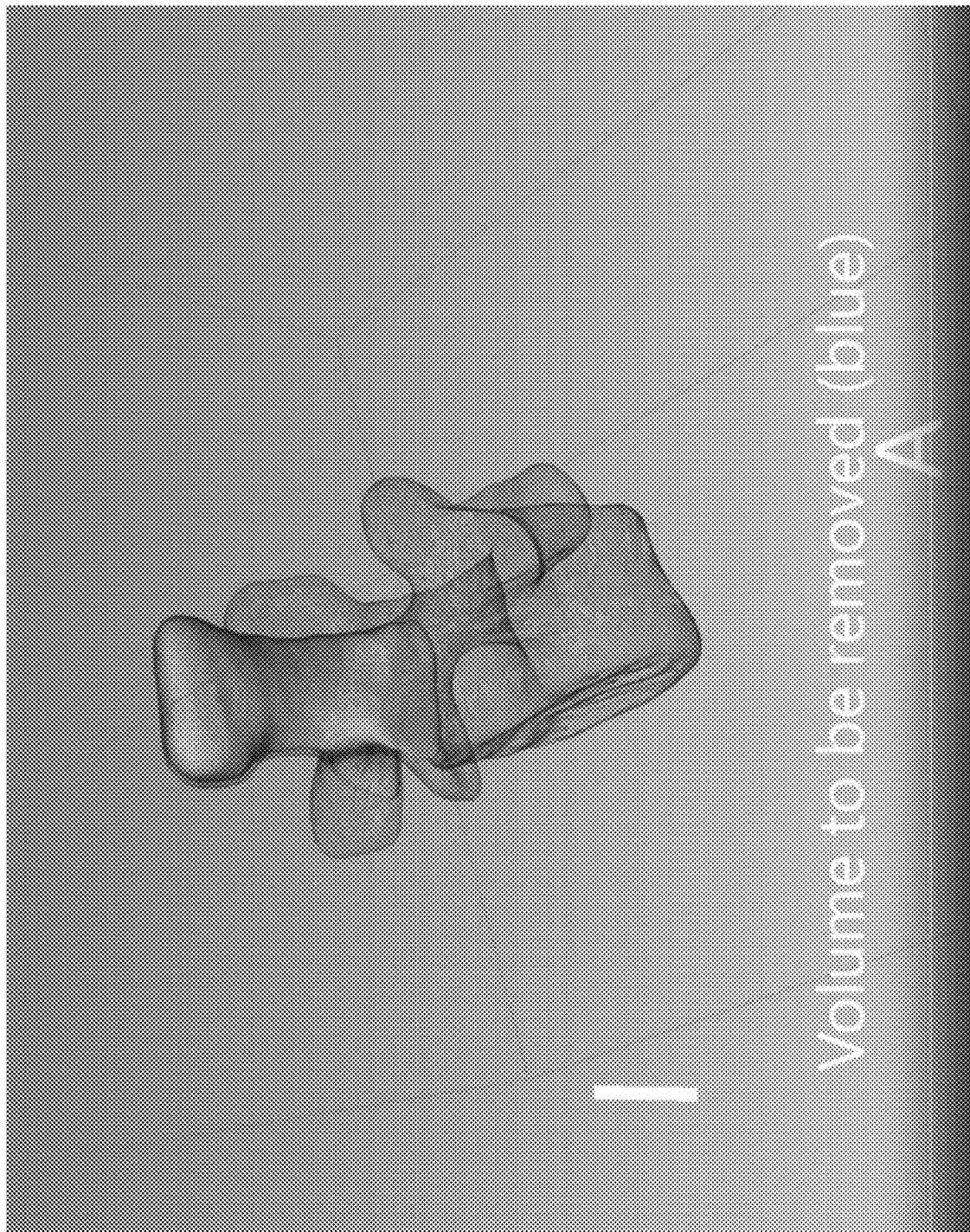
Figure 28:
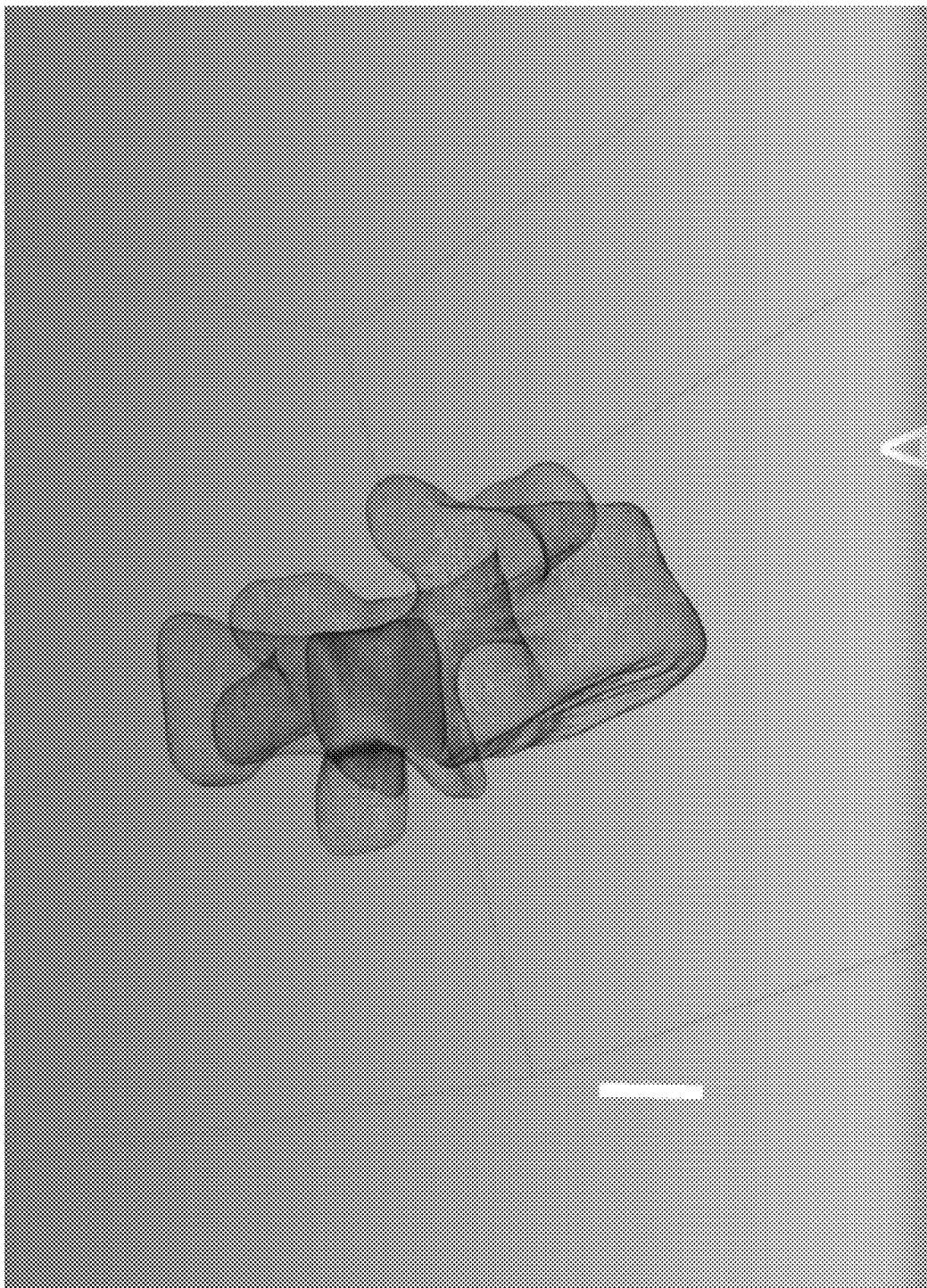

The revised set of coordinates that define the new surface of the patient's anatomy after volume removal can be stored as an updated model for future reference. This updated model may be stored in addition to or overwrite the original model. When patient data is augmented to comprise both the original model before volume removal and the updated model after volume removal, a comparison can be displayed. This comparison includes displaying the original model, the updated model, and the portion that was removed. An exemplary original model is shown in FIG. 16. An exemplary model highlighting the removed portion is shown in FIG. 17. An exemplary updated model after volume removal is shown in FIG. 28.

Because typical registration procedures are lengthy and require unobstructed line-of-sight (either visually or electromagnetically unobstructed line-of-sight), a navigation system and/or robotic surgical system are typically only registered once during a surgical procedure, at the beginning. However, a patient's orientation and/or position relative to these systems may shift during the procedure. Additionally, depending on the type of procedure, the patient's anatomy may undergo physical changes that should be reflected in the registration. Serious medical error can result during a surgical procedure due to any desynchronization that occurs between physical reality and the initial registration. In general, more complex procedures involving many steps are more prone to desynchronization and with greater magnitude. Serious medical error is more likely in surgical procedures on or near sensitive anatomical features (e.g., nerves or arteries) due to desynchronization. Thus, easy and fast re-registration that may be performed intra-operatively is of great benefit.

Re-registration acts to reset any desynchronization that may have happened and, unlike traditional registration methods, haptic-feedback-based contacting with robotic surgical systems are easy to integrate methods for re-registration. In certain embodiments, a re-registration can be processed in 1-2 seconds after re-registration contacts are made. In certain embodiments, re-registration can be processed in under 5 seconds. Re-registration may be performed with such a system or using such a method by contacting the patient's anatomy at any plurality of points. There is no need to contact the patient's anatomy at specific points, for example, the points contacted during initial registration.

After an initial registration is performed that defines a coordinate map between a robot's coordinate system and the coordinate system of a model of the patient's anatomy, re-registration may be performed. Each coordinate of the patient's anatomy is known to the robotic surgical system after registration by expressing coordinates of the patient's anatomical model in the robot's coordinate system using a coordinate mapping. By collecting a set of spatial coordinates, the surface of the patient's anatomy expressed in the robot's coordinate system can be mapped to the surface defamed by the set of spatial coordinates. The mapping can be used to update the coordinate mapping.

An updated coordinate mapping may reflect changes in the patient's anatomy, orientation, or position. For example, if a patient is rotated about an axis, the patient's physical anatomy will be tilted relative to what the patient's anatomical model reflects when expressed in a robot's coordinate system. An instrument can contact the patient's anatomy after the rotation at a set of points on the patient's anatomy (for example, 5-10 points). A re-registration map between the current patient's anatomical model expressed in the robot's coordinate system and the surface defamed by the set of points is generated. The coordinate map can be modified using the registration map to produce an updated coordinate map. For example, if both the coordinate map and re-registration map are linear transforms stored as arrays, the updated coordinate map is the product of the two arrays. Likewise, a change in position will be reflected as a translation during re-registration and a change in the patient's anatomy may be reflected as a scaling transform. For example, the spacing of a patient's vertebrae may change after volume removal, prompting a surgeon to perform re-registration.

In certain embodiments, the model of the patient's anatomy is updated simultaneously during re-registration if one or more of the set of spatial coordinates is determined to be an interior coordinate of the model (i.e., the model as it existed pre-re-registration). For example, in certain embodiments, re-registration may be performed after a volume removal whereby re-registration and model updating are processed in one simultaneous method. Re-registration is useful after volume removal because given the likelihood of anatomical shifting during such a significant surgical step is high.

In certain surgical procedures, the use of a surgical instrument should be constrained to only a specific operational volume corresponding to the surgical site of the patient's anatomy. Operational volumes are physical volumes, wherein the physical volume is defined using the robot's coordinate system. It is clear that the physical volume in which the surgical instrument should be constrained is relative to the patient's anatomy. In certain embodiments, a robotic surgical system provides haptic feedback when a surgeon attempts to move the surgical instrument outside of the operational volume. In this way, the surgeon feels resistance when the surgical instrument is at the boundary of the operational volume and can redirect the surgical tool away from the boundary. This is useful, for example, during bone removal, where a surgeon does not want to remove bone from locations outside of the intended volume. Operational volumes are stored on a non-transitory computer readable medium for use in providing haptic feedback to surgeons during surgical procedures.

Using a coordinate mapping, a physical operational volume occupied by a volume of and/or around a patient's anatomy can be precisely defined using the patient's anatomical model. The intended operational volume can be defined intra-operatively. A surgeon can contact a set of points on the patient's anatomy to generate a set of spatial coordinates that define a boundary of the operational volume. In many surgical procedures, the operational volume corresponds to an anatomical feature of the patient's anatomy. For example, a particular bone or segment of a bone. Thus, in certain embodiments, the surgeon selects the anatomical feature from a model of the patient's anatomy. The model of the patient's anatomical feature can be mapped to the set of spatial coordinates corresponding to the surgeon's desired operational volume boundary. In certain embodiments, each coordinate in the model of the patient's anatomical feature can expressed using the robot's coordinate system based on the mapping.

Then, the operational volume can be defined and expressed in the robot's coordinate system using the mapping of the model of the patient's anatomical feature to the set of spatial coordinates. In some embodiments, each coordinate of the surface of the model of the patient's anatomical feature is used to define the surface of the operational volume.

In certain embodiments, the operational volume is the volume defined by the surface defined by the set of spatial coordinates. Thus, these methods for producing operational volumes do not require medical imaging data or a pre-constructed model of the patient's anatomy. For example, a surgeon may contact 10 points on a patient that are determined as a set of spatial coordinates. The set of spatial coordinates can be used as a set of vertices (i.e., surface points) that define a volume. This may be used as an operational volume wherein movement of a surgical instrument attached to the robotic arm of the robotic surgical system is constrained to that operational volume. This can be done with or without any registration.

An operational volume may be defined by a surgeon selecting a volume of a patient's anatomical model without generating a set of spatial coordinates (i.e., without contacting the patient's anatomy). The surgeon may select the volume using software that allows viewing of the patient's anatomical model. Once the volume is selected, a coordinate mapping that maps the anatomical model to the robot's coordinate system may be used to generate a set of coordinates that define the operational volume. Thus, the operational volume is defined using a coordinate mapping generated during, for example, registration or re-registration, and does not require a surgeon to separately generate a set of spatial coordinates for use in defining the operational volume by contacting the patient's anatomy.

Stored operational volumes may be updated when a coordinate mapping is updated or at some later time using the updated coordinate mapping. The coordinate mapping is updated during re-registration, for example, to reflect a shift in the position, orientation, or change in the patient's anatomy. The coordinates of the stored operational volume may be converted to the new robot coordinate system by mapping the new robot coordinate system to the robot coordinate system the stored operational volume is expressed in and using the mapping (i.e., by converting each coordinate of the operational volume to the new coordinate system and storing the converted coordinates as the updated operational volume).

Similarly, any stored model volume that is expressed in a medical image data coordinate system can be converted to a spatial volume by expressing the coordinates of the model volume in the robot's coordinate system using a coordinate mapping. This allows a robotic surgical system to trace, enter, maneuver only within or maneuver only outside a physical volume corresponding to the model volume.

A surgeon benefits from visualizing the position of a surgical instrument relative to a patient's anatomy to assist in navigation and decision making during a surgical procedure. When the terminal point of a surgical instrument has a pre-defined position relative to the origin of a robot's coordinate system, the terminal point can be converted to a position in a medical image data coordinate system with a coordinate mapping between the robot's coordinate system and the medical image data coordinate system using the position of the robotic arm. In certain embodiments, the terminal point is used to represent the position of the robotic arm. In certain embodiments, all surgical instruments have the same terminal point when attached to a robotic arm. After converting the terminal point to be expressed in a medical image data coordinate system, the terminal point can be plotted relative to a model of the patient's anatomy that precisely reflects the distance between the terminal point and the patient's anatomy in physical space. Using this, rendering data can be generated that, when displayed, shows a representation of the terminal point (and, optionally, the surgical instrument) and the model of the patient's anatomy. Thus, visualization of the surgical instrument and its position relative to the patient's anatomy can be made without the use of a navigational marker attached to the surgical instrument and without using image recognition techniques.

The rendering data may be displayed on a screen that is part of the robotic surgical system or that is viewable from inside and/or outside an operating room. The screen may be mounted on the robotic arm. The rendering data may be updated to refresh the display in real-time or substantially real-time (i.e., acting as a video feed of the patient). The representation of the terminal point and/or surgical instrument may be overlaid over a representation of the model of the patient's anatomy or over medical images taken pre- or intra-operatively. The position of the terminal point on a display will update as the position of the robotic arm is adjusted.

FIG. 9 shows an exemplary fiducial marker that can be used in registration and/or re-registration. The fiducial marker has indents distributed across different faces of an orientation member. Here, the orientation member is a cube. The attachment member of the fiducial marker is attached to the spinous process of a vertebra, but can equally be adapted to attach to any desired point on patient's anatomy. When the surgeon contacts the orientation points (i.e., indents) using a haptic-feedback-contacting method as described herein, a coordinate mapping can be generated if the orientation points have a defined spatial relationship to the patient anatomy.

The following is a description of an exemplary surgical method for performing a laminectomy, but it is understood that the method can easily be adapted to other types of volume removal surgery. Additionally, many of the steps discussed in this exemplary method are applicable to surgical procedures that do not involve volume removal or involve surgical outcomes other than volume removal. Aspects of the surgical method are shown in FIGS. 14-35.

Figure 14:
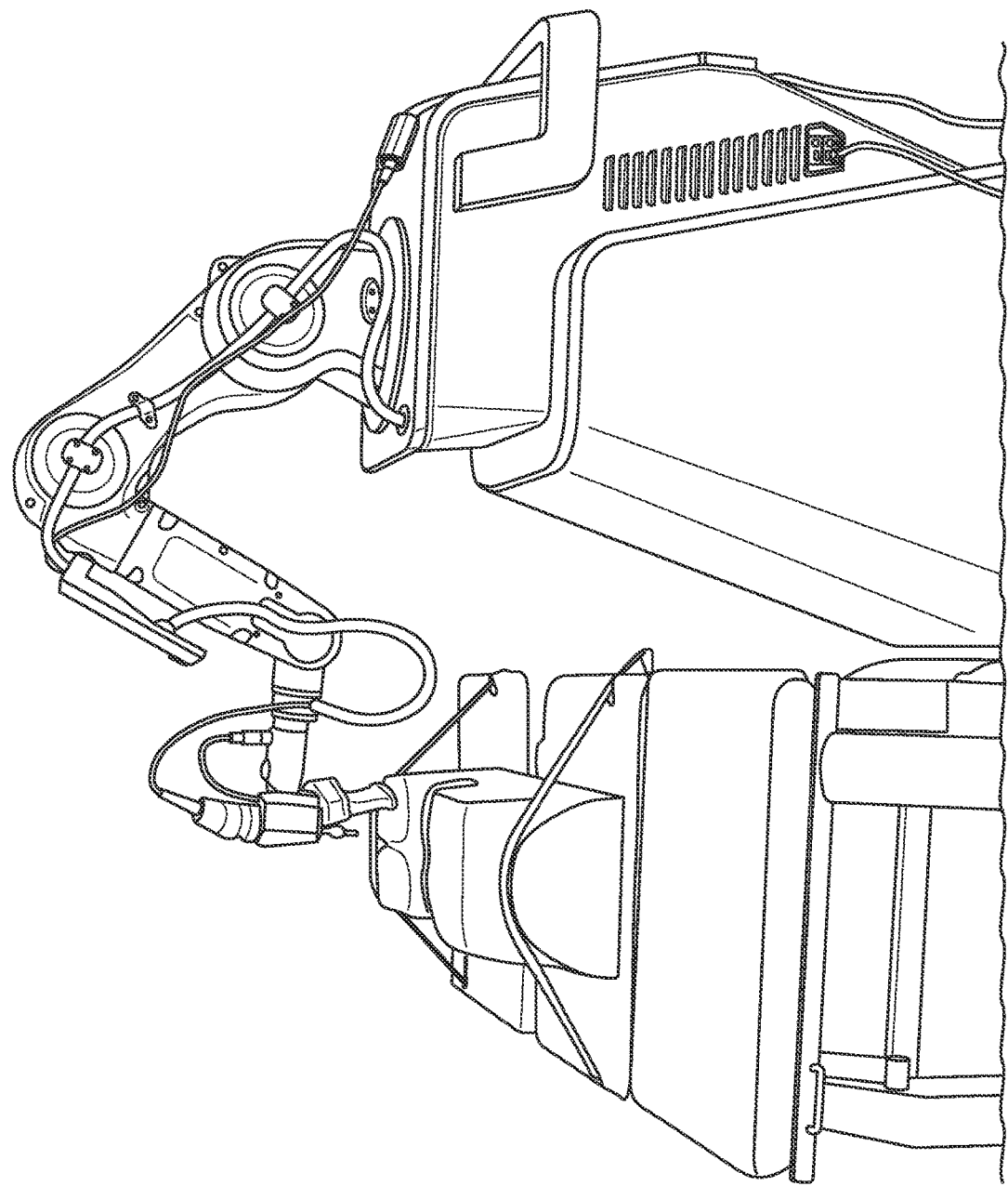
Figure 15:
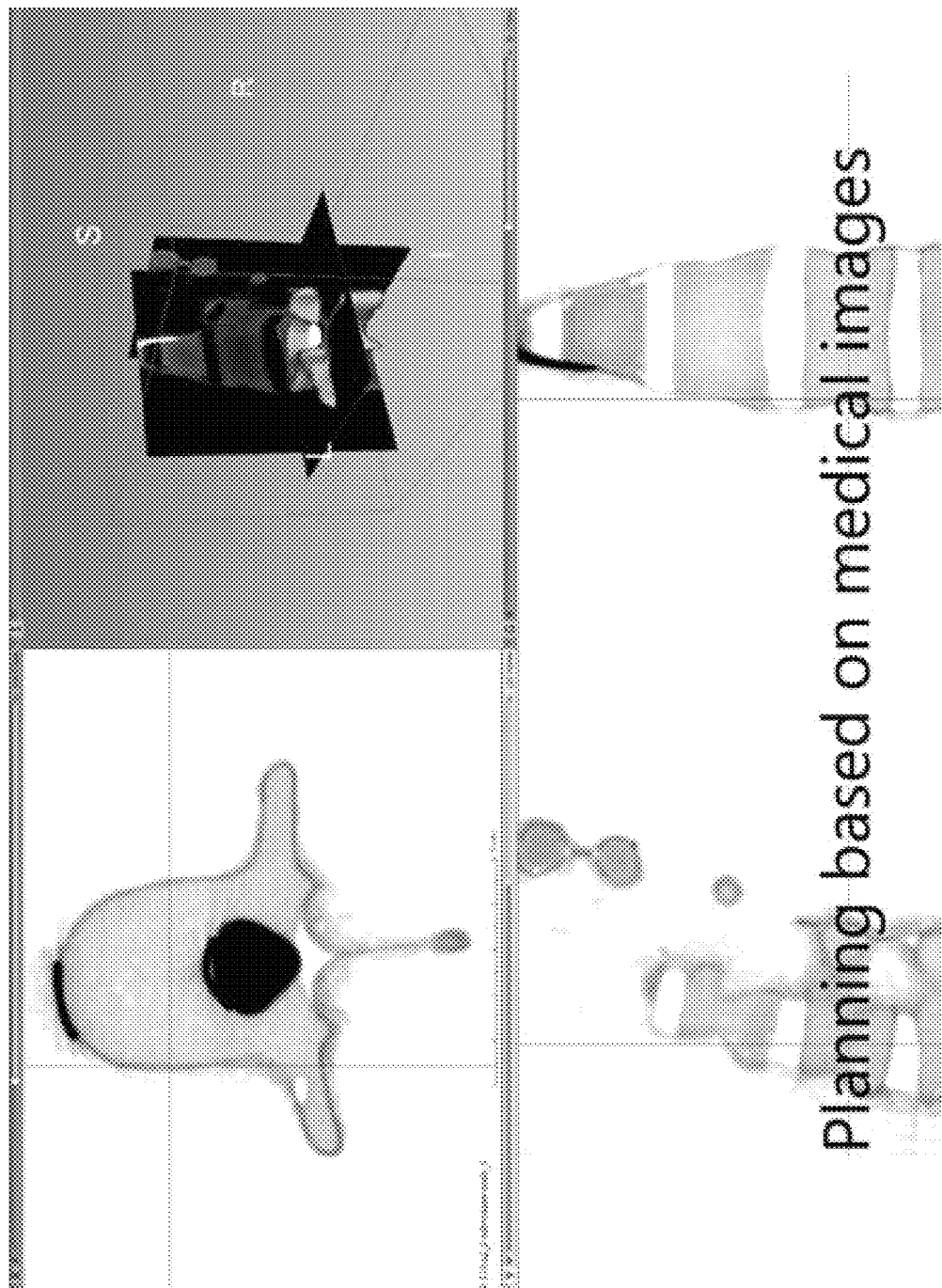
Figure 18:
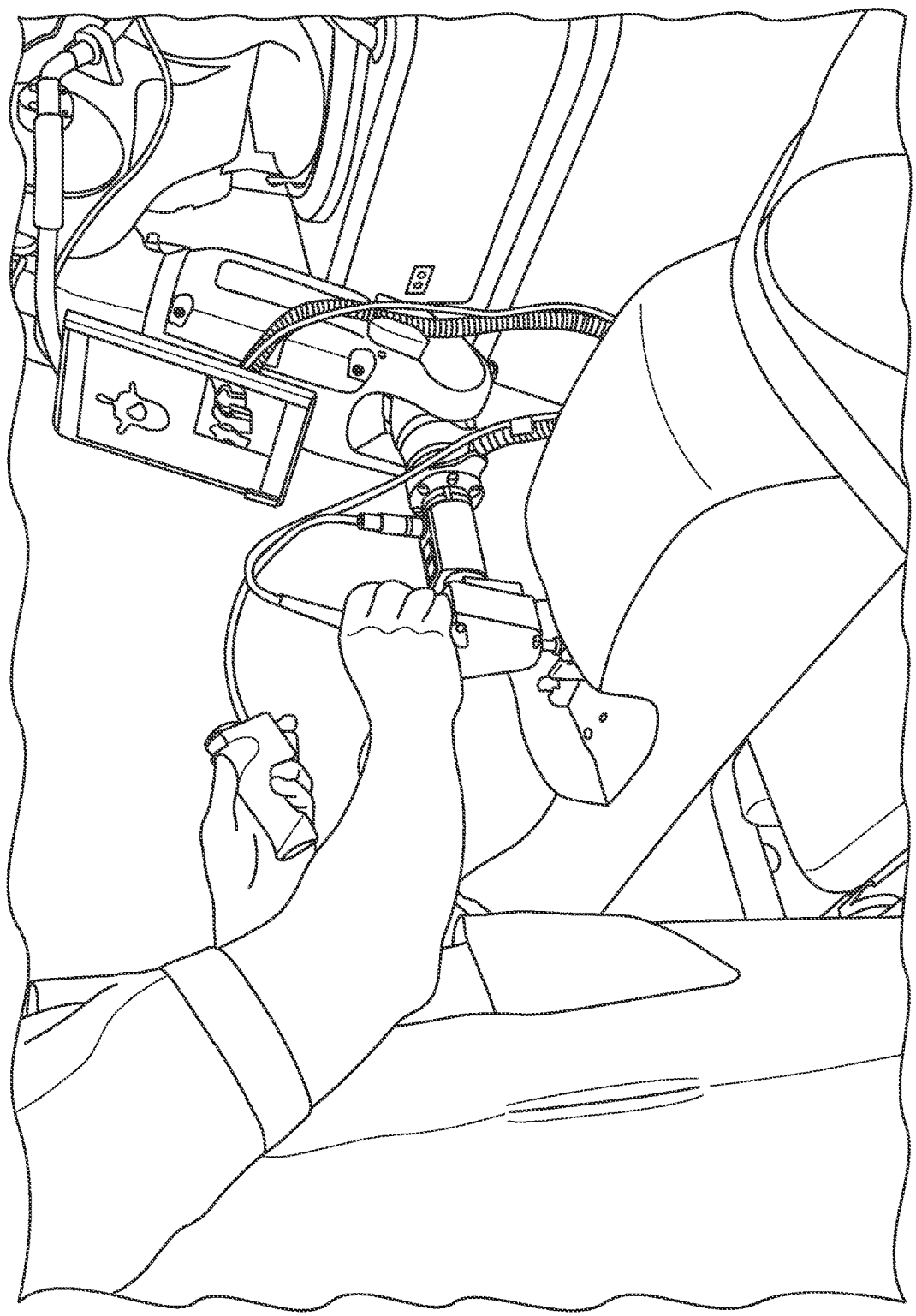
Figure 19:
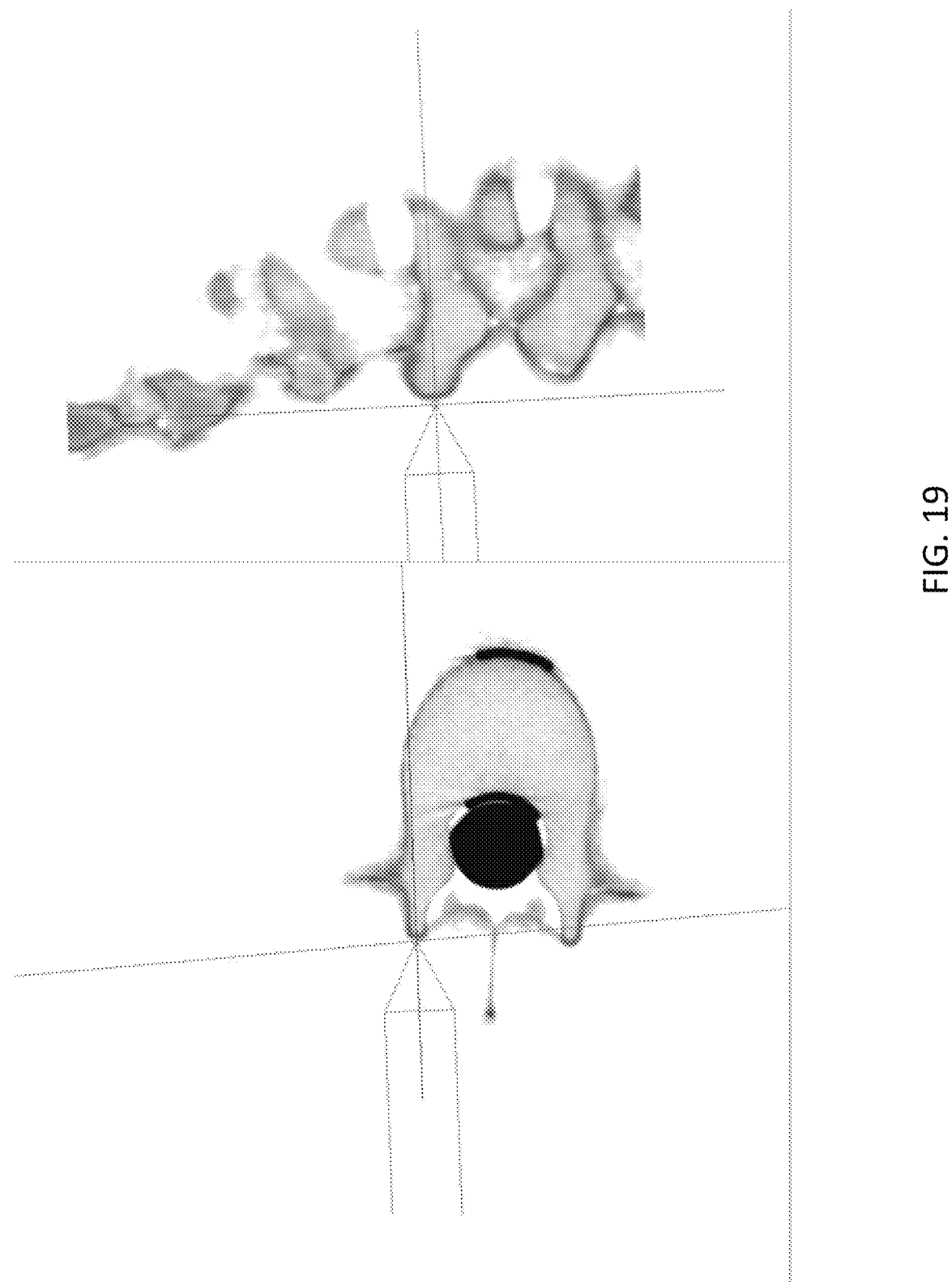
Figure 20:
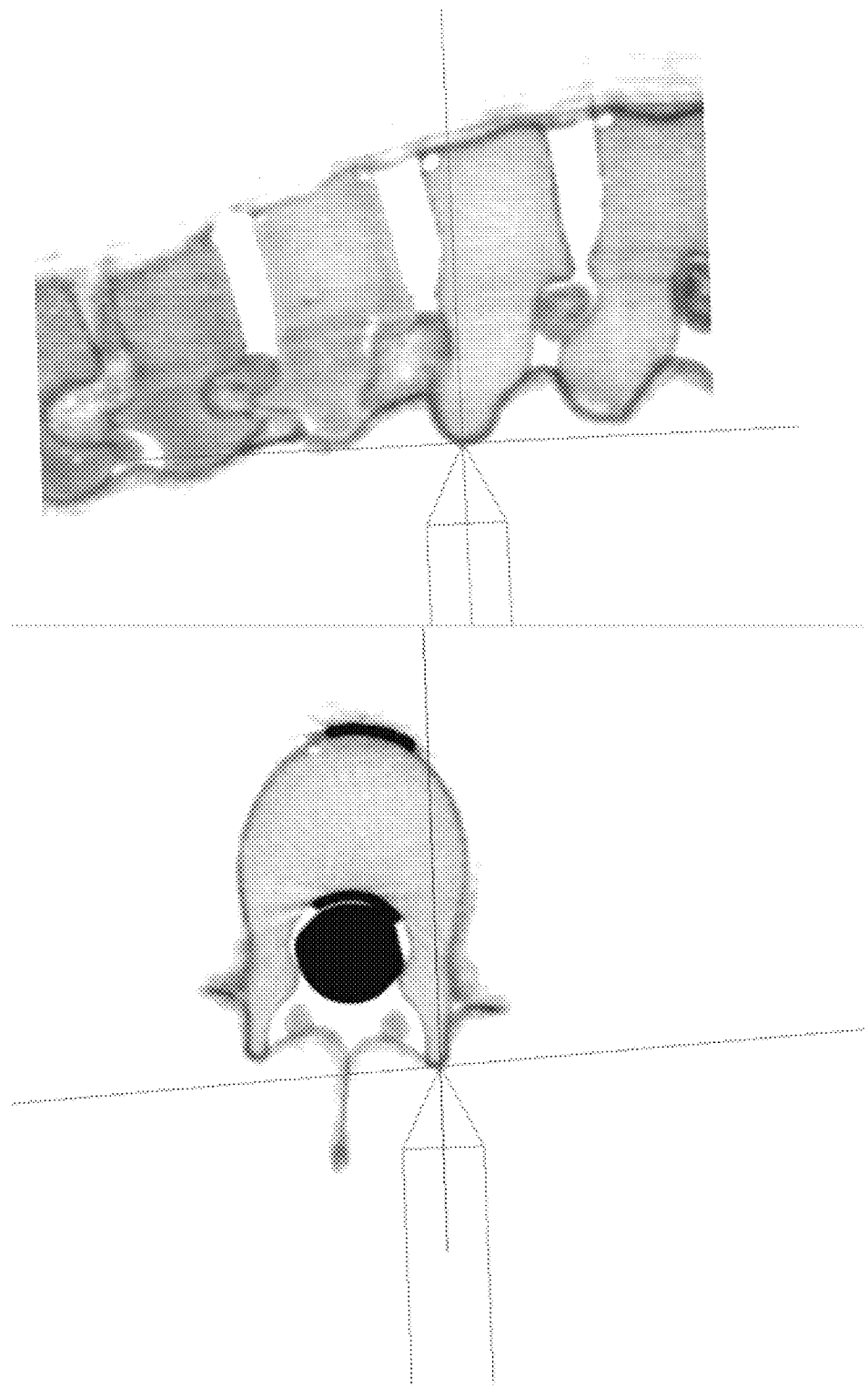
Figure 21:
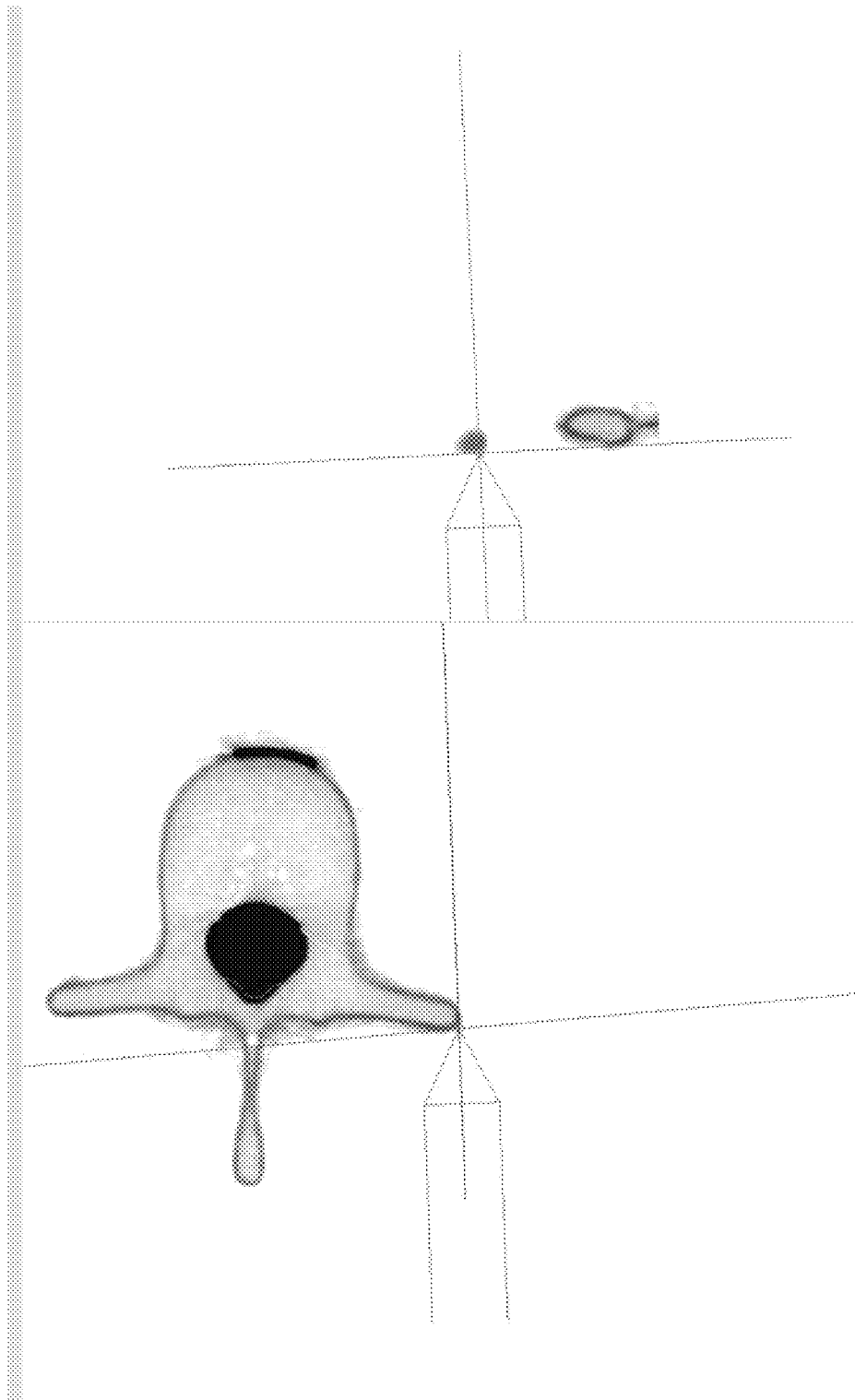
Figure 22:
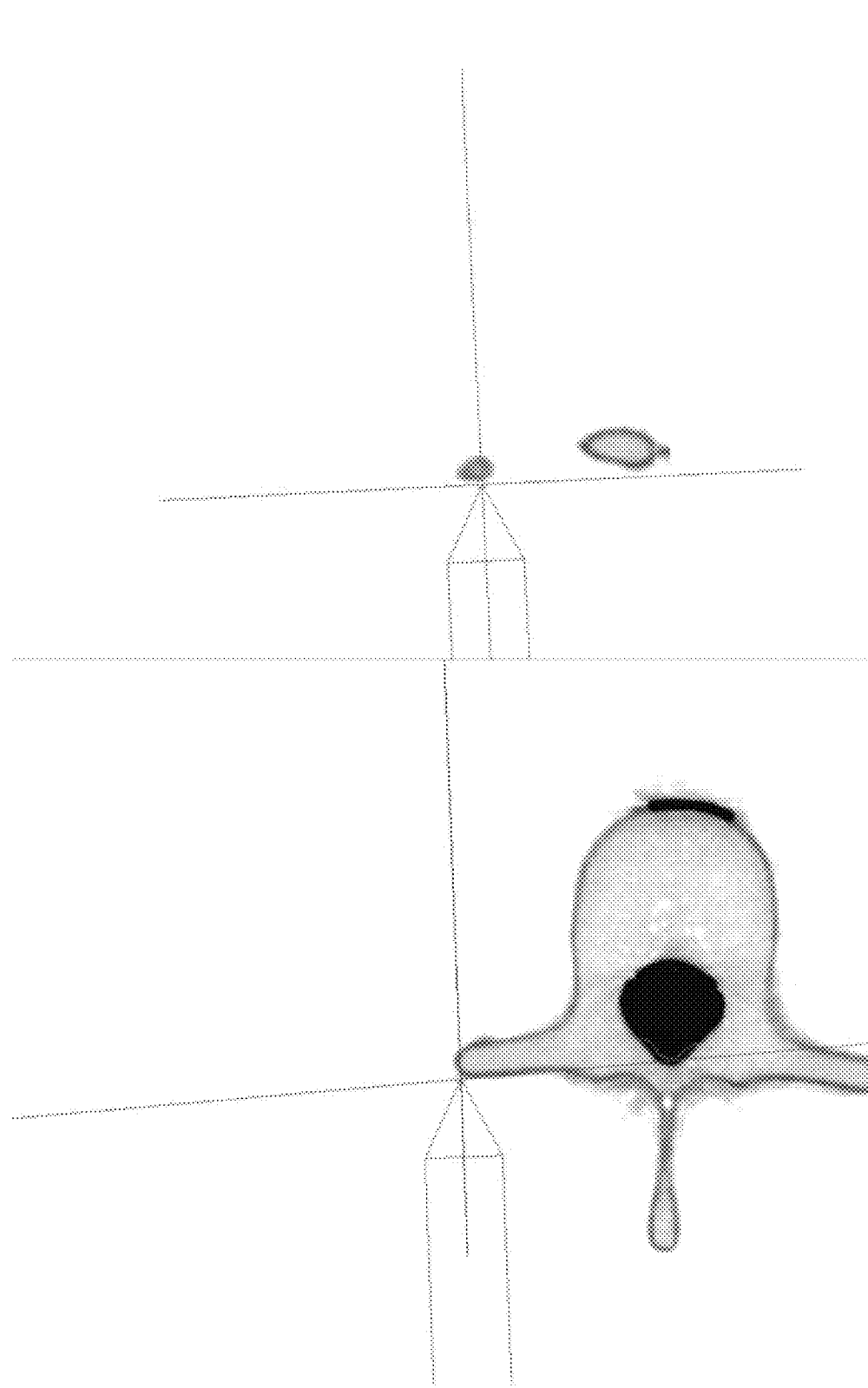

FIG. 14 shows an exemplary robotic surgical system that can be used to perform a laminectomy using robotic-based navigation. FIG. 15 shows an exemplary navigation display that can be used by a surgeon for pre-operative planning, for example, to identify an operational volume of the patient's anatomy using the model of the patient's anatomy displayed on the display. FIG. 16 shows an additional exemplary navigational display where the segmented vertebra will be the site of the laminectomy. Using preoperative planning, an initial volante to be removed has been identified in the model of the patient's anatomy. The initial volante is identified in light blue in FIG. 17. FIG. 18 shows a surgeon using the robotic surgical system to receive real-time feedback. The real-time feedback comprises haptic feedback from the surgical instrwnent attached to the robotic surgical system and visual feedback on the navigation screen attached to the robotic arm.

Figure 23:
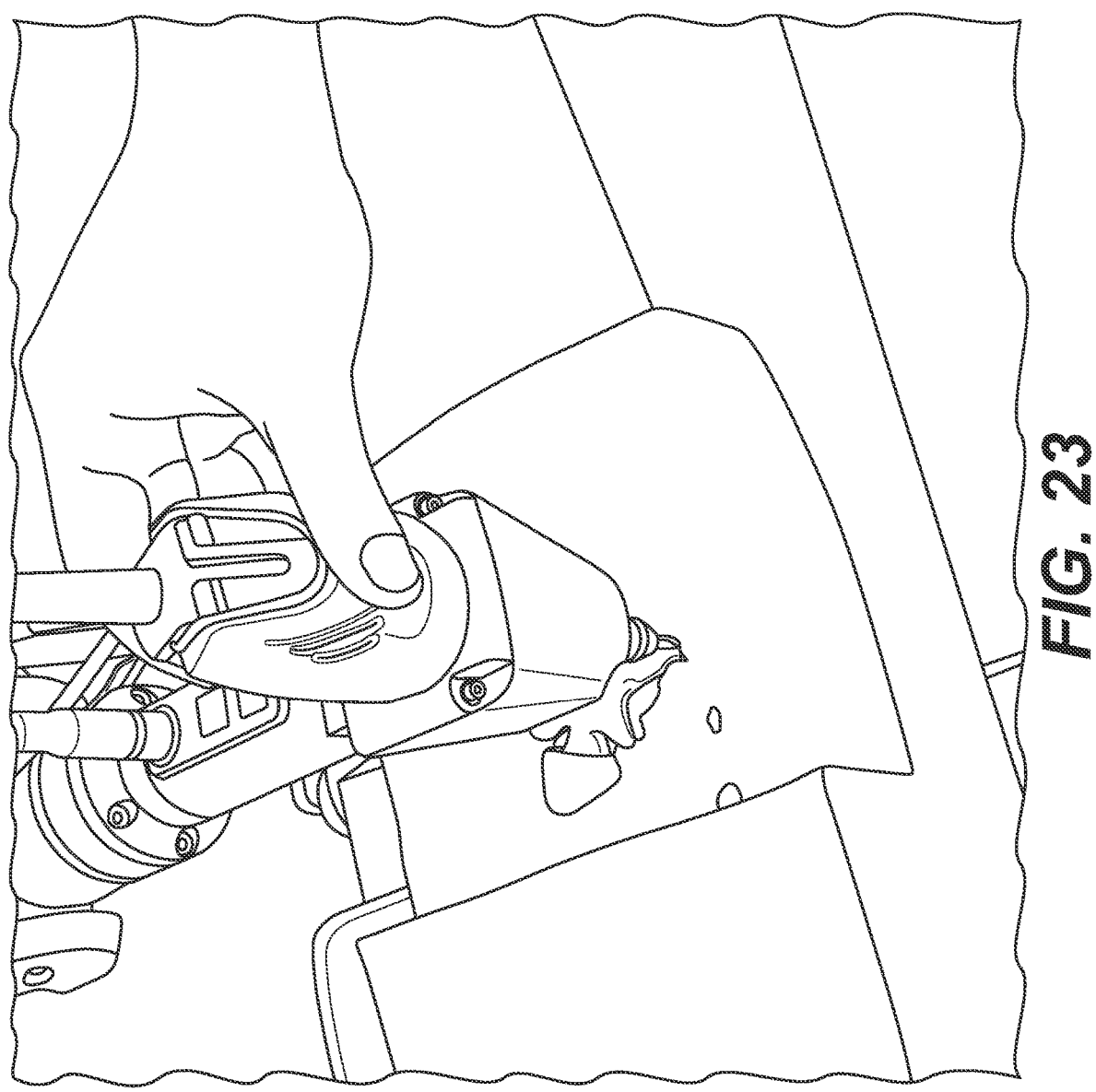
Figure 24:
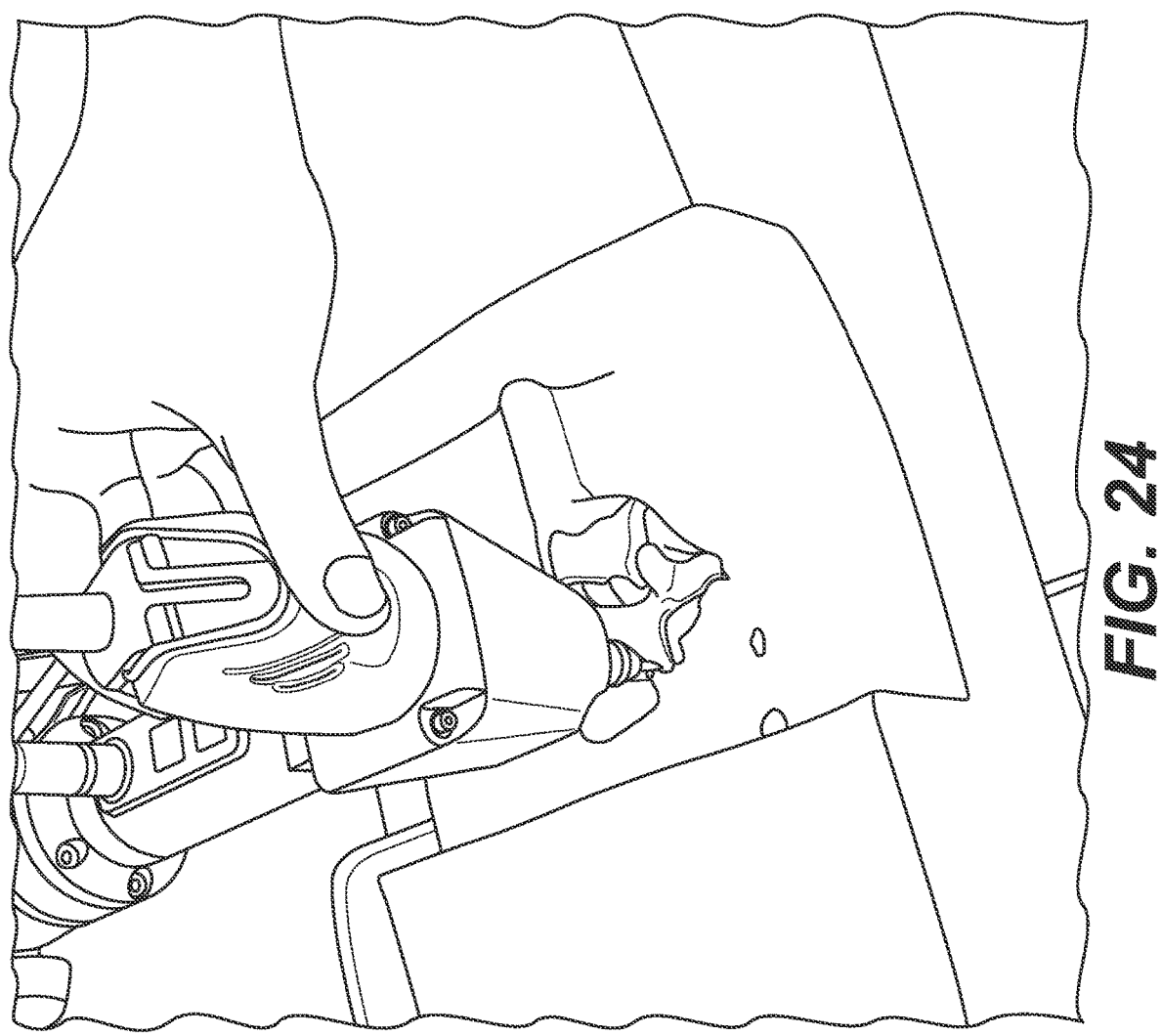

FIGS. 19-24 show a surgeon registering the patient to the robotic surgical system. FIGS. 19-22 show views of a navigation display while the patient is registered. The navigation shows two perspectives of medical image data that models the patient's anatomy and a representation of the surgical instrwnent. In these figures, the surgical instrwnent is touching points of the patient's anatomy (i.e., the patient's vertebra). FIGS. 23 and 24 show the surgical instrwnent and robotic arm in various stages of contacting the patient's anatomy to generate a set of spatial coordinates during registration.

Figure 25:
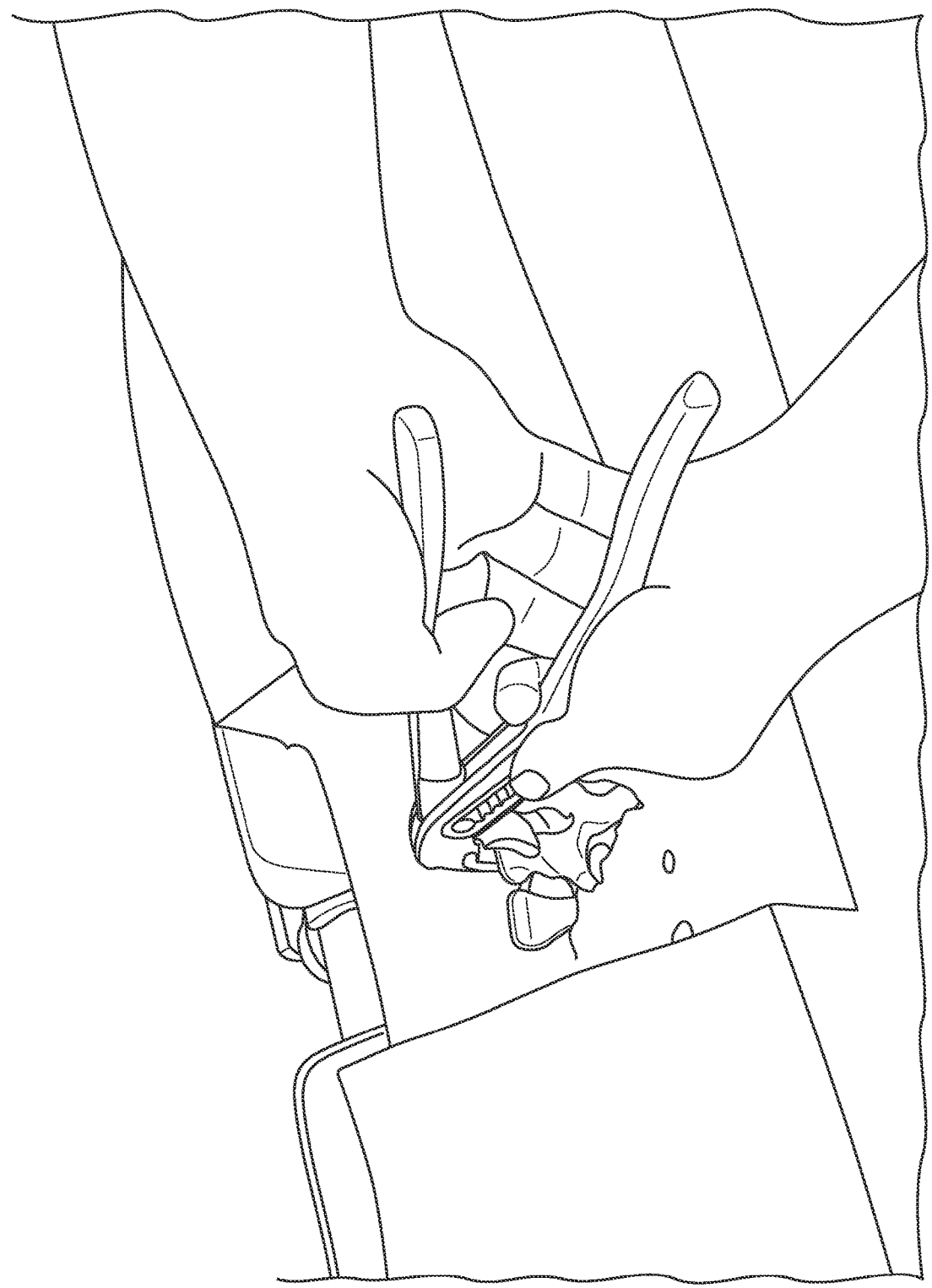
Figure 26:
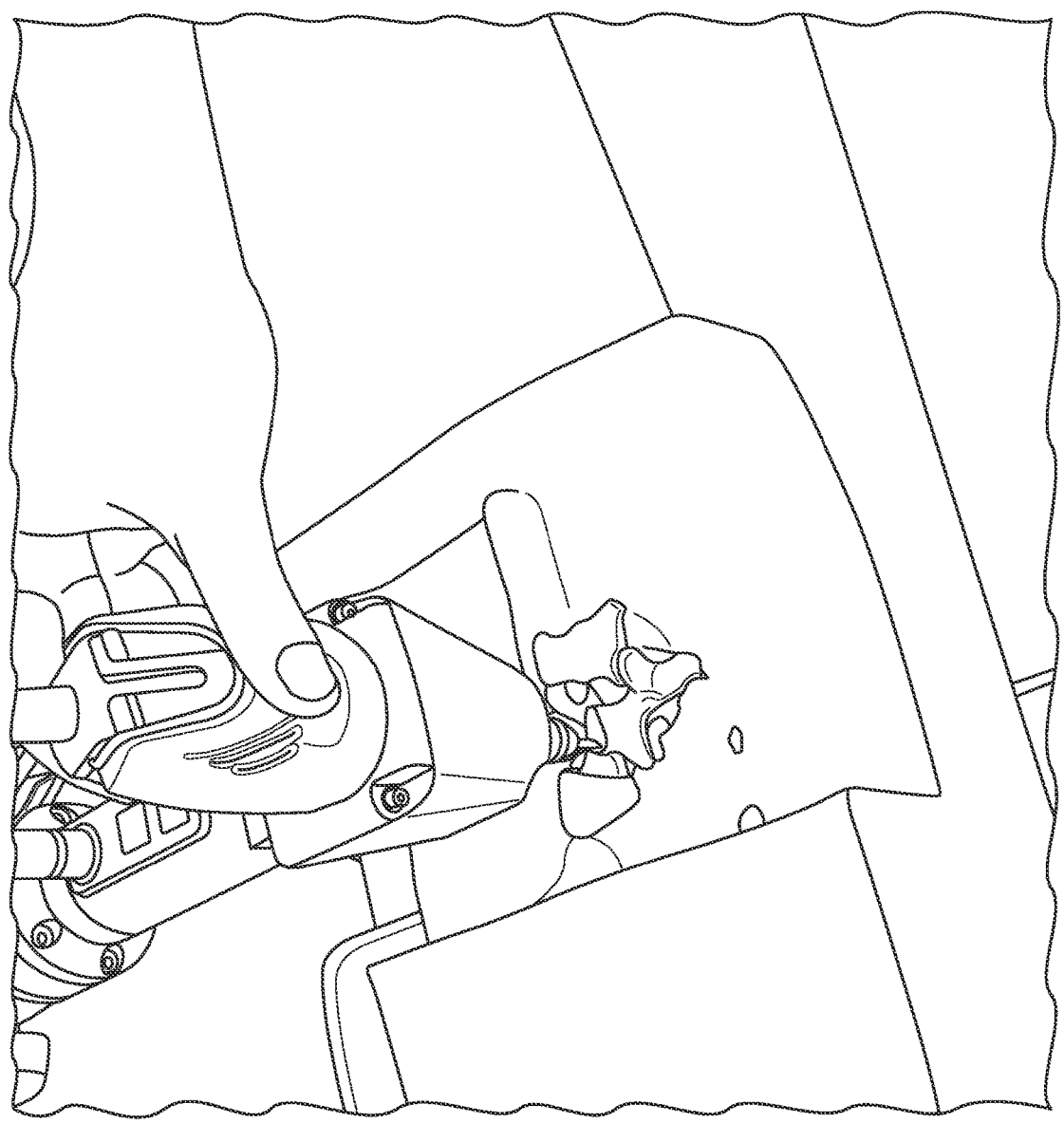
Figure 27:
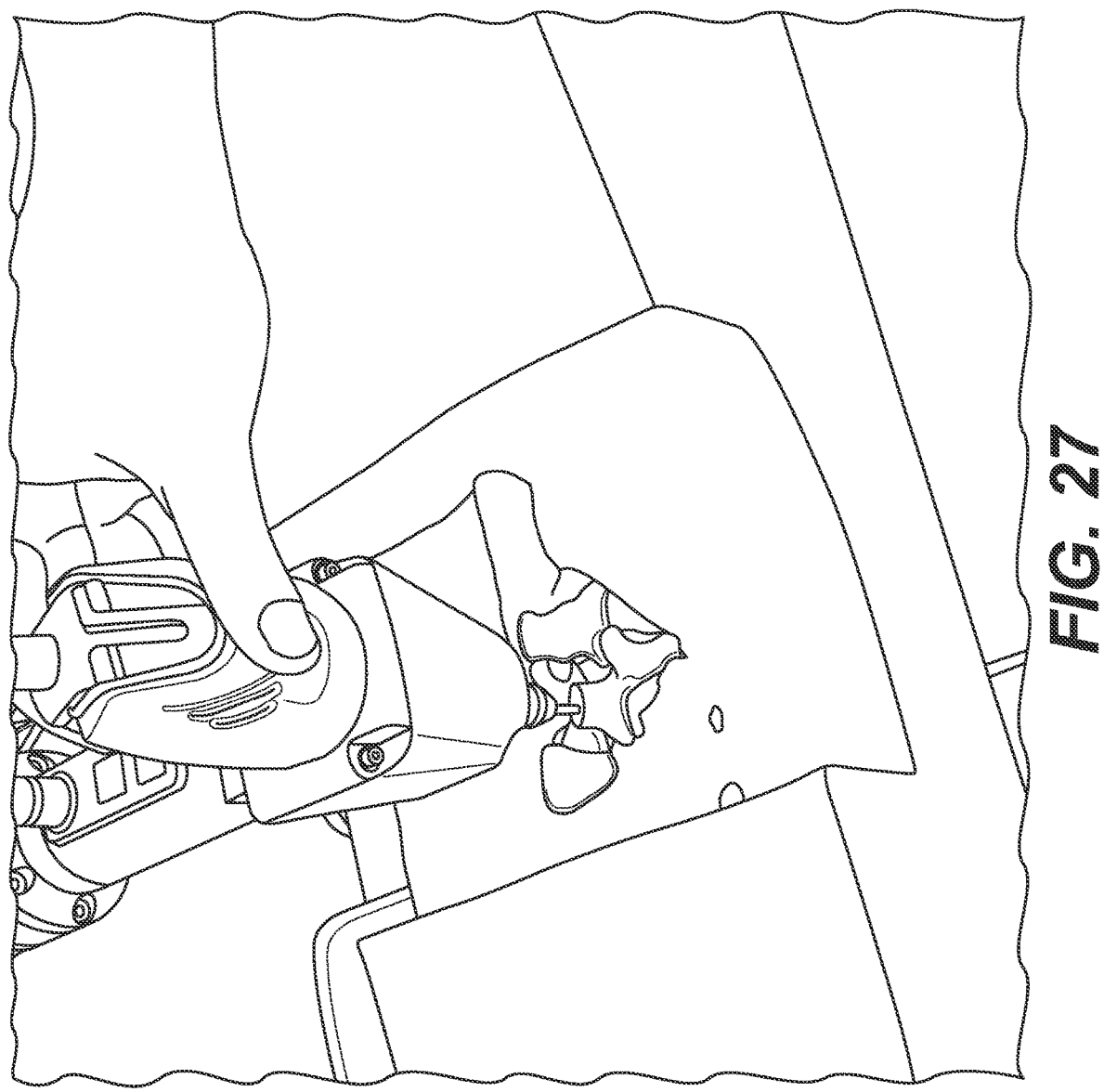
Figure 29:
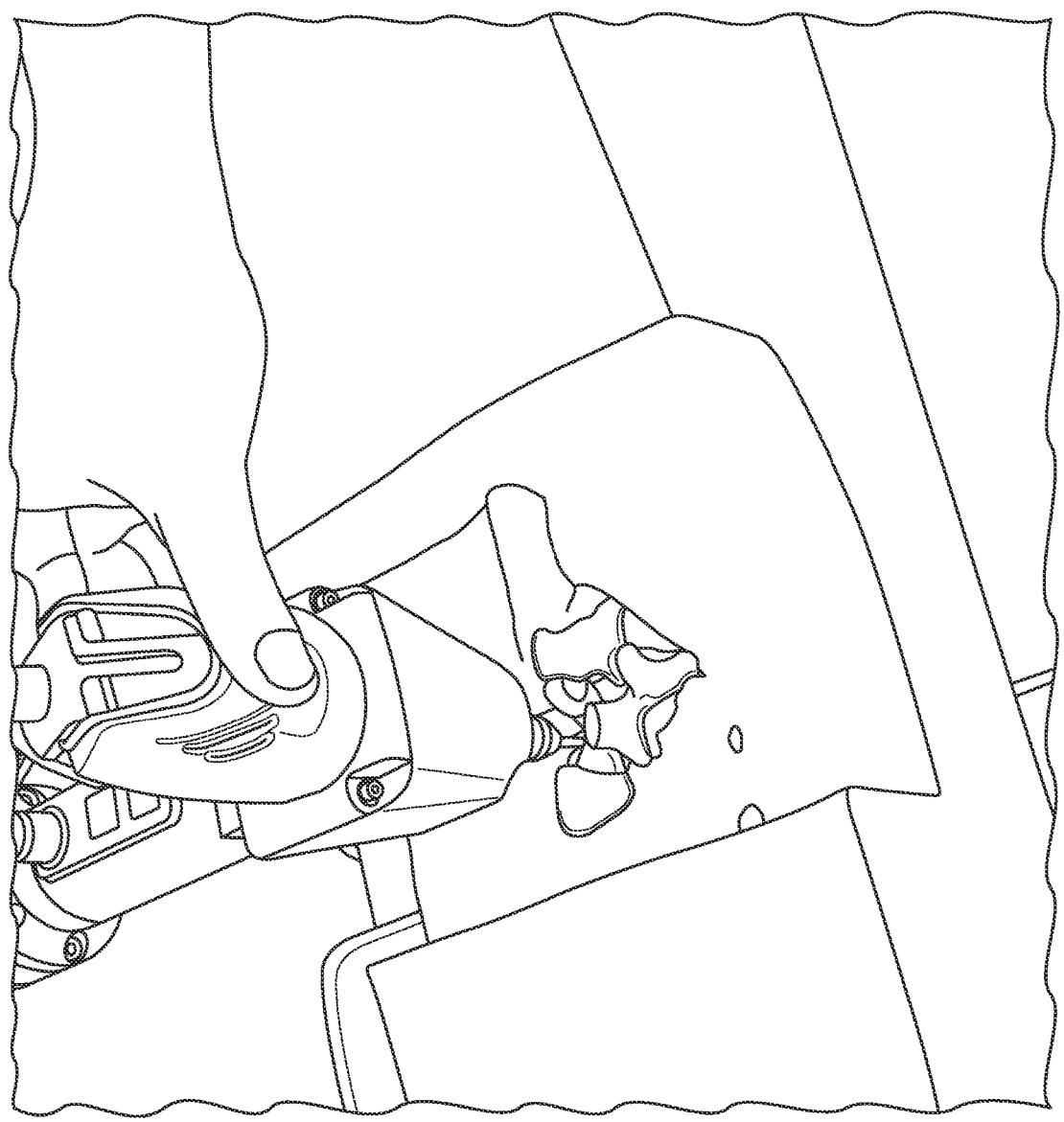
Figure 30:
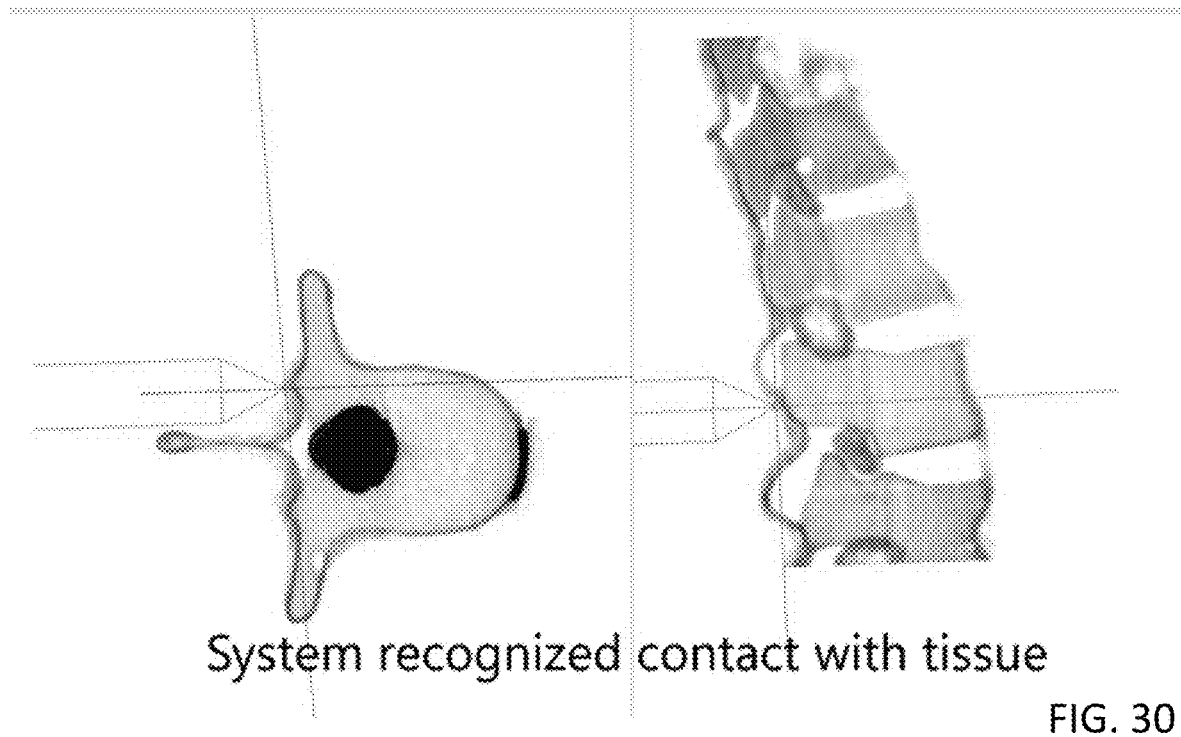
Figure 31:
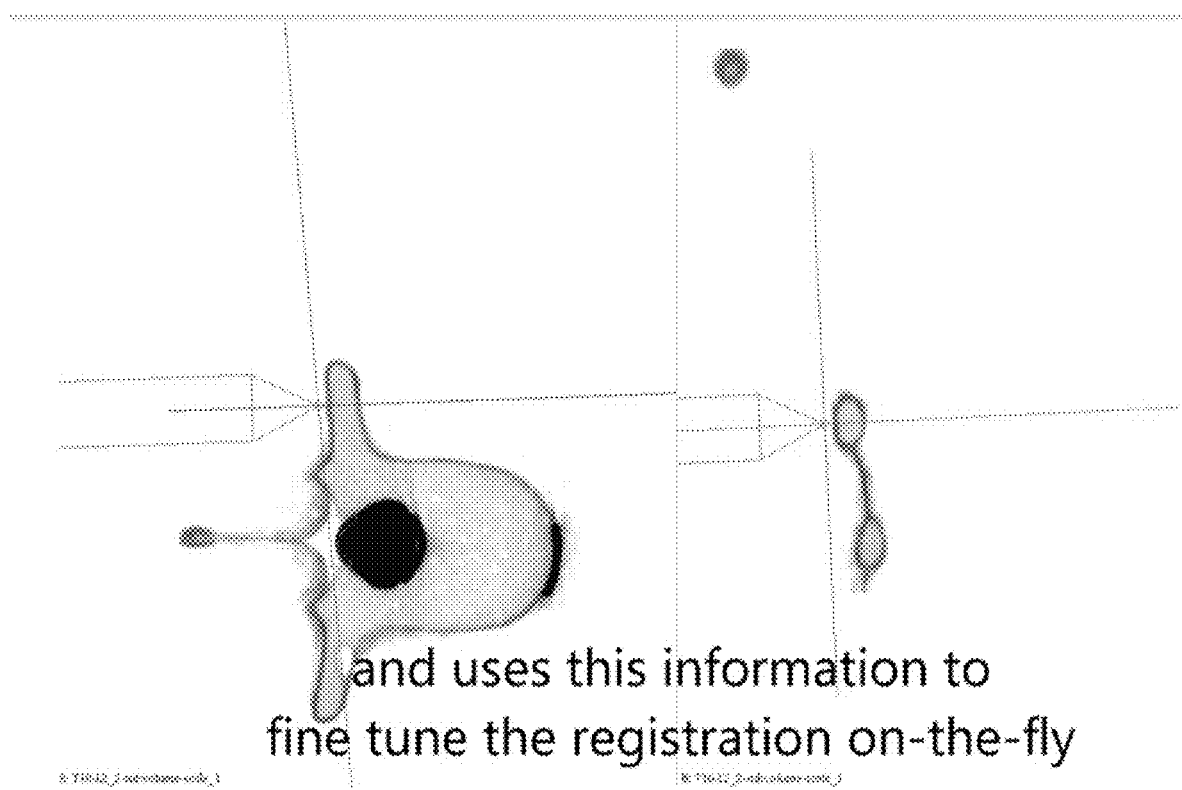

FIG. 25 shows a surgeon manually removing the spinous process of the vertebra. A volume removal can be performed manually or with a surgical instrwnent. Additionally, a volume removal can be performed freely, guided only by the surgeon (i.e., without defining an operational volume). In the case of laminectomy procedures, the spinous process is not important and is not and is not near a sensitive part of the patient's anatomy, so manual removal is sufficient. FIGS. 26-27 show a surgeon in the process of updating the model of the patient's anatomy by contacting the patient's anatomy in a plurality of points to generate a set of spatial coordinates. Because the set of spatial coordinates generated in the process shown in FIGS. 26-27 will include spatial coordinates for points that were previously interior points of the patient's anatomy, the patient's anatomical model can be updated accordingly. FIG. 28 shows the updated anatomical model with region of the model near the new surface highlighted in medium blue. FIG. 29 shows a surgeon in the process of re-registering the patient. The surgeon can contact the patient's anatomy at any point. There is no need to contact the patient at a specific point in order for successful re-registration to occur. In the case of the exemplary method, the re-registration will be performed based on the model of the patient updated to reflect removal of the spinous process. FIGS. 30 and 31 show a navigational display viewed by the surgeon during the re-registration process. The surgeon can see the surgical instrument contacting the bone of the patient to provide an additional check that the registration is accurate. For example, if the surgeon was physically contacting the patient's anatomy with the surgical instrument but the navigation display was not showing the terminal point of the surgical instrument at the surface of the patient's anatomy, then the surgeon would know that re-registration was necessary before proceeding with the surgical method.

Figure 32:
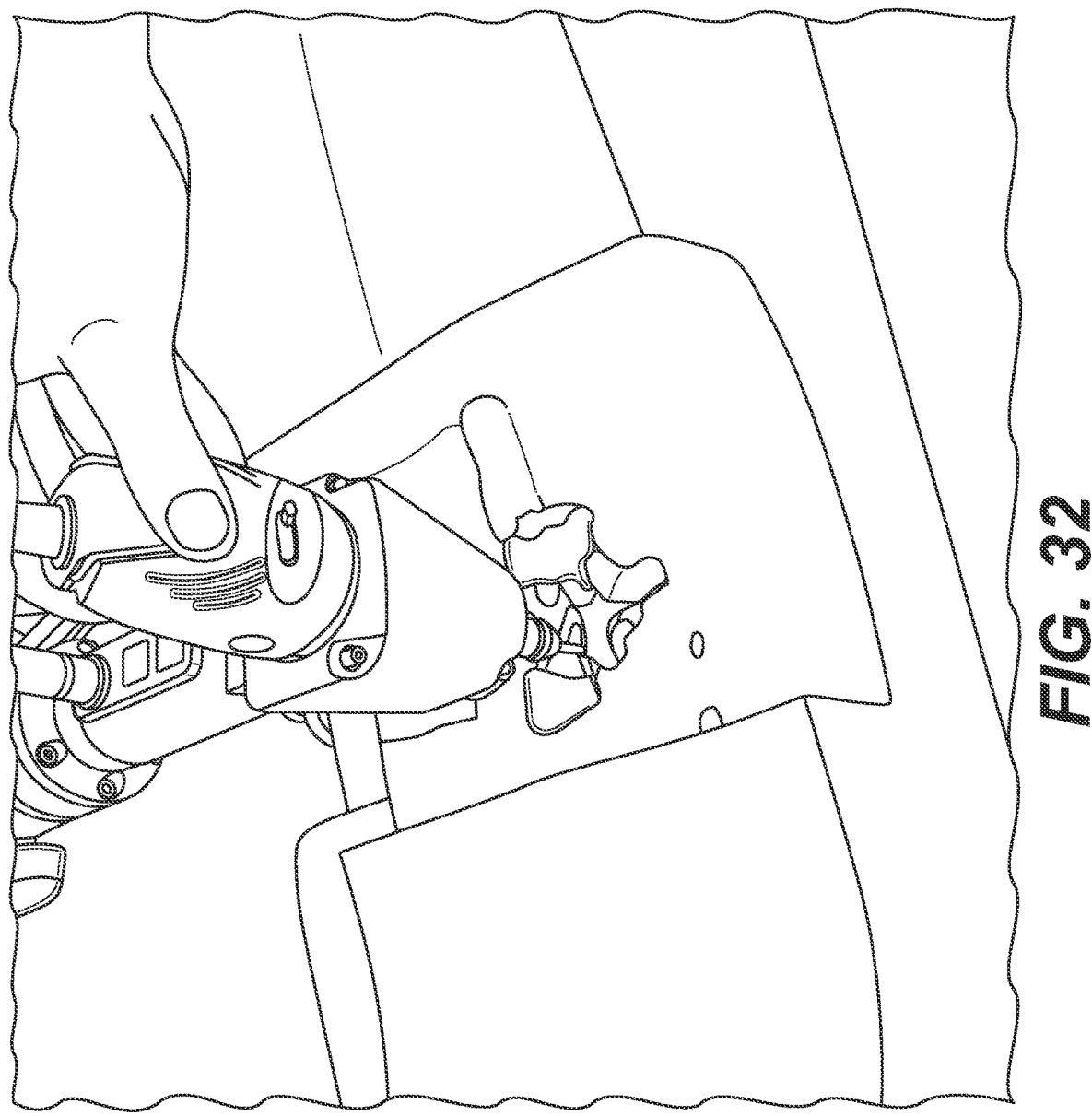
Figure 33:
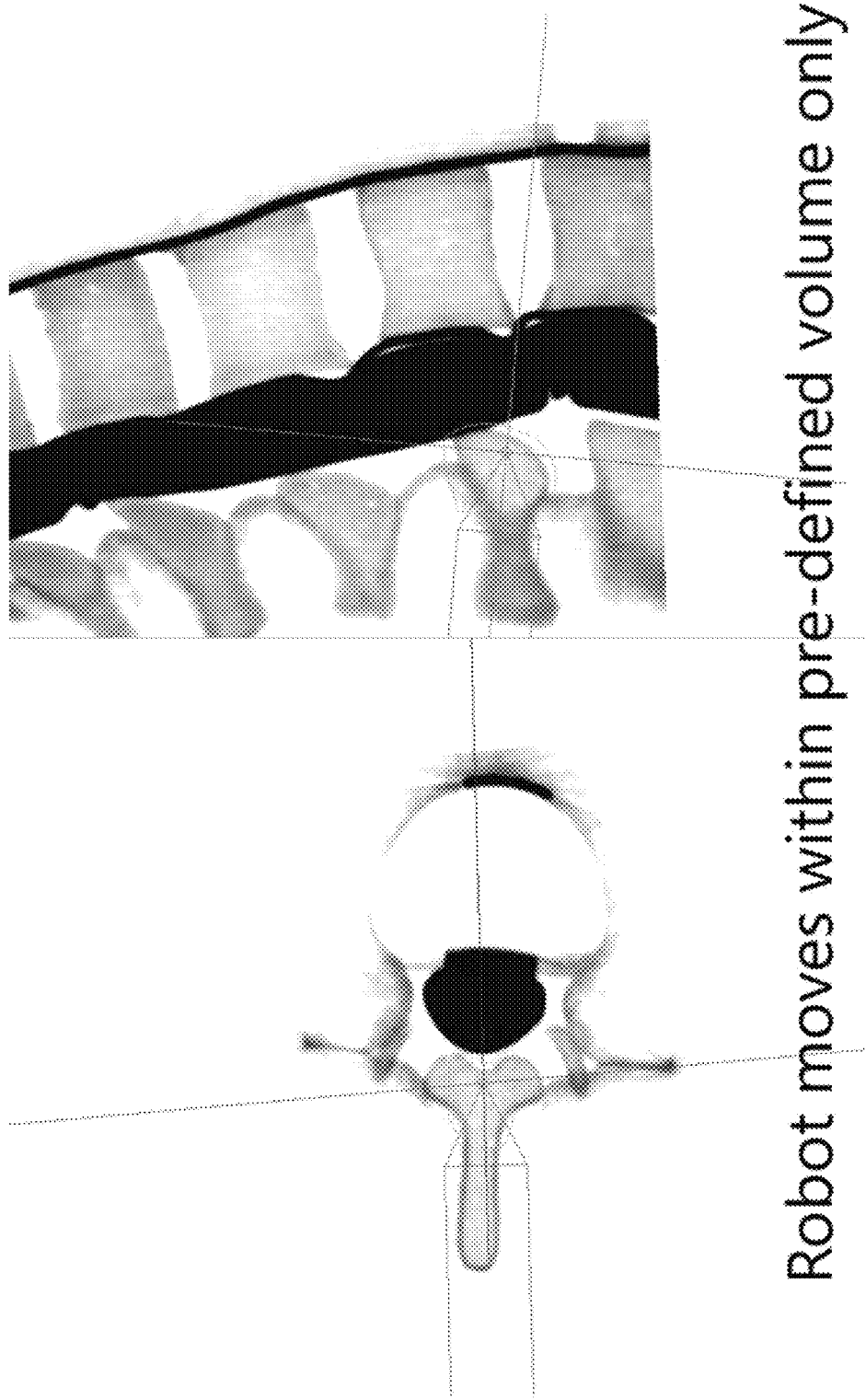

FIG. 32 shows the surgeon maneuvering the surgical instrument within an operational volume. The surgical instrument can be used to remove volume within the operational volume without risk to the surrounding volumes. During a laminectomy, the surgeon will operate close to a spinal nerve, so precision is critical to surgical outcomes. If the surgeon reaches the boundary of the operational volume, the robotic arm will be prevented from moving further and haptic feedback will signal to the surgeon to redirect movement away from and interior to the boundary. FIG. 33 shows a navigation display the surgeon uses during volume removal in the exemplary method. The surgeon can see the representation of the surgical instrument and its terminal point, medical image data modeling the patient's anatomy, and the operational volume of the current procedure. The surgeon can use this to intra-operatively redefine the operational volume if the original operational volume is determined to be insufficient or defective in some way. The overlay of the terminal point and the operational volume also provides a visual check for the surgeon that the registration is accurate. If the surgeon was feeling haptic feedback, but the terminal point appeared in the operational volume, the operational volume needs to be redefined and/or the patient needs to be re-registered.

Figure 34:
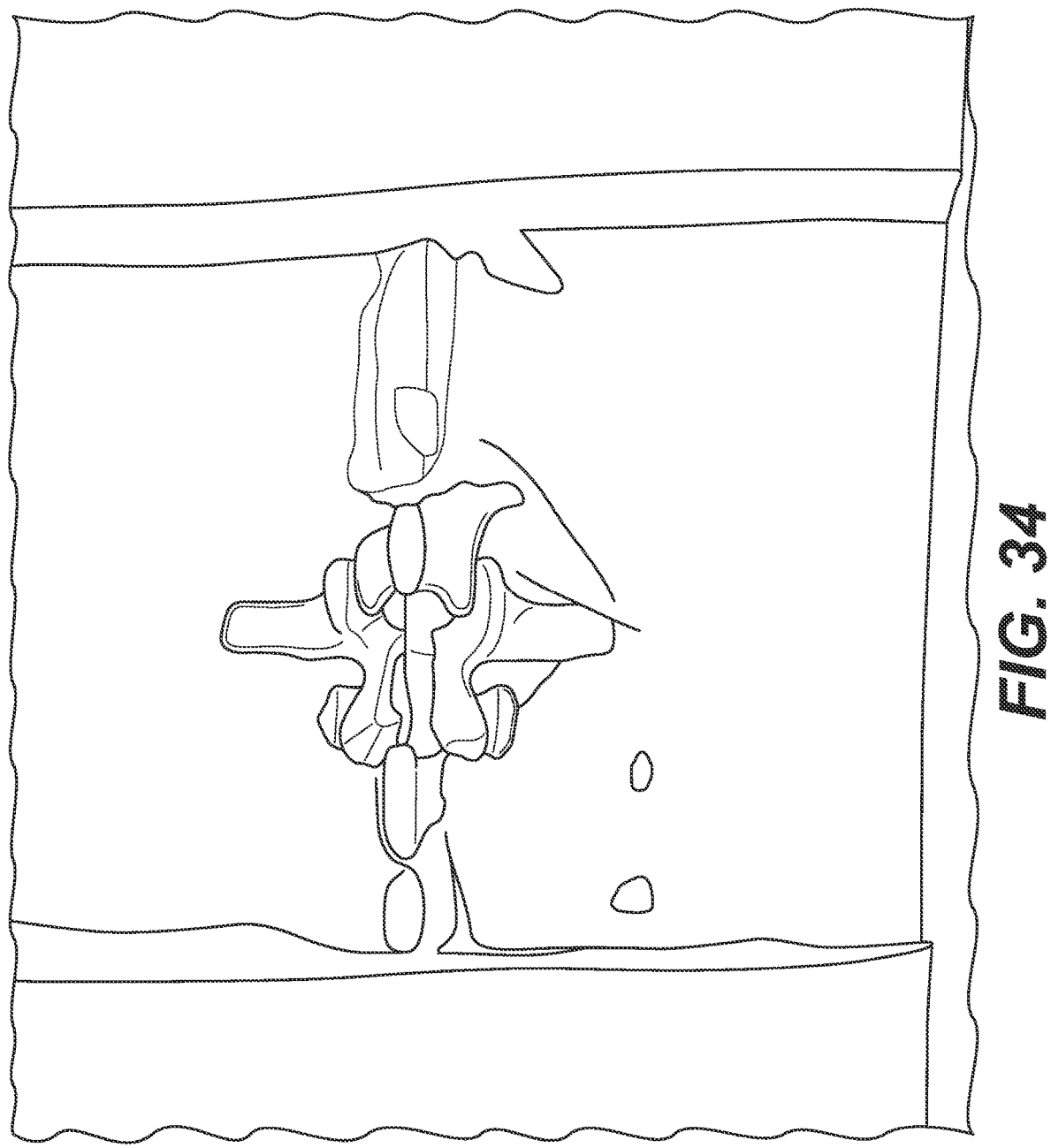
Figure 35:

FIGS. 34 and 35 show a patient's vertebra after completion of the laminectomy. The necessary volume was removed. By using an operational volume during the volume removal in combination with the use of the robotic surgical system, the volume removal can take place significantly faster than equivalent volume removals with known techniques. For example, in certain embodiments, the volume removal of a laminectomy occurs in 5 minutes or less, as compared to previously known techniques that generally take 30 minutes or more.

It is understood that surgical methods described herein are exemplary. Many surgical procedures require well-defined spatial relationships between a patient's anatomy and surgical instruments as well as operative volumes that constrain the movement of the surgical instruments. Other orthopedic and non-orthopedic methods are easily adapted to integrate the methods described herein. Other surgeries contemplated for use with robotic-based navigation systems and methods include, but are not limited to, orthopedic procedures, ENT procedures, and neurosurgical procedures. It is readily understood by one of ordinary skill in the art that such procedures may be performed using an open, percutaneous, or minimally invasive surgical (MIS) approach. It is also understood that any of the methods for determining coordinates and/or volumes using relevant coordinate systems described herein above can be used in any surgical method described herein.

FIG. 36 shows an illustrative network environment 3600 for use in the methods and systems described herein. In brief overview, referring now to FIG. 36, a block diagram of an exemplary cloud computing environment 3600 is shown and described. The cloud computing environment 3600 may include one or more resource providers 3602*a*, 3602*b*, 3602*c* (collectively, 3602). Each resource provider 3602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 3602 may be connected to any other resource provider 3602 in the cloud computing environment 3600. In some implementations, the resource providers 3602 may be connected over a computer network 3608. Each resource provider 3602 may be connected to one or more computing device 3604a, 3604b, 3604c (collectively, 3604), over the computer network 3608.

The cloud computing environment 3600 may include a resource manager 3606. The resource manager 3606 may be connected to the resource providers 3602 and the computing devices 3604 over the computer network 3608. In some implementations, the resource manager 3606 may facilitate the provision of computing resources by one or more resource providers 3602 to one or more computing devices 3604. The resource manager 3606 may receive a request for a computing resource from a particular computing device 3604. The resource manager 3606 may identify one or more resource providers 3602 capable of providing the computing resource requested by the computing device 3604. The resource manager 3606 may select a resource provider 3602 to provide the computing resource. The resource manager 3606 may facilitate a connection between the resource provider 3602 and a particular computing device 3604. In some implementations, the resource manager 3606 may establish a connection between a particular resource provider 3602 and a particular computing device 3604. In some implementations, the resource manager 3606 may redirect a particular computing device 3604 to a particular resource provider 3602 with the requested computing resource.

FIG. 37 shows an example of a computing device 3700 and a mobile computing device 750 that can be used in the methods and systems described in this disclosure. The computing device 3700 is intended to represent various forms of digital computers, such as laptops, desktops, workstations, personal digital assistants, servers, blade servers, mainframes, and other appropriate computers. The mobile computing device 3750 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 3700 includes a processor 3702, a memory 3704, a storage device 3706, a high-speed interface 3708 connecting to the memory 3704 and multiple high-speed expansion ports 3710, and a low-speed interface 3712 connecting to a low-speed expansion port 3714 and the storage device 3706. Each of the processor 3702, the memory 3704, the storage device 3706, the high-speed interface 3708, the high-speed expansion ports 3710, and the low-speed interface 3712, are interconnected using various busses, and may be mounted on a common motherboard or in other manners as appropriate. The processor 3702 can process instructions for execution within the computing device 3700, including instructions stored in the memory 3704 or on the storage device 3706 to display graphical information for a GUI on an external input/output device, such as a display 3716 coupled to the high-speed interface 3708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 3704 stores information within the computing device 3700. In some implementations, the memory 3704 is a volatile memory unit or units. In some implementations, the memory 3704 is a non-volatile memory unit or units. The memory 3704 may also be another form of computer-readable medium, such as a magnetic or optical disk.

The storage device 3706 is capable of providing mass storage for the computing device 3700. In some implementations, the storage device 3706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 3702), perform one or more methods, such as those described above. The instructions can also be stored by one or more storage devices such as computer- or machine-readable mediums (for example, the memory 3704, the storage device 3706, or memory on the processor 3702).

The high-speed interface 3708 manages bandwidth-intensive operations for the computing device 3700, while the low-speed interface 3712 manages lower bandwidth-intensive operations. Such allocation of functions is an example only. In some implementations, the high-speed interface 3708 is coupled to the memory 3704, the display 3716 (e.g., through a graphics processor or accelerator), and to the high-speed expansion ports 3710, which may accept various expansion cards (not shown). In the implementation, the low-speed interface 3712 is coupled to the storage device 3706 and the low-speed expansion port 3714. The low-speed expansion port 3714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 3700 may be implemented in a number of different forms, as shown in the figure. For example, it may be implemented as a standard server 3720, or multiple times in a group of such servers. In addition, it may be implemented in a personal computer such as a laptop computer 3722. It may also be implemented as part of a rack server system 3724. Alternatively, components from the computing device 3700 may be combined with other components in a mobile device (not shown), such as a mobile computing device 3750. Each of such devices may contain one or more of the computing device 3700 and the mobile computing device 3750, and an entire system may be made up of multiple computing devices communicating with each other.

The mobile computing device 3750 includes a processor 3752, a memory 3764, an input/output device such as a display 3754, a communication interface 3766, and a transceiver 3768, among other components. The mobile computing device 3750 may also be provided with a storage device, such as a micro-drive or other device, to provide additional storage. Each of the processor 3752, the memory 3764, the display 3754, the communication interface 3766, and the transceiver 3768, are interconnected using various buses, and several of the components may be mounted on a common motherboard or in other manners as appropriate.

The processor 3752 can execute instructions within the mobile computing device 3750, including instructions stored in the memory 3764. The processor 3752 may be implemented as a chipset of chips that include separate and multiple analog and digital processors. The processor 3752 may provide, for example, for coordination of the other components of the mobile computing device 3750, such as control of user interfaces, applications run by the mobile computing device 3750, and wireless communication by the mobile computing device 3750.

The processor 3752 may communicate with a user through a control interface 3758 and a display interface 3756 coupled to the display 3754. The display 3754 may be, for example, a TFT (Thin-Film-Transistor Liquid Crystal Display) display or an OLED (Organic Light Emitting Diode) display, or other appropriate display technology. The display interface 3756 may comprise appropriate circuitry for driving the display 3754 to present graphical and other information to a user. The control interface 3758 may receive commands from a user and convert them for submission to the processor 3752. In addition, an external interface 3762 may provide communication with the processor 3752, so as to enable near area communication of the mobile computing device 3750 with other devices. The external interface 3762 may provide, for example, for wired communication in some implementations, or for wireless communication in other implementations, and multiple interfaces may also be used.

The memory 3764 stores information within the mobile computing device 3750. The memory 3764 can be implemented as one or more of a computer-readable medium or media, a volatile memory unit or units, or a non-volatile memory unit or units. An expansion memory 3774 may also be provided and connected to the mobile computing device 3750 through an expansion interface 3772, which may include, for example, a SIMM (Single in Line Memory Module) card interface. The expansion memory 3774 may provide extra storage space for the mobile computing device 3750, or may also store applications or other information for the mobile computing device 3750. Specifically, the expansion memory 3774 may include instructions to carry out or supplement the processes described above, and may include secure information also. Thus, for example, the expansion memory 3774 may be provided as a security module for the mobile computing device 3750, and may be programmed with instructions that permit secure use of the mobile computing device 3750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 3752), perform one or more methods, such as those described above. The instructions can also be stored by one or more storage devices, such as one or more computer- or machine-readable mediums (for example, the memory 3764, the expansion memory 3774, or memory on the processor 3752). In some implementations, the instructions can be received in a propagated signal, for example, over the transceiver 3768 or the external interface 3762.

The mobile computing device 3750 may communicate wirelessly through the communication interface 3766, which may include digital signal processing circuitry where necessary. The communication interface 3766 may provide for communications under various modes or protocols, such as GSM voice calls (Global System for Mobile communications), SMS (Short Message Service), EMS (Enhanced Messaging Service), or MIMS messaging (Multimedia Messaging Service), CDMA (code division multiple access), TOMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 3768 using a radio-frequency. In addition, short-range communication may occur, such as using a Bluetooth®, Wi-Fi™, or other such transceiver (not shown). In addition, a GPS (Global Positioning System) receiver module 3770 may provide additional navigation- and location-related wireless data to the mobile computing device 3750, which may be used as appropriate by applications running on the mobile computing device 3750.

The mobile computing device 3750 may also communicate audibly using an audio codec 3760, which may receive spoken information from a user and convert it to usable digital information. The audio codec 3760 may likewise generate audible sound for a user, such as through a speaker, e.g., in a handset of the mobile computing device 3750. Such sound may include sound from voice telephone calls, may include recorded sound (e.g., voice messages, music files, etc.) and may also include sound generated by applications operating on the mobile computing device 3750.

The mobile computing device 3750 may be implemented in a number of different forms, as shown in the figure. For example, it may be implemented as a cellular telephone 3780. It may also be implemented as part of a smart-phone 3782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Having described certain implementations of methods and apparatus for robotic navigation of robotic surgical systems, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A robotic surgical system for registering a patient's anatomy with an instrument attached to an end-effector of a robotic arm of the robotic surgical system, the system comprising:
    a robotic arm including an end-effector having an instrument attached thereto;
    a force sensor attached directly or indirectly to the robotic arm; and
    a processor and a memory having instructions stored thereon, wherein the instructions, when executed by the processor, cause the processor to:
        receive haptic feedback, from the force sensor, prompted by movement of the instrument attached to the end-effector;
        determine that the haptic feedback corresponds to contact of the instrument with a bone;
        determine a set of spatial coordinates, wherein the set of spatial coordinates comprises a spatial coordinate for each contact of the instrument with the bone, expressed using a robot coordinate system, wherein each spatial coordinate corresponds to a point on the surface of an anatomical volume;
        determine a set of medical image data coordinates expressed using a medical image data coordinate system that correspond to a patient anatomy surface;
        map the surface corresponding to the set of spatial coordinates to the patient anatomy surface corresponding to the set of medical image data;
        generate a coordinate mapping between the robot coordinate system and the medical image data coordinate system based on the mapping between the surface corresponding to the set of spatial coordinates and the surface corresponding to the set of medical image data coordinates;
        modifying, by the processor, the set of medical image data coordinates that define the surface of the volume of the patient's anatomy with a set of interior medical image data coordinates such that a first volume defined by the set of medical image data coordinates is larger than a second volume defined by the modified set of medical image data coordinates; and
        store the coordinate mapping, thereby registering the patient's anatomy based on the determination of contact of the instrument with the bone.

2. The system of claim 1, wherein the instructions, when executed by the processor, cause the processor to:
    output rendering data for display, wherein the rendering data corresponds to a representation of a position of a member and at least a portion of the medical image data based on the coordinate mapping, wherein the member is selected from the group consisting of: the end-effector, the instrument, and a surgical instrument.

3. The system of claim 2, wherein the instructions, when executed by the processor, cause the processor to:
    generate new rendering data by modifying the rendering data based on a change in the end-effector's position; and output the new rendering data for display.

4. The system of claim 1, wherein the end-effector includes a fiducial marker with known size and shape such that the spatial coordinate is determined using a spatial relationship between the fiducial marker and the patient's anatomy.

5. A robotic surgical system for registering a patient's anatomy with an instrument attached to an end-effector of a robotic arm of the robotic surgical system, the system comprising:
    a robotic arm with an end-effector having an instrument attached thereto;
    a force sensor attached to the instrument and
    a processor and a memory having instructions stored thereon, wherein the instructions, when executed by the processor, cause the processor to:
        receive haptic feedback, from the force sensor, prompted by movement of the instrument attached to the end-effector;
        determine that the haptic feedback corresponds to contact of the instrument with a bone;
        determine a set of spatial coordinates, wherein the set of spatial coordinates comprises a spatial coordinate for each contact of the instrument with the material, expressed using a robot coordinate system, wherein each spatial coordinate corresponds to a point on the surface of an anatomical volume;

determine a set of medical image data coordinates expressed using a medical image data coordinate system that correspond to a patient anatomy surface;

map the surface corresponding to the set of spatial coordinates to the patient anatomy surface corresponding to the set of medical image data;

generate a coordinate mapping between the robot coordinate system and the medical image data coordinate system based on the mapping between the surface corresponding to the set of spatial coordinates and the surface corresponding to the set of medical image data coordinates;

modifying, by the processor, the set of medical image data coordinates that define the surface of the volume of the patient's anatomy with the set of interior medical image data coordinates such that a first volume defined by the set of medical image data coordinates is larger than a second volume defined by the modified set of medical image data coordinates; and store the coordinate mapping, thereby dynamically registering the patient's anatomy based on the determination of contact of the instrument with the bone.

* * * * *